(12) United States Patent
Tainsky et al.

(10) Patent No.: US 10,782,302 B2
(45) Date of Patent: Sep. 22, 2020

(54) DETECTORS OF SERUM BIOMARKERS FOR PREDICTING OVARIAN CANCER RECURRENCE

(71) Applicants: Michael Tainsky, Southfield, MI (US); Madhumita Chatterjee, Lake Orion, MI (US); Gregory Dyson, Northville, MI (US); Nancy Levin, Birmingham, MI (US)

(72) Inventors: Michael Tainsky, Southfield, MI (US); Madhumita Chatterjee, Lake Orion, MI (US); Gregory Dyson, Northville, MI (US); Nancy Levin, Birmingham, MI (US)

(73) Assignee: Wayne State University, Detroit, MI (US)

( * ) Notice: Subject to any disclaimer, the term of this patent is extended or adjusted under 35 U.S.C. 154(b) by 43 days.

(21) Appl. No.: 15/785,898

(22) Filed: Oct. 17, 2017

(65) Prior Publication Data

US 2018/0031565 A1 Feb. 1, 2018

Related U.S. Application Data

(63) Continuation-in-part of application No. 14/398,773, filed as application No. PCT/US2013/039658 on May 6, 2013, now Pat. No. 9,797,906.

(60) Provisional application No. 61/642,488, filed on May 4, 2012.

(51) Int. Cl.
| | | |
|---|---|---|
| *C07K 14/10* | (2006.01) | |
| *G01N 33/574* | (2006.01) | |
| *C07K 14/47* | (2006.01) | |
| *A61K 39/00* | (2006.01) | |
| *A61K 38/00* | (2006.01) | |

(52) U.S. Cl.
CPC ... *G01N 33/57484* (2013.01); *C07K 14/4748* (2013.01); *G01N 33/57449* (2013.01); *A61K 38/00* (2013.01); *A61K 39/00* (2013.01)

(58) Field of Classification Search
None
See application file for complete search history.

(56) References Cited

U.S. PATENT DOCUMENTS

2005/0239146 A1* 10/2005 Tainsky ........... G01N 33/57411
435/7.23
2014/0256034 A1* 9/2014 Chung .................... A61L 31/16
435/325

FOREIGN PATENT DOCUMENTS

WO WO2004060262 A2 * 7/2004
WO WO2012124998 * 9/2012

OTHER PUBLICATIONS

Chatterjee et al (Gynecologic Oncology Reports 21:37-44, only published on Jun. 6, 2017 (Year: 2017).*
NCBI gene bank accession No. AAX99363 (Year: 2005).*
HARS recombinant protein NP-002100 (MyBiosource, Cat No. MBS203575 (Year: 2019).*

* cited by examiner

*Primary Examiner* — Lei Yao
(74) *Attorney, Agent, or Firm* — Kohn & Associates, PLLC

(57) ABSTRACT

Polypeptide marker antigens for detecting the presence of autoantibody biomarkers associated with ovarian cancer recurrence, each of the polypeptide marker antigens binding specifically to at least one autoantibody marker. An antibody binding assay for detecting the presence of autoantibody biomarkers associated with ovarian cancer recurrence, and methods for performing the assay. Methods for determining ovarian cancer recurrence in an ovarian cancer patient. A method for isolating antibodies specific for ovarian cancer by their affinity to the polypeptide marker antigens, and antibodies isolated by that method.

2 Claims, 16 Drawing Sheets

Specification includes a Sequence Listing.

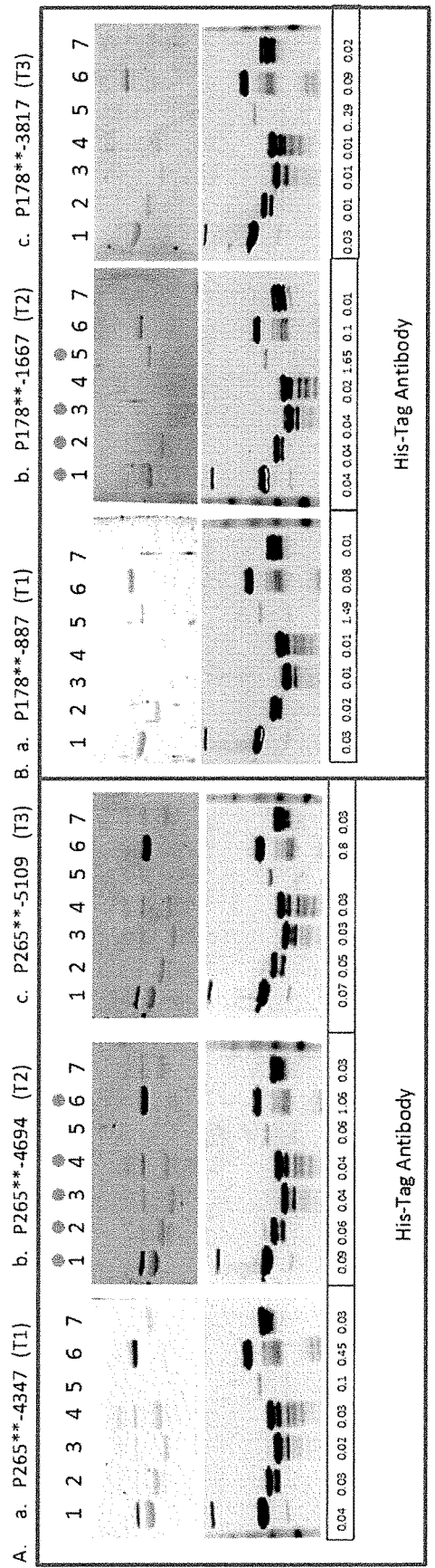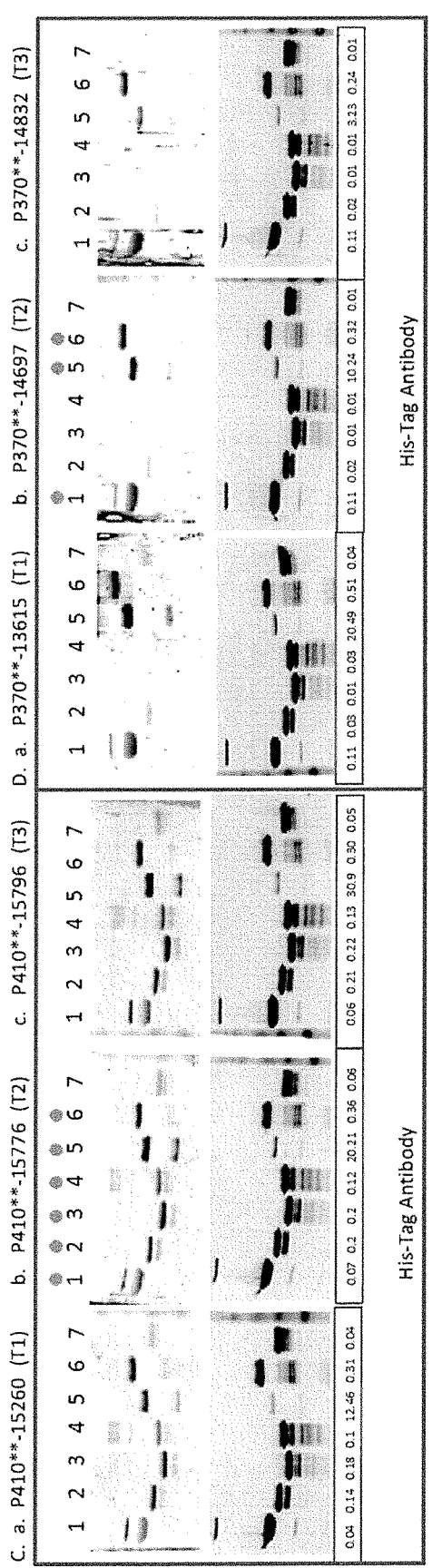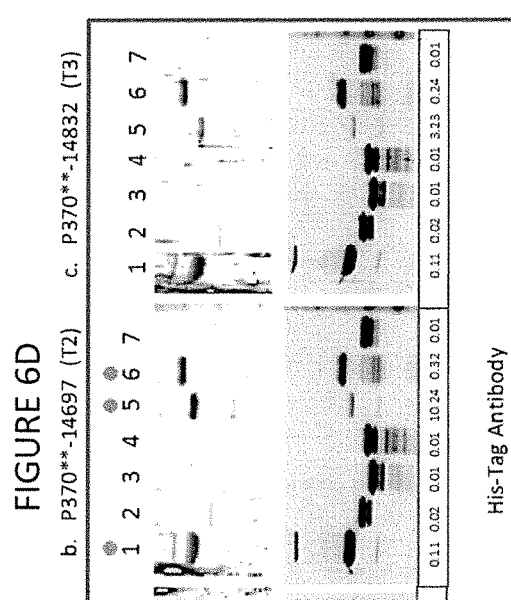

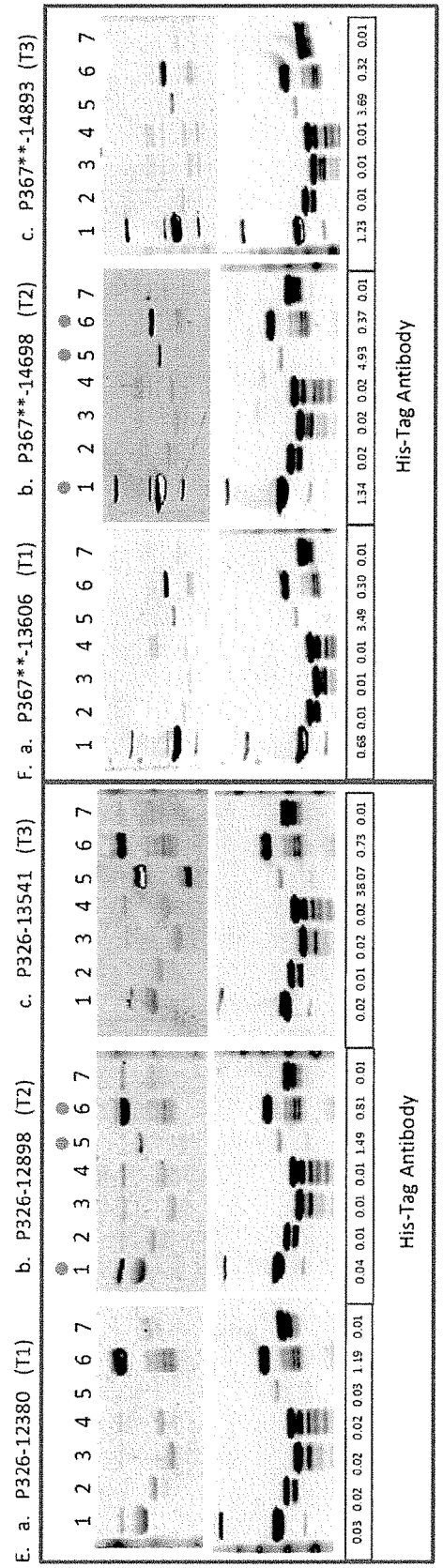
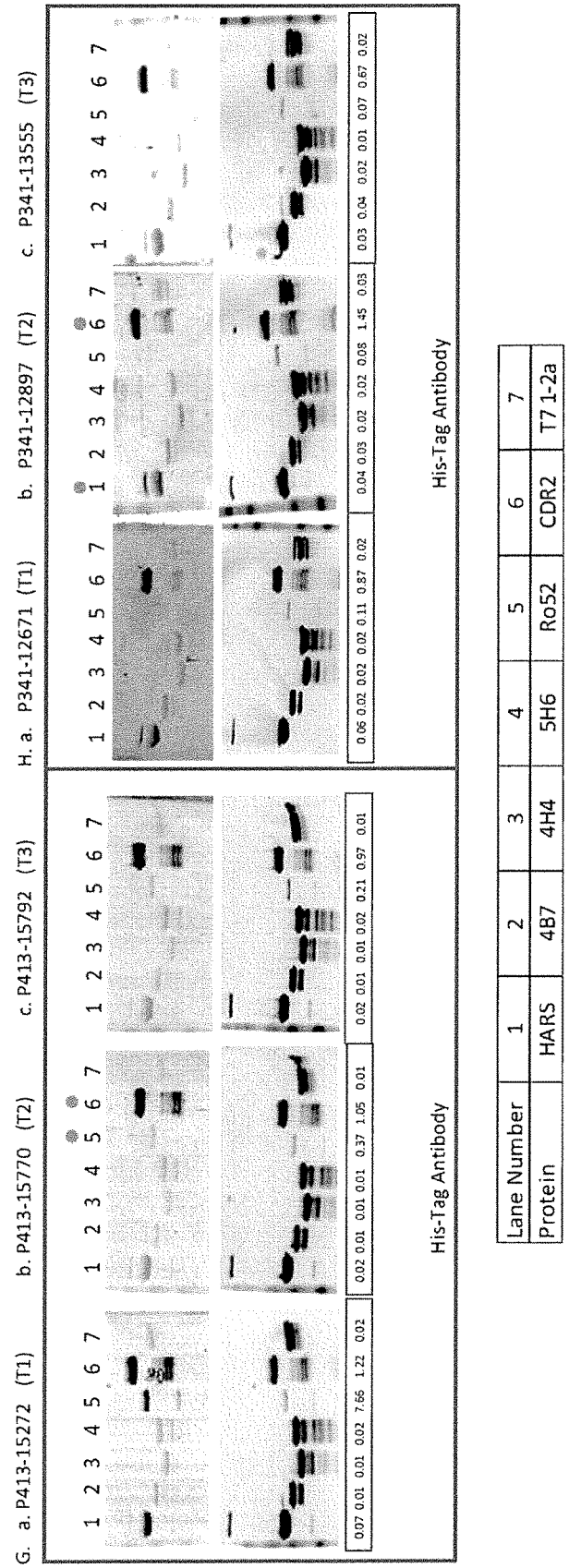

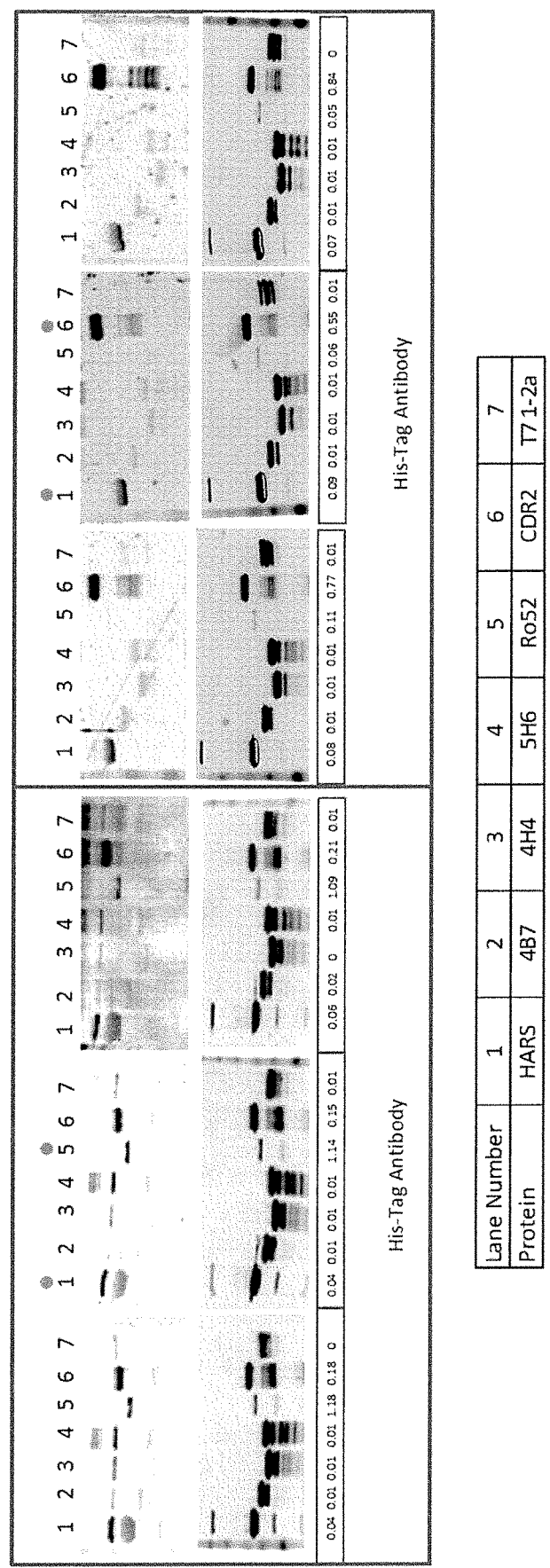

DETECTORS OF SERUM BIOMARKERS FOR PREDICTING OVARIAN CANCER RECURRENCE

GRANT INFORMATION

Research in this application was supported in part by grants from the National Institutes of Health (NIH Grant Nos. R21/R33-CA100740, 1R01CA160541, and R21 CA187278-01). The Government has certain rights in the invention.

TECHNICAL FIELD

The present invention relates to an assay and method for diagnosing disease. More specifically, the present invention relates to markers and assays for predicting or detecting recurrence of cancer and for enhancing the treatment of recurrent cancer

BACKGROUND OF THE INVENTION

The asymptomatic nature of OVCA together with lack of effective diagnostic screening tools makes the disease extremely difficult to detect at an early stage. Consequently, OVCA is often diagnosed at an advanced stage in approximately 70% of patients. Despite an initial response to primary, or "first-line", treatment more than 85% of patients with advanced disease will experience OVCA recurrence after the completion of first-line treatment even with optimal surgical cytoreduction and platinum-based combination chemotherapy. Patients bearing platinum-sensitive tumors have a relapse-free period of at least 6 months following their last platinum treatment compared to patients bearing platinum resistant tumors who fail to achieve complete response after first-line treatment and relapse in less than 6 months from the completion of therapy. Evaluation of effects of primary treatment and the early detection of recurrence in those with platinum-sensitive tumors is an important goal of routine follow-up to improve the life expectancy.

Over the years CA125 has emerged as a useful biomarker for monitoring of OVCA recurrence. The clinical symptoms of recurrence are determined by measuring the level of serum CA125, one of the most extensively used tumor biomarkers in standard clinical practice for disease surveillance. In a randomized trial performed by Rustin et al. it was shown that ovarian cancer patients who had increased CA125 level before the clinical recurrence followed by chemotherapy treatments did not have a survival benefit compared to the other arm of ovarian cancer patients who received chemotherapy based on clinical evidences of ovarian cancer recurrence. Conversely, a recent study has shown that ovarian cancer patients at risk of recurrence may benefit from early initiation of treatments. Guo et al. reported that when setting the CA125 threshold to 10 U/ml instead of 35 U/ml, distant recurrent lesions located in spleen, liver and pelvic region were detected in 3 postoperative epithelial ovarian carcinoma patients who had CA125 values 14.5 U/ml, 13.5 U/ml and 20.9 U/ml respectively. In all of these patients, recurrent lesions were detected 2-3 months prior to clinical recurrence and all the patients underwent second cytoreductive surgery. After the surgery, their CA125 values were less than 10 U/ml and the patients were in good health. Thus, early treatments were shown to be necessary when there is a risk of recurrence involved. Their study may not be in agreement with the randomized trial by Rustin et al. where only chemotherapy was considered as an early treatment and the impact of second-line cytoreductive surgery was not taken into consideration. Also, patients who participated in that trial were not treated with new salvage chemotherapy regimens that might have improved prognosis. Another study reported by Yang et al. showed that in a study population of 152 ovarian cancer patients, the average elevation of CA125 level was 116.28 U/ml at the time of clinical recurrence and the average time that elapsed from the rise in CA125 to the time when recurrent lesions were detected by physical or radiologic examinations was 122 days. The sensitivity and specificity of detecting early ovarian cancer recurrence using CA125 tumor marker alone with a threshold of 35 U/ml was 67.39% and 86.79% respectively. Despite its utility in ovarian cancer diagnosis and disease monitoring, CA125 has its limitations. A rise in CA125 to 1,000 IU/ml has been observed in many benign gynecological conditions, such as, intramural leiomyoma, adnexal cystic mass, and ovarian endometrioma. Other studies have documented normalization of CA125 in 50% of patients with ovarian cancer with microscopic disease at the second-look laparotomy. Therefore, there is a dearth of sensitive biomarkers that can predict ovarian cancer recurrence with a sufficient lead time prior to the rise in CA125 during cancer surveillance, so that the patients can benefit from an early therapeutic intervention capable of prolonging the disease-free interval and improve overall survival.

Although CA125 is the most extensively investigated biomarker for diagnosis and monitoring of OVCA, a variety of other tumor biomarkers have been reported to be useful for monitoring response to therapy or indicating relapse during follow-up visits. Anastasi and colleagues conducted a follow-up retrospective study for survival analysis of 8/32 patients with advanced OVCA by evaluating the levels of human epididymis protein 4 (HE4) and CA125 in the serum samples that were collected at the time of diagnosis and at intervals during 16-20 months after surgery. Their study showed that 5/8 patients had an increase in HE4 level above the cut-off value that preceded the rise of CA125 by 5-8 months. This early increase in HE4 level was associated with the relapse of the disease. Another study showed that the level of Osteopontin (OPN), a putative plasma biomarker, increased earlier than CA125 in 90% of the patients developing progressive or recurrent epithelial OVCA (median lead time, 3 months) although its role in predicting clinical response to therapy was considered inferior to CA125. Tassi and colleagues reported significant elevation in the expression of Mammaglobin B (MGB-2), a secretoglobin family member, in epithelial OVCA. Univariate survival analysis on 106 OVCA patients enrolled in their study revealed significant correlation of MGB-2 expression with reduced risks of cancer-related death, recurrence and disease progression ($p<0.05$). In another study, the utility of a biomarker panel comprised of HE4, MMP7 and Glycodelin was evaluated to predict recurrence in a longitudinal monitoring cohort of 30 patients with advanced OVCA. The results indicated that in 27/30 patients who experienced recurrence following initial response to chemotherapy, this biomarker panel predicted recurrence with a sensitivity of 100% compared to 96% for CA125 alone. In 56% patients, the level of one or more panel biomarkers was elevated 6-69 weeks before the rise in CA125 and prior to other clinical evidence of recurrence. Other studies examined the BRCA-ness profile of sporadic ovarian carcinomas in late stage OVCA patients in which the majority had poorly differentiated grade 3 cancers and serous histology. One such study indicated that 41% (7/17) patients who recurred within first year of diagnosis, had tumors with high expression of PARP, FANCD2 and p53 proteins compared to 19% (29/149) patients in the non-recurrence group whose tumors had low expression of the above 3 proteins.

Tumor autoantibodies develop at very early stage, well before the clinical manifestations of the disease because of the activation of humoral immune responses due to the presence of small amounts of tumor associated antigens (TAAs) even at very low tumor burden. Thus, antibodies against tumor specific proteins may provide the earliest candidate biomarkers for detecting OVCA as well as for monitoring OVCA during the first-line chemotherapy that will provide a signal for the risk of developing OVCA recurrence.

Numerous studies have shown the role of tumor autoantibodies as biomarkers for ovarian cancer diagnosis and its recurrence. These autoantibodies to tumor associated antigens (TAAs) arise due to the generation of humoral immune response before evidence of clinical symptoms in cancer patients. Our previous study indicated that a 3 biomarker panel, one being a peptide epitope from a known paraneoplastic antigen, predicted ovarian cancer recurrence at a median lead time of 9.07 months with 94.7% sensitivity, 86.7% specificity, and 93.3% accuracy, in a cohort of ovarian cancer patients where normalization of CA125 had occurred after the surgery and completion of chemotherapy. Paraneoplastic antigens can elicit a humoral immune response in cancer patients as these antigens are expressed in the cells of nervous system and tumor. The appearance of these onconeural antibodies in ovarian cancer patients leads to the development of various neurological disorders called paraneoplastic syndromes, particularly dermatomyositis or polymyositis. The diagnosis of ovarian cancer can be preceded by the occurrence of dermatomyositis or polymyositis. Marie et al. reviewed the medical data to evaluate the clinical outcome of 89 patients who had antisynthetase syndrome (ASS) associated with Jo-1 antibodies that target HARS antigen. Concurrent occurrence of Ro52 antibodies was also observed in 36 out of 89 patients. It was reported that 7/36 (19.4%) had colon, breast, ovarian, or esophageal cancers and 28/36 (77%) had interstitial lung disease with poorer prognosis. Other studies have shown that patients with ovarian cancer in association with paraneoplastic cerebellar degeneration harbor Yo antibodies directed against CDR2 antigen that is expressed in tumor cells and Purkinje cells. The frequency of appearance of Yo antibodies in patients with paraneoplastic cerebellar degeneration associated with ovarian cancer and breast cancer was found to be 13/557 (2.3%) and 4/253 (1.6%) respectively. The diagnosis of 2/13 ovarian cancer patients was preceded by the appearance of paraneoplastic cerebellar degeneration. These onconeural antibodies can occur in the absence of paraneoplastic symptoms leading to their diagnostic utility in asymptomatic subjects. Although the clinical implication of these onconeural antibodies as biomarkers for early diagnosis of ovarian cancer has been reported in many case studies, the usefulness of these antibodies has yet to be evaluated in monitoring disease status in ovarian cancer patients after cytoreductive surgery and chemotherapy treatments.

There is a need for reagents that sensitively and specifically detect autoantibody biomarkers associated with ovarian cancer recurrence, and for methods of using these reagents to predict the recurrence of ovarian cancer. There is also a need for methods of directing OVCA treatment selectively toward patients at risk of recurrence.

SUMMARY OF THE INVENTION

The present invention provides polypeptide marker antigens for detecting the presence of autoantibody biomarkers associated with a risk of ovarian cancer recurrence. Each of the polypeptide marker antigens specifically binds to at least one autoantibody biomarker. The present invention also provides an antibody binding assay for detecting the presence of autoantibody biomarkers associated with a risk of ovarian cancer recurrence. The present invention further provides a method for detecting the presence of autoantibody biomarkers associated with the recurrence of ovarian cancer. The present invention still further provides a method for determining a risk of ovarian cancer recurrence in an ovarian cancer patient. The present invention also provides a method for treating ovarian cancer recurrence in an ovarian cancer patient on the basis of the determined risk of recurrence. The present invention further provides a method for isolating antibodies that bind specifically to epitopes of ovarian cancer tissue or ovarian cancer associated tissue, the antibodies being isolated on the basis of their affinity to the polypeptide maker antigens of the present invention. The present invention still further provides antibodies isolated on the basis of their affinity to the polypeptide marker antigens.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 6A-6L are western blot images showing reactivity of antigens with serum samples obtained from ovarian cancer patients at 3 different time points and women with other benign diseases and healthy women, FIG. 6A is patient P265, FIG. 6B is patient P178, FIG. 6C is patient P410, FIG. 6D is patient P370, FIG. 6E is patient P326, FIG. 6F is patient P367, FIG. 6G is patient P413, FIG. 6H is patient P341, FIG. 6I is patient P398, FIG. 6J is patient P393, and FIGS. 6K and 6L are benign and healthy patients;

DETAILED DESCRIPTION OF THE INVENTION

Figure 1A:
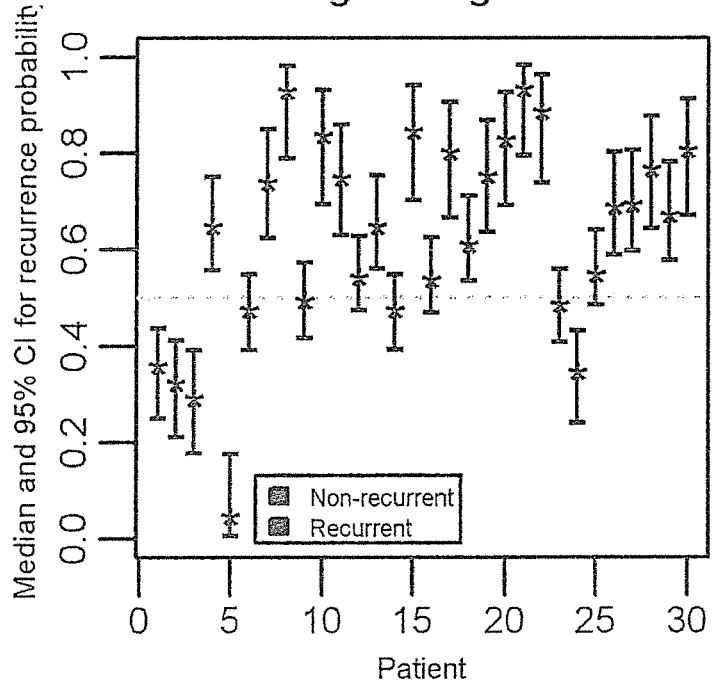
FIG. 1A shows a determination of median and 95% confidence interval of the predicted probability of recurrence of each ovarian cancer patient, based on the performance of polypeptide marker antigen Mec1_4B7, using logistic regression bootstrapped algorithm.

The present invention provides isolated polypeptide marker antigens and methods for their use in predicting and detecting recurrence of ovarian cancer (OVCA). The isolated polypeptide marker antigens are shown to bind specifically to autoantibody biomarkers whose presence in a patient body fluid is associated with the recurrence of OVCA after treatment. The detection of autoantibody biomarkers by their binding to the polypeptide marker antigens is the basis for new tools and methods for determining risk of recurrence, and for earlier detection of recurrence, because the autoantibody biomarkers are present and detectable prior to the presence of symptoms. The determination of risk of recurrence prior to the presence of symptoms in turn enables a method of treatment of recurrent OVCA in which the treatment is administered on the basis of the risk rather than symptoms. Most preferably, the polypeptide marker antigens are paraneoplastic antigens shown in SEQ ID NO: 23, SEQ ID NO: 25, and SEQ ID NO: 27.

In the following description, the term "recurrence of OVCA" refers to the return of ovarian cancer after treatment, and usually after a period of time during which the cancer cannot be detected. The term "risk of OVCA" refers to both a probability that OVCA will recur in the future and to an actual recurrence of OVCA, such as a subclinical recurrence. The term "biomarker" is defined as a biological molecule found in blood and other body tissues that is an indication of a condition or disease. The term "biomarker autoantibody" is used to indicate autoantibodies associated with the risk of OVCA recurrence. The terms "marker antigen" and "polypeptide marker antigen" refer to a reagent that specifically and detectably binds to at least one patient autoantibody.

The isolated polypeptide marker antigens included in the present invention were discovered through use of the robust method of "epitomics" (16 and U.S. Pat. No. 7,863,004). Epitomics entails the high-throughput cloning of cellular and random polypeptide antigens; the biopanning of patient and control sera against the cloned polypeptides, to discover candidate antigens specifically reactive with disease-associated antibodies; and polypeptide microarray-based serological screening to validate the disease association of the candidate antigen-antibody combinations. More specifically, the polypeptide marker antigens of the present invention were discovered in a study evaluating antigens potentially useful in predicting recurrence in OVCA patients, with a special focus on patients who express CA125 within the normal range (<35 U/ml) and therefore would not be considered by CA125 testing to be at risk of OVCA recurrence. This is a critical patient population, because no biomarker-based or other assays, other than CA125, are currently available to monitor the course of the disease during or after primary chemotherapy treatment. Antibody binding assays including one or more of the ten marker antigens of the present invention can be used to distinguish recurrent from non-recurrent OVCA patients at a median time of 9.07 months prior to clinical recurrence.

It was confirmed that the isolated polypeptide marker antigens of the present invention are useful in detecting autoantibody biomarkers that predict OVCA recurrence prior to the rise in CA125. The predictive value of the panel of ten marker antigens was proven in a sample population of ovarian cancer patients by statistical analyses including logistic regression and classification and regression trees (CART), as detailed in Example 1. The top three marker antigens, SEQ ID NOS: 1, 2, and 3, discriminated between recurrent and nonrecurrent patients with an average sensitivity, specificity and accuracy of 94.7%, 86.7% and 93.3% respectively. Taken as a whole, the panel of ten marker antigens discriminated between recurrent and nonrecurrent patients with an average sensitivity, specificity, and accuracy of 74.8%, 96.0% and 78.3% respectively. These average sensitivity and accuracy values are superior to those determined for immunoassays of the biomarker CA125. The CA125 immunoassays showed a sensitivity and accuracy of 8.0%, and 30.4%, respectively. In Receiver Operating Characteristic Curve (ROC) analyses, as described in Example 1, assays employing each of 10 marker antigens individually displayed area under the curve (AUC) values greater than the value found for immunoassays of the well-known tumor antigen p53. Thus, each of the ten marker antigens is a valuable individual predictor of OVCA recurrence. In Example 2, additional markers of paraneoplastic antigens (HARS (SEQ ID NO: 23), CDR2 (SEQ ID NO: 27), Ro52 (SEQ ID NO: 25)) (also in combination with several of the markers from Example 1) were shown to predict recurrence in ovarian cancer patients 5.03 months before clinical or symptomatic relapse with a sensitivity of 90.5% when CA125 levels were below the standard cutoff (35 U/ml). Specific combinations of the paraneoplastic antigens can be used with the markers antigens in SEQ ID NOS: 1-10. For example, HARS, CDR2, and Ro52 can be particularly useful in combination with 5H6 (SEQ ID NO: 3). However, it should be understood that any combination of the marker antigens described herein can be used either alone or in combination in any of the panels, assays, or methods described herein. In addition, the polypeptide marker antigens and subsets thereof are useful as an integrated panel of predictors of OVCA recurrence that is more diverse, and thus more likely to detect rare biomarkers of recurrence, than any single individual marker.

The isolated polypeptide marker antigens of the present invention are useful in antibody binding assays, in which the presence of recurrence-indicating autoantibody biomarkers is detected by their binding to the polypeptide marker antigens. It is likely that the polypeptide marker antigens include epitopes or mimotopes of the original antigens that elicited the production of the patient autoantibody biomarkers. The identification of the original antigens, or the characterization of the patient autoantibodies, is not necessary for the usefulness of the polypeptide marker antigens. The presence of the autoantibody biomarkers alone indicates a risk of OVCA recurrence.

The marker antigens are preferably employed in the form of polypeptides displayed on the surface of bacteriophages in a bacteriophage display system. The usefulness of the polypeptide marker antigens is not limited to the bacteriophage context. They can also be employed as isolated, purified polypeptides. The term "purified" refers to material that is substantially or essentially free from components that normally accompany it as found in its native state. Purity and homogeneity are typically determined using analytical chemistry techniques such as polyacrylamide gel electrophoresis or high performance liquid chromatography. A protein or peptide that is the predominant species present in a preparation is substantially purified. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

The preferred bacteriophage display system is the T7 bacteriophage, most preferably the T7 Select® system available from Novagen (EMD Bioscience Inc.: Novagen, San Diego, Calif., USA). Populations of phage expressing and displaying a single marker peptide of the present invention can readily be generated through the insertion of appropriate polypeptide-encoding cDNAs into the phage genome by well-known methods for insertion and for verifying that the correct DNA sequence has been inserted (e.g. Novagen T7 Select® Manual, User Protocol TB178 Rev. D 0311JN, which is also a source of methods for phage amplification). An exemplary method for the PCR amplification and sequencing of inserts in a bacteriophage expression system is found in U.S. Pat. No. 7,964,536, which is incorporated herein by reference in its entirety, at column 37, lines 45-57.

Phage display clones expressing the polypeptide marker antigens of the present invention can readily be generated by one ordinarily skilled in the art of phage display. For example, a clone of T7 bacteriophage expressing a marker antigens of SEQ ID NO: 1 can be generated by synthesizing any cDNA encoding a polypeptide of SEQ ID NO: 1, cloning the cDNA into T7 bacteriophage, cloning the bacteriophage, expanding the clones, and verifying the sequence of the insert in at least one clone. Standard techniques for these procedures are readily available in manuals such as Novagen T7 Select Manual, User Protocol TB178 Rev. D 0311JN.

The isolated polypeptide marker antigens of the present invention can also be obtained by recombinant techniques. Vectors, cloning methods, and purification techniques are readily selected by a skilled artisan from standard laboratory manuals, such as references (51) and (52). For example, a plasmid vector including a polynucleotide encoding a marker antigen, and linked to an appropriate promoter, can be transfected into a host cell line in a calcium phosphate precipitate or charged lipid complex. A viral vector can be packaged in vitro using an appropriate packaging cell line and transduced into a host cell line. The polypeptide marker antigens of this invention can be recovered and purified from recombinant cell cultures by well-known methods including ammonium sulfate or ethanol precipitation, acid extraction, anionic or cationic exchange chromatography, phosphocellulose chromatography, chromatography, and chromatography on hydroxyapatite or affinity columns. High performance liquid chromatography ("HPLC") or affinity purification of a tagged recombinant polypeptide are preferable techniques for purification.

For the detection of the presence of autoantibody biomarkers associated with recurrence of OVCA, the isolated polypeptide marker antigens are preferably spotted or otherwise immobilized on a solid substrate for use in an antibody binding assay. The polypeptide marker antigens serve as capture reagents to bind specifically to patient autoantibody biomarkers. The polypeptide marker antigens can be immobilized in an array including multiple marker antigens, or can be displayed singly, or in any desired configuration. The substrate is preferably a nitrocellulose membrane or a slide coated with nitrocellulose or a nitrocellulose-based polymer. Alternatively, any suitable alternative substrates known in the art can be employed, including a glass, silicon, or plastic slide, a filter, a biochip including signal transducing electronics, an ELISA plate, and a spinning interferometry disc (53). Particulate substrates can also be utilized, for example as fluorescent or nonfluorescent, polystyrene beads and peptide-binding microspheres (54). An advantage of nitrocellulose membranes is that a multiplicity of markers can be deposited in regular arrays by robotic methods, allowing the testing of serum samples against many markers at once; and that many membranes can be simultaneously processed and analyzed for binding of autoantibody biomarkers. It will be understood that all arrays and other arrangements of marker antigen immunoassays must be created in multiple replicates as required for appropriate statistical analysis of results.

Preferably, arrays including the isolated polypeptide marker antigens also include negative control proteins to permit compensation for the nonspecific binding of antibodies via physical or electrostatic interaction. For example, bacteriophage expressing irrelevant peptides, or no inserted peptides, can be employed as negative control antigens. Where the polypeptide marker antigens are employed as purified peptides, irrelevant peptides are suitable negative controls.

In an antibody binding assay employing an array of polypeptide marker antigens and control antigens, the array is preferably blocked to minimize nonspecific binding of antibodies. The array is then exposed to a body fluid, preferably serum, of a patient being assessed for risk of cancer recurrence. Although serum is preferred, any body fluid known in the art to contain antibodies can be employed, for example plasma, blood, saliva, tears, and spinal fluid. Replicate arrays are exposed to suitable control sera. Negative control sera can comprise the sera of normal single or pooled individuals, single or pooled patients who did not experience recurrence, or mixtures of normal and nonrecurrent sera, with the sera being selected and prepared by means well-known in the art. Positive control sera can include sera from patients undergoing OVCA recurrence. Preferably, sera from multiple OVCA patients is pooled, and the pool is verified to include a positive signal for each polypeptide marker antigen, that is, an autoantibody that binds to each polypeptide marker antigen employed in the array. Alternatively, positive control human monoclonal antibodies can be developed from OVCA patient B cells or from immunoglobulin libraries developed from those cells. Screening of clones of hybridomas or other expressing cell types can be accomplished by assay of the binding of secreted antibodies to the polypeptide markers of the present invention. This approach has the advantage of providing a consistent and limitless supply of positive control antibodies.

Once serum autoantibody biomarkers have been allowed to bind to the marker antigens, the arrays are washed and the presence of specifically bound antibody is indicated and quantitated by means of a signal generating system.

Preferably, the signal generating system is a dual fluorescence system. A typical suitable system includes, a biomarker-binding antibody, that is, an antibody recognizing an autoantibody biomarker that has been bound by a polypeptide marker antigen. The dual fluorescence system also includes a normalization reagent that recognizes a non-antibody binding moiety of the polypeptide marker antigen, for example a constant capsid protein of a phage particle displaying the marker antigen. The signal produced by the normalization reagent permits the correction of the autoantibody biomarker binding results for the amount of marker antigen available to bind the autoantibody biomarker. The biomarker-binding antibody is coupled directly or indirectly to a first fluorescence label, and the normalizing reagent is coupled directly or indirectly to a second fluorescence label. In an exemplary phage display detection system, an anti-human immunoglobulin (Ig) antibody coupled to the fluorescent dye Cy5 produces a red fluorescence signal that is used to quantitate an autoantibody biomarker bound to a marker antigen. An anti-phage capsid antibody coupled to Cy3 produces a green fluorescence signal that is used to normalize the red fluorescence according to the quantity of display phage capsids present in the assay. Coupling of the antibodies to fluorescent dyes can be accomplished by chemical conjugation or by use of a labeled secondary antibody. Antigen binding assays according to the present invention can also be performed with only a biomarker-binding antibody or other biomarker-binding reagent, without normalization.

An exemplary assay for the binding of serum antibodies to phage-displayed peptide antigens is disclosed in the publication by Chatterjee et al. (17). Briefly, phage clones displaying polypeptide antigens are amplified in $E.$ $coli$ and prepared as bacterial lysates by well-known techniques such as those described in Novagen T7 Select® Manual, User Protocol TB178 Rev. D 0311JN. Phage lysates at suitable titers, are spotted in quintuplicate onto FAST slides (Schleicher & Schuell, Keene, N H) by a robotic microarrayer, Prosys5510TL (Cartesian, Inc., Ann Arbor, Mich.). T7 monoclonal antibody (Novagen) and goat anti-human IgG (Pierce) are labeled with monofunctional NHS ester-activated Cy3 and Cy5 dyes, respectively, following the manufacturer's instructions (Amersham Biosciences Corp., Piscataway, N.J.). Human serum to be assayed can contain anti-$E.$ $coli$ antibodies which can react with traces of $E.$ $coli$ proteins in the phage lysate. In order to block anti-$E.$ $coli$ antibodies, serum samples are preferably pretreated with 150 µg of bacterial extract for 1 h at room temperature The slides are blocked in 4% milk/PBS/0.1% Tween 20 for 1 hour at room temperature and incubated with human serum at a dilution of 1:300 in PBS at room temperature for 1 hour. The slides are rinsed in PBS and washed thrice in PBS/0.1% Tween 20 for 10 minutes each at room temperature and then incubated with Cy3-labeled-T7 anti-capsid antibody at a dilution of 1:70,000 and anti-human IgG labeled with Cy5 at a dilution of 1:3,000 in PBS for 1 hour in the dark. The slides are washed thrice in PBS/0.1% Tween 20 for 2 minutes each and then twice in PBS for 2 minutes each and air dried. The slides are scanned in an Axon Laboratories 4100A scanner (Palo Alto, Calif.) using 532 and 635 nm lasers. The ratio of anti-T7 capsid and antihuman IgG is determined by comparing the fluorescence intensities in the Cy3- and Cy5-specific channels at each spot using ImaGene software (Biodiscovery, Inc., El Segundo, Calif.)

Alternatively, any suitable signal generating system known in the art can be employed to detect and quantitate the binding of an autoantibody biomarker to a marker antigen, with the signal generating system including at least one label component which generates a detectable signal relating to the amount of antibody bound to a marker antigen. The label can be any molecule that produces or can be induced to produce a signal, such as a fluorophore, an enzyme, a chemiluminescent molecule, or a photosensitizer. Thus, the signal is detected and/or measured by detecting fluorescence, enzyme activity, luminescence, or light absorbance. Suitable labels include, by way of illustration and not limitation, enzymes such as alkaline phosphatase, glucose-6-phosphate dehydrogenase ("G6PDH") and horseradish peroxidase; ribozyme; a substrate for a replicase such as Q-beta replicase; promoters; dyes; fluorescers such as fluorescein, isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; photosensitizers; particles such as latex or carbon particles; suspendable particles; metal sol; crystallite; liposomes; cells, etc., which can be further labeled with a dye, catalyst, or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescent or chemiluminescent molecules are disclosed in Litman, et al., U.S. Pat. No. 4,275,149, at columns 30 and 31; which are incorporated herein by reference.

The signals produced by the binding of autoantibody biomarkers to the isolated polypeptide marker antigens and controls are analyzed with a signal analysis system to determine the amount of autoantibody biomarker that has bound specifically to each marker antigen, especially with regard to whether the binding is higher than nonspecific background binding. The results can, for example, be in the form of absolute or relative fluorescence values, or in the form of amounts of bound antibody as determined according to a standard curve. Preferably, the analysis is automated. Exemplary automated signal analysis devices and analysis software packages include, but are not limited to the Odyssey® imaging system (LI-COR Biosciences, Lincoln, Nebr.), and the previously mentioned Axon Laboratories 4100A scanner, both of which can be employed in conjunction with ImaGene software (Biodiscovery, Inc., El Segundo, Calif.).

The results of the antibody binding assay are preferably interpreted by comparing fluorescence or other signal values to calibration curves of signal values obtained by exposure of the marker antigens to standard control sera. Sera from normal individuals, recurrent OVCA patients, and nonrecurrent OVCA patients, preferably in the form of pooled sera from multiple individuals, are appropriate standards for the calibration of assays of serum autoantibodies predictive of recurrence. The standards are used to construct standard calibration curves by methods well-known in the art. Example protocols for the use of such standards are readily available in reference (55).

An exemplary phage display system for the expression of the isolated polypeptide marker antigens of the present invention is the T7 isocahedral phage display system, as described in Example 1 and in U.S. Pat. No. 7,964,536. The present invention is not limited to the T7 system. Any phage display system that can express polypeptides can alternatively be used, including other isocahedral phages such as T4, and filamentous phages such as M13, fd, and fl (56). In Example 1, the autoantibody biomarkers detected are of the human IgG class, but there is no indication that autoantibodies indicative of OVCA recurrence risk should be limited to that Ig class or to human cases. The T7 and other phage display systems are capable of displaying antigens that specifically bind particular paratopes of IgA, IgE, and IgM antibodies, in both human and nonhuman systems (57-59).

The isolated polypeptide marker antigens of the present invention enable a user to determine whether an OVCA patient is at risk of disease recurrence after a first line ovarian cancer treatment. It is likely that patients determined to be at risk of recurrence by the present invention are already undergoing recurrence in the form of subclinical tumor. It is also possible that no recurrence has yet occurred, and that one or marker antigens of the present invention is detecting an autoantibody biomarker induced by a risk-associated antigen of the original tumor. A method according to the present invention includes the steps of collecting a sample of a body fluid from an ovarian cancer patient; exposing the sample of a body fluid to one or more polypeptide marker antigens selected from SEQ ID NO: 23 (HARS), SEQ ID NO: 25 (Ro52), and SEQ ID NO: 27 (CDR2), and optionally at least one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10; quantitating the specific binding of an autoantibody biomarker by the polypeptide marker antigen; detecting the presence of the autoantibody biomarker in the sample of body fluid; and determining that the ovarian cancer patient is at risk of ovarian cancer recurrence. The preferred body fluid is serum, and collection can be made following a first-line treatment or a later course of treatment; during a course of treatment; or prior to any treatment.

When patients are determined to be undergoing recurrence, the present invention includes a method of treatment of recurrence directed selectively to the patients at risk. The method includes the administration of treatment in addition to, or instead of, the appropriate first-line therapy for these patients. One mode of additional treatment is the initiation of second-line ovarian cancer therapy. Second-line therapies are well known in the art. They include, but are not limited to, combinations of platinum and taxanes. If the disease has become refractory, second line therapies can include topotecan, gemcitabine, paclitaxel, inhibitors of vascular endothelial growth factor (VEGF) such as bevacizumab, epidermal growth factor receptor (EGFR) inhibitors such as erlotinib, and poly (adenosine diphosphateribose) polymerase (PARP) inhibitors. (60) In cases in which more than two courses of treatment are possible, the terms "first-line" and "second-line" can be used in a relative sense, with the terms "first-line" denoting an earlier treatment and "second-line" denoting any treatment following the earlier treatment. Other possible treatments for recurrent OVCA include prolonging first-line treatment beyond its initially planned course, and initiating maintenance treatments according to appropriate maintenance protocols current in the art.

The method of the present invention is not limited to assessing risk of recurrence during a period following completion of first-line treatment, and in patients who have responded to that treatment. The method can also be employed while first-line treatment is still in progress, and can be applied to patients not necessarily showing a response to that treatment.

The isolated polypeptide markers of the present invention equip a clinician with a new tool for directing second-line OVCA treatment to the patients who are most at risk of recurrence, and who stand to benefit the most from the treatment, while withholding treatment, and its attendant side effects, from patients who would not benefit from it. A final decision as to whether further treatment should be initiated is of course made by a clinician on the basis of many factors, such as treatment history, the side effects of further treatments, and the health and level of function of the patient. The polypeptide marker antigens and methods of the present invention provide a clinician with an important new factor to consider in making the final decision.

Also included in the present invention is a method for isolating antibodies for the detection and targeting of OVCA on the basis of their affinities to the isolated polypeptide marker antigens of the present invention. The present invention also includes the detecting and targeting antibodies isolated by this method. It is likely that the autoantibody biomarkers detected by the polypeptide marker antigens of the present invention were originally induced by epitopes of ovarian tumor or of tumor-associated tissue such as abnormal stroma. It is therefore likely that antibodies that bind specifically to the polypeptide marker antigens will also bind specifically to tumor or tumor associated tissue in vivo or in vitro. For example, a series of monoclonal antibodies can be screened against the polypeptide marker antigens of the present invention. Antibodies specifically reactive to one or more of the polypeptide marker antigens can be identified by well known hybridoma screening methods such as those described in reference (61), pp 174-195. The hybridomas that produced the reactive monoclonal antibodies can then be isolated and use in the production of ovarian cancer detecting and targeting antibodies. In another example, an affinity column or other affinity medium can incorporate the polypeptide marker antigens of the present invention. The column can be exposed to a pool of mixed antibodies, and washed to remove nonbinding and nonspecifically bound antibodies. Specifically bound antibodies can be eluted and identified as ovarian cancer detecting and targeting antibodies. It will be understood that these examples are not limiting, and that the polypeptide marker antigens of the present invention can be used with many other antibody screening methods. Such methods are readily selected and employed by those skilled in the art, from references such as reference (61), pp. 421-467 and 511-552. The antibodies isolated by means of the present invention can be modified to include labels, immunostimulants, and toxic moieties, or can have direct toxic effects, for example by triggering apoptosis or blocking stimulatory receptors.

Example 1: Detection of Tumor Autoantibody Biomarkers for Predicting Ovarian Cancer Recurrence Materials and Methods Study Population.

Patients diagnosed and treated for late stage serous OVCA at Karmanos Cancer Institute or St. John Hospital & Medical Center (Detroit, Mich.) or Oakwood Hospital & Medical Center (Dearborn, Mich.) were entered onto the study at the time of their diagnosis or during a return visit within 5 years of initial diagnosis. Medical records were reviewed to determine CA125 levels, disease status, chemotherapy status, and time to recurrence (TTR) over a multi-year period. Cases were limited to those diagnosed between 1997 and 2007 to ensure sufficient follow up. On the basis of this information patients were divided into two groups: 1) No Recurrence (NR), defined as no clinical evidence of disease for at least 48 months, and 2) Recurrent Disease (R), defined as clinical evidence of disease and/or doubling of CA125 within approximately 3 years of diagnosis (range 11-39 months). Recurrent disease patients selected for the validation set had a disease-free interval of at least six months (range 6.6-34).

Serum Sample Collection and Processing.

Serum was collected and processed described in a previous study (17). Serum samples were selected for use on the basis of time since diagnosis, CA125 level, disease status, and chemotherapy status at the time of blood collection. For the initial study specimens from three time points were used for all cases (R and NR); the specimen obtained at time of enrollment and at two post-diagnosis intervals, which are given for each patient.

For the validation study, serum samples were collected from recurrent cases at a median time of 9.07 months (range=2.1 to 18.9 months) prior to clinical recurrence. Most patients had a normal CA125 and no clinical evidence of disease at that time. For nonrecurrent cases, samples were collected at least 11 months after completion of chemotherapy, with no evidence of disease and a normal CA125 level.

Study procedures were approved by the Wayne State University, St. John Hospital & Medical Center, and Oakwood Hospital & Medical Center Institutional Review Boards. All participants provided written informed consent.

Serological Screening of Polypeptide Antigen Arrays.

Peptide arrays were prepared by amplifying 174 individual antigen-expressing T7 phage clones (initial study) and 56 individual antigen-expressing T7 phage clones (validation study), and arraying their lysates onto a nitrocellulose membrane using the Beckman Biomek 2000® liquid handling robot. This robot, equipped with a 96-pin printing head, spotted the bacteriophage samples contained in 96 well plates onto nitrocellulose membranes in a 4×4 pattern. Empty phage vectors were used as negative controls in both the initial and validation studies. The nitrocellulose membranes were blocked with 5% dry milk for 1 h at room temperature. For the initial serological screening, the blocked nitrocellulose membranes (arrays) were processed with serum samples that were obtained from recurrent (n=5) and non-recurrent (n=5) OVCA patients. For the validation study, the blocked membranes were processed with samples from the initial study (see above) along with serum samples obtained from independent cohorts comprised of recurrent (n=25) and non-recurrent (n=5) OVCA patients. In order to block anti-E. coli antibodies, serum samples were pretreated with 150 μg of bacterial extract for 1 h at room temperature.

For the initial antigen selection serological study and the validation study, 1:100 serum dilution was used. The membranes were washed three times with 0.24% Tris, 0.8% NaCl, 1% Tween-20 (TBST) for 10 min each and incubated with rabbit-anti human secondary antibody conjugated with IR-Dye800 (Rockland, Gilbertville, Pa., USA) at 1:5000 dilution for 1 h at room temperature. The membranes were then washed three times with TBST for 10 min each, and two times with 1×PBS for 5 min each. The arrays were scanned using an Odyssey® imaging system at 800 nm wavelength according to manufacturer's instructions. The fluorescence intensity at each spot was quantified using ImaGene software (Biodiscovery, Inc., El Segundo, Calif.). Nitrocellulose membranes (3 membranes for the initial study; 12 membranes for the validation study) were separately treated with mouse anti-T7 antibody directed toward T7 phage coat protein (EMD Bioscience Inc.: Novagen, San Diego, Calif., USA), exactly following the above procedure. Alexa Fluor 680 Goat anti-mouse IgG secondary antibody (Molecular Probes, Invitrogen, Grand Island, N.Y., USA) at 1:10000 dilution was used and the membranes were scanned using Odyssey® imaging system at a wavelength of 700. The quantified images were used for data normalization.

Statistical Analyses i) Background Correction and Normalization.

The following procedure was followed for both the initial and the validation study. The image quantified files were read into R using the Limma package suite of software. Any measurement with a "0" weight (defined as an empty or poor spot) was set to "missing". Each of the immunoassays (initial and validation study) was background corrected using the "minimum" method. That is, the background intensities were subtracted from the foreground intensities for each color channel [red (R) and green (G)]. Any resultant intensity that was zero or negative after the subtraction was set to half of the minimum of the positive corrected intensities from that channel. This created the signal intensity measurement for each assay. A normalization channel array was created using the point-wise median of the 1536 intensity values from the three assays (for initial study) and 12 assays (for validation study) performed with only with the anti-T7-capsid antibodies. Then each assay was normalized to this channel assay using the "median" method. That is, the log base 2 intensity ratio $M=\log(R/G)$ was computed for each assay. Then the median (M) was subtracted from all M values within the assay. Subsequently for each of the assays, the median corrected intensity measurement for each of the antigens was calculated, with each measure performed in triplicate on each assay. This dataset was used to conduct all of the analyses that are described in the Results section.

ii) Statistical Analyses for the Initial Study.

As this screening dataset had only 10 patients (5 recurrent, 5 non-recurrent), many different statistical methods were used to derive a list of polypeptide marker antigens to analyze in the set of patients in the validation experiment. The statistical methods used included t-tests and the Wilcoxon rank sum test (non-parametric analog to the t-test). Marker antigens that were significant at 0.05 for any of the three tests were retained for the validation study.

iii) Statistical Analyses for the Validation Study.

(a) CART.

Classification and Regression Trees (CART) is a form of binary recursive partitioning. The term 'binary" implies that each group of patients, represented by a "node" in a decision tree, can be split into 2 child nodes and the partitioning process can be repeated many times. CART identifies subset of the predictor (independent) variable(s) based on exhaustive search of all possibilities that best associate with the response variable. CART bootstrapped analysis was used in biomarker analysis to determine the significance of each measured antigen. A CART analysis was constructed on a bootstrapped training (or model building) dataset to identify thresholds for each antigen predicting cancer recurrence status. Next, the model was applied to a test dataset with no overlap of patients from the training dataset to determine if the antigens threshold model was predictive in a new dataset. This process was repeated many times. The 10 patients that were measured for the initial study were also measured in the validation study to validate the reproducibility of the marker antigen measurements in addition to the 30 new patient samples (25 recurrent, 5 non-recurrent). As the recurrent and non-recurrent sample sizes were quite different, weighted analyses were performed for the validation study. The nominal level of significance was determined using logistic regression, t-tests and Wilcoxon rank sum tests for each antigen for the 30 new patient samples. Bootstrapping was then used in conjunction with both logistic regression and classification and regression trees (CART) to evaluate if any of the polypeptide antigens were predictive of recurrence status. Briefly, a bootstrapped sample of 40 patients was created (ensuring that the 10 patients that were measured in the initial study were always in the training dataset). A prediction model was created (either a single antigen logistic regression or CART model) using the bootstrapped sample. The model was then applied to the holdout patient samples (not in the bootstrapped sample) and retained the predictive probability of recurrence. Over 10,000 bootstrapped samples, each of the new 30 patient samples was held out approximately 46% of the time. The predicted values for each polypeptide antigen were summarized for the pooled recurrent cases using the median and inter-quartile range (IQR). A similar summarization was done for the non-recurrent patients. Those polypeptide antigens for which the IQR was greater than 0.5 for the recurrent cases and less than 0.5 for the non-recurrent cases were deemed significant. Using the IQR instead of a confidence interval is necessary since individual patients may be poorly predicted; the IQR will yield polypeptide marker antigens that predict well over all samples. Individual plots of the 95% bootstrapped predicted confidence intervals were produced to determine which patients were poorly predicted by the model.

A CART model was also constructed for these selected antigens based on the test set of 30 samples. The results, in Table 1, demonstrate the results of the CART-selected threshold used as a predictor of recurrence status.

(b) Logistic Regression.

Logistic regression is a statistical method for modeling a binary endpoint (yes/no, recurrent/non-recurrent). In this model the response variable has only 2 values, typically denoted as 1 or 0. In a study of whether a patient recurs (y=1) or does not recur (y=0) after the front-line treatments, the probability of an event occurring is related to the predictor variable through the log it link function: $\log(p/(1-p))$; where p is the probability of recurrence. The exact statistical formulation of the model is $\log(p/1-p)=\beta_0+\beta_1 x$, where p is the probability of recurrence and x is the predictor variable.

In this study, using logistic regression, the reactivity of each polypeptide antigen from the learning dataset was used as the predictor variable to predict recurrence status. Similarly as described in the CART analysis, a logistic regression model for each antigen was then constructed on a bootstrapped sample of patient sample. The corresponding test data set was used as the model validation data set.

Results

The goal of this study was development of autoantibodies directed against TAAs as a potential prediction tool for detecting OVCA recurrence at an early time that could improve a clinician's ability to reimplement chemotherapy for a patient.

In an initial study, 174 polypeptide antigens known to bind serum autoantibodies of OVCA patients were tested for their ability to discriminate five recurrent OVCA patients from five nonrecurrent patients. Fifty-six of the polypeptide antigens showed significant discrimination as determined by statistical analyses including t-tests and the Wilcoxon rank sum test. This panel of 56 polypeptide antigens was entered into a validation study wherein they were tested on an expanded sample of OVCA patients and analyzed for ability to predict recurrence that is to serve as marker antigens by both CART and logistic regression analysis. In the validation study, the utility of the panel of 56 polypeptide antigens was compared to that of CA125 for predicting OVCA recurrence at a median time of 9.07 months (range=2.1 to 18.9 months) in a population where majority of patients showed recurrence without a rise in CA125 level.

Validation of Polypeptide Marker Antigens Biomarkers for Detection of Autoantibodies Associated with OVCA Recurrence at an Early Phase.

Serological immunoscreening of protein arrays was performed with serum obtained from an independent cohort of recurrent (n=25) and non-recurrent (n=5) OVCA patients as well as with serum samples used for the initial study. All the samples that were used for the initial study of antigen selection were only included in the training model and not used in the testing set during the validation process.

Figure 1B:
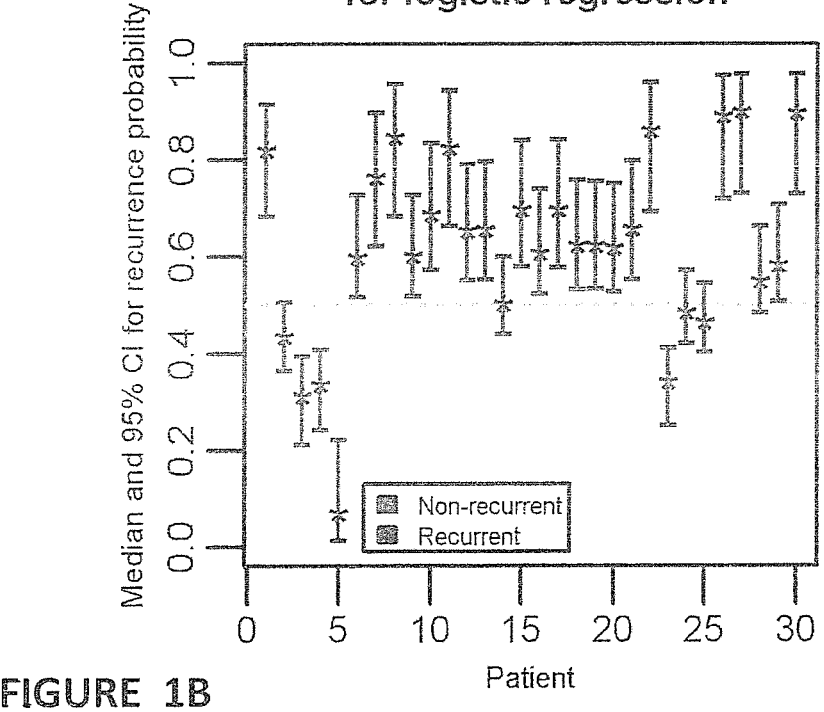
FIG. 1B shows a determination of median and 95% confidence interval of the predicted probability of recurrence of each ovarian cancer patient, based on the performance of polypeptide marker antigen Mec1_5H6, using logistic regression bootstrapped algorithm.
Figure 1C:
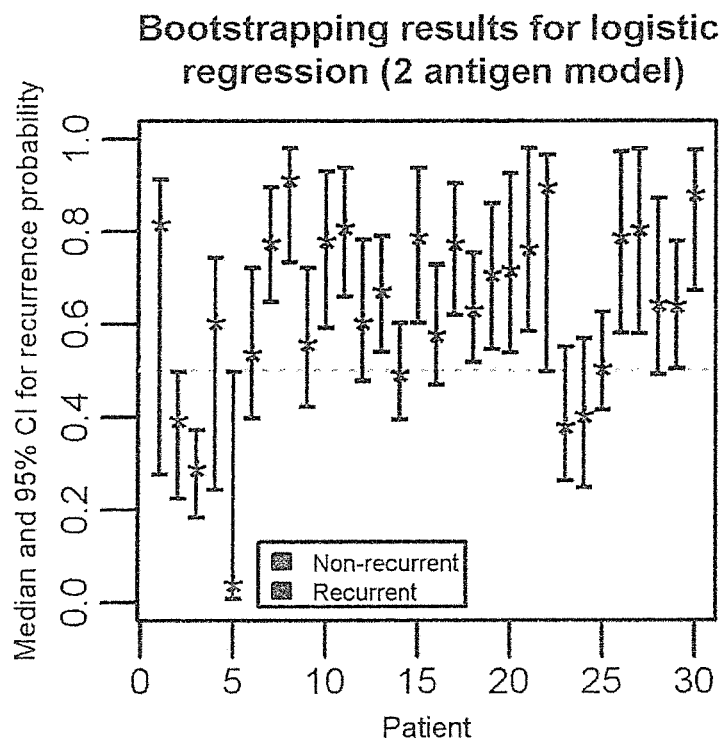
FIG. 1C shows a determination of median and 95% confidence interval of the predicted probability of recurrence of each ovarian cancer patient, based on the performance of the polypeptide marker antigens Mec1_4B7 and Mec1_5H6 in combination, using logistic regression bootstrapped algorithm.
Figure 2:
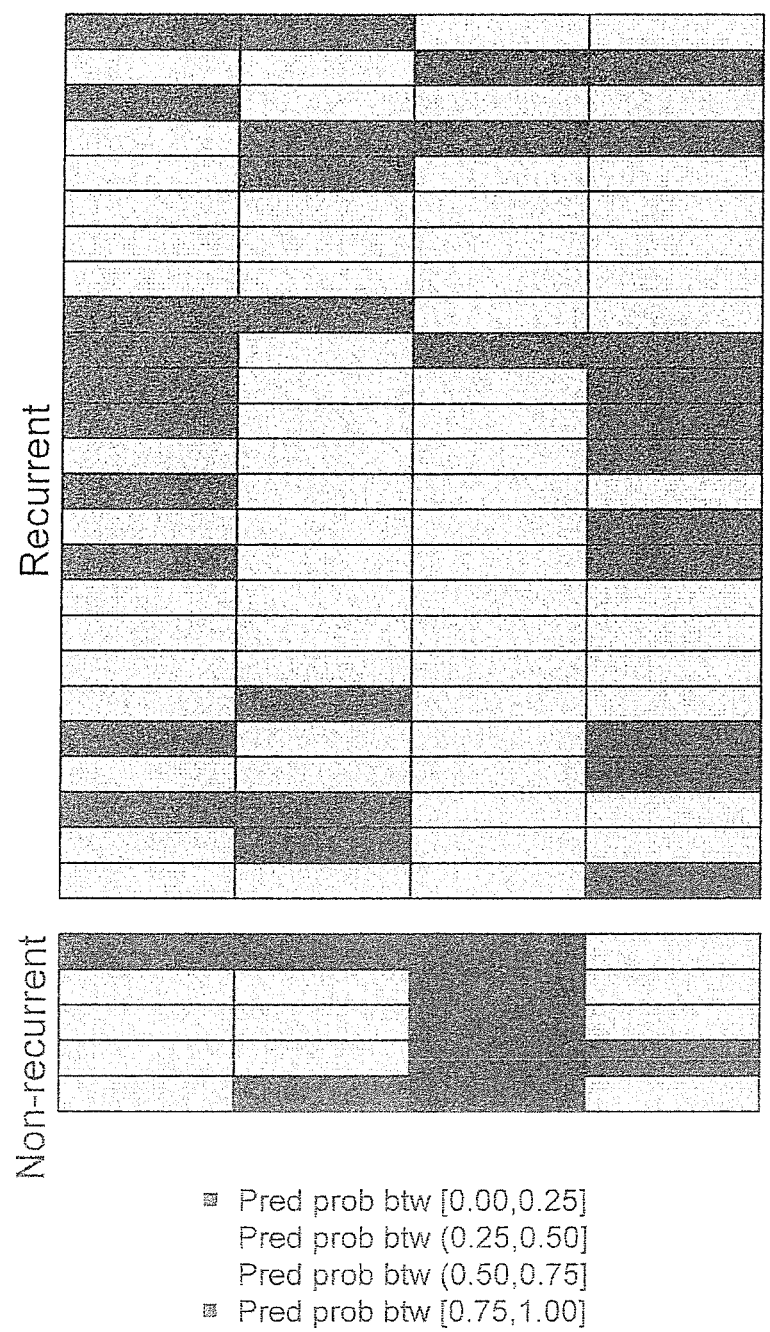
FIG. 2 shows a representation of predicted probability of recurrence of ovarian cancer patients based on the performance of each polypeptide marker antigen derived from bootstrapped samples, with the predicted probabilities for Mec1_4B7 and Mec1_5H6 computed as the median predicted value from the "testing set" from 10,000 bootstrapped logistic regression analyses (which always included the 10 samples previously used in the training set), and with predicted probabilities for Mec1_4H4 and p53 computed as the median predicted value from the "testing set" from 10,000 bootstrapped CART analyses (which always included the 10 samples previously used in the training set)

Using weighted logistic regression on the 30 newly measured patient samples, 28 polypeptide antigens proved statistically significant (p≤0.05) with respect to predicting recurrence status. Two of those antigens (Mec1_4B7, Mec1_5H6) were statistically significant using the bootstrapped algorithm. The median and pooled IQR values for Mec1_4B7 antigen were 0.695 (0.541, 0.817) and 0.322 (0.237, 0.399), and for Mec1_5H6 antigen were 0.652 (0.568, 0.774) and 0.352 (0.271, 0.456) for recurrent and non-recurrent cases respectively. The median and 95% confidence interval of the predicted probability of recurrence for each patient sample are shown in the FIGS. 1A and 1B. Only a few samples out of 30 for each antigen were poorly predicted. A rule of Mec1_4H4 or Mec1_4B7 would be accurate for all but 1 non-recurrent patient. A rule of Mec1_4H4 or Mec1_5H6 would be accurate for all but 1 non-recurrent patient (a different patient) (FIG. 2). Combining these polypeptide antigens in a single logistic regression model does not improve prediction (FIG. 1C).

Figure 1D:
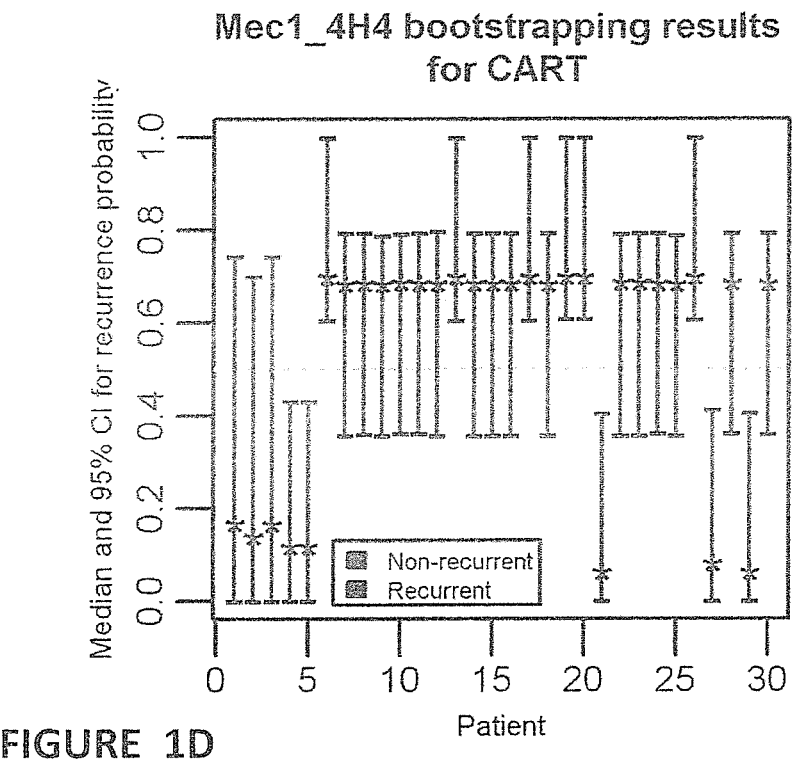
FIG. 1D shows a determination of median and 95% confidence interval of the predicted probability of recurrence of each ovarian cancer patient, based on the performance of the polypeptide marker antigen Mec1_4H4 (D), using CART bootstrapped algorithm.

There were 10 polypeptide antigens significant at 0.05 for either a t-test or a Wilcoxon rank sum test. CART was applied to these 13 antigens to determine the optimal threshold for determination of sensitivity and specificity as shown in Table 1. One antigen, Mec1_4H4, was found to be statistically significant using the CART bootstrapped algorithm. The median and pooled IQR for this antigen were 0.682 (0.620, 0.723) and 0.138 (0.067, 0.389) for recurrent and non-recurrent cases respectively. The median and 95% confidence interval of the predicted probability of recurrence for each patient sample are shown in FIG. 1D. Note that the confidence intervals are much wider for the CART analysis than the logistic regression analysis due to the categorization involved with CART. Only 3 recurrent patient samples had incorrect median recurrence probabilities.

the ROC curve (AUC) values for these seven marker antigens were found to range from 0.776-0.896 (Table 2). In

TABLE 1

The performance of 10 marker antigens obtained by CART analysis

| Antigen/threshold | TP | FN | FP | TN | Sensitivity | Specificity | PPV | NPV |
|---|---|---|---|---|---|---|---|---|
| Mec1_1B4 < 0.111 (SEQ ID NO: 4) | 15 | 10 | 0 | 5 | 60 | 100 | 100 | 33.3 |
| Mec1_2B3 >= −0.274 (SEQ ID NO: 5) | 17 | 8 | 0 | 5 | 68 | 100 | 100 | 38.5 |
| Mec1_2H1 < −0.122 (SEQ ID NO: 6) | 16 | 9 | 0 | 5 | 64 | 100 | 100 | 35.7 |
| Mec1_3D5T < 0.406 (SEQ ID NO: 7) | 15 | 10 | 0 | 5 | 60 | 100 | 100 | 33.3 |
| Mec1_3D7 >= −0.154 (SEQ ID NO: 8) | 17 | 8 | 0 | 5 | 68 | 100 | 100 | 38.5 |
| Mec1_4B7 >= −0.704 (SEQ ID NO: 1) | 25 | 0 | 1 | 4 | 100 | 80 | 96.2 | 100.0 |
| Mec1_4E8 < 0.112 (SEQ ID NO: 9) | 15 | 10 | 0 | 5 | 60 | 100 | 100 | 33.3 |
| Mec1_4H4 < 0.212 (SEQ ID NO: 2) | 22 | 3 | 0 | 5 | 88 | 100 | 100 | 62.5 |
| Mec1_5A3 >= −0.021 (SEQ ID NO: 10) | 21 | 4 | 0 | 5 | 84 | 100 | 100 | 55.6 |
| Mec1_5H6 >= −0.78 (SEQ ID NO: 3) | 24 | 1 | 1 | 4 | 96 | 80 | 96.0 | 80.0 |
| CA125 | 2 | 23 | 0 | 5 | 8 | 100 | 100 | 17.9 |

Figure 3:
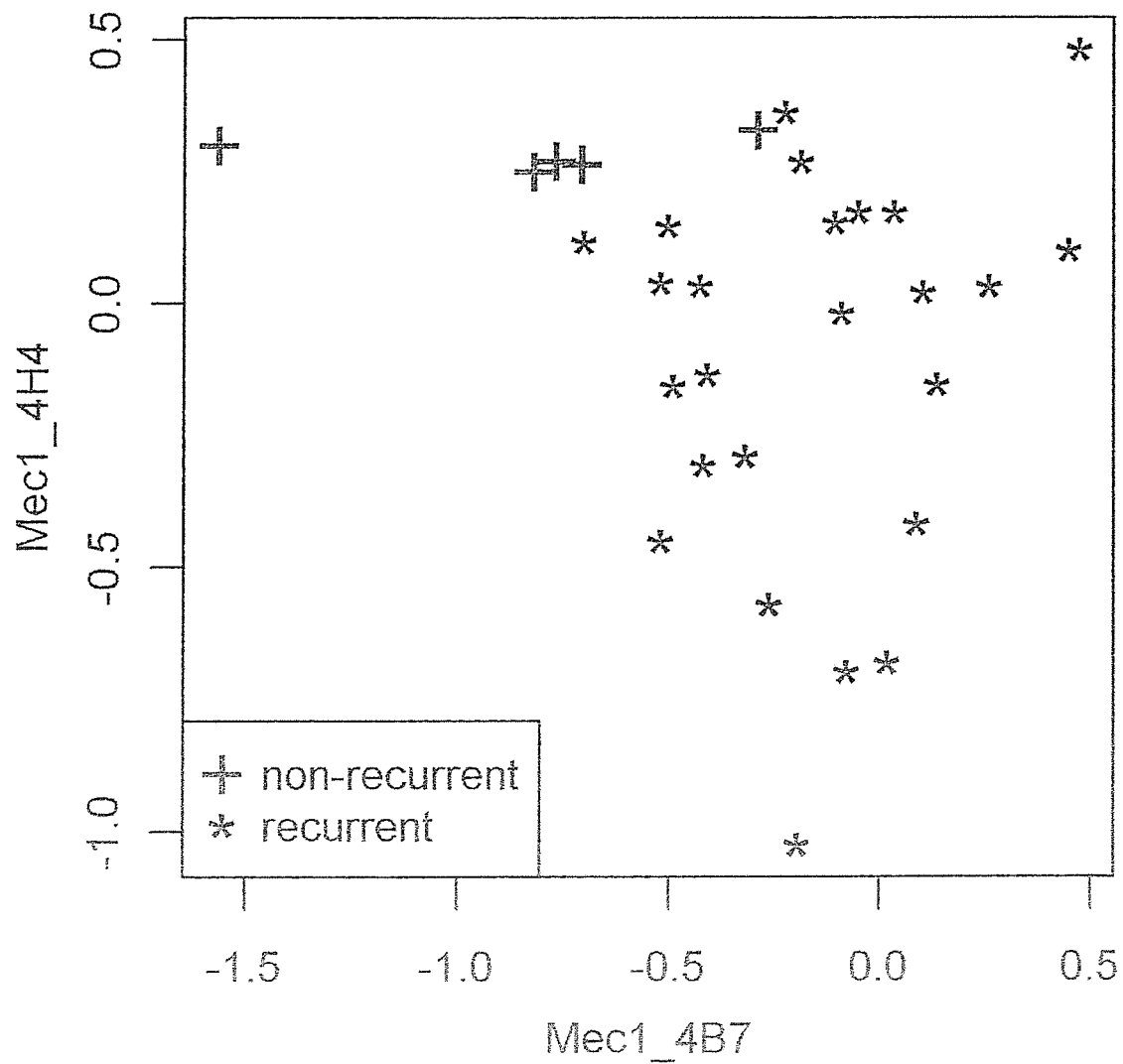
FIG. 3 shows a graphical representation of ovarian cancer validation set by recurrence status, based on correlation between 2 polypeptide marker antigens, Mec1_4B7 and Mec1_4H4.
Figure 4A:
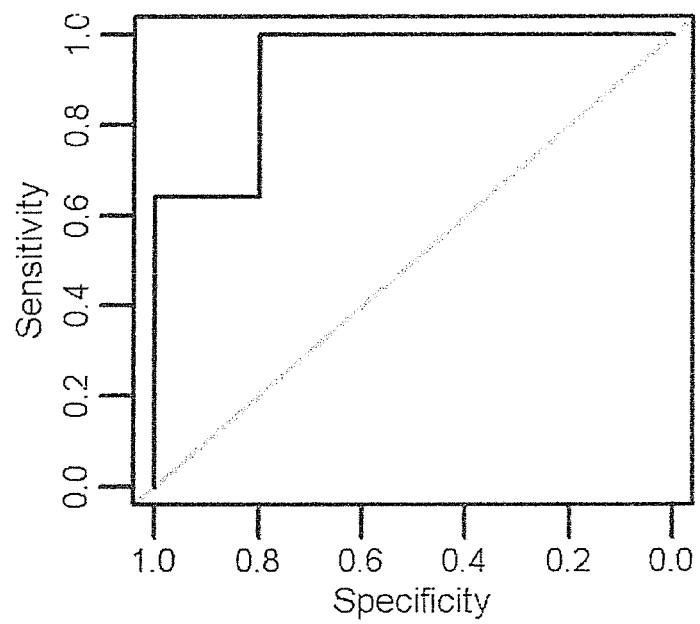
FIG. 4A shows the receiver operating characteristic (ROC) curve of the polypeptide marker antigen Mec1_4B7.
Figure 4B:
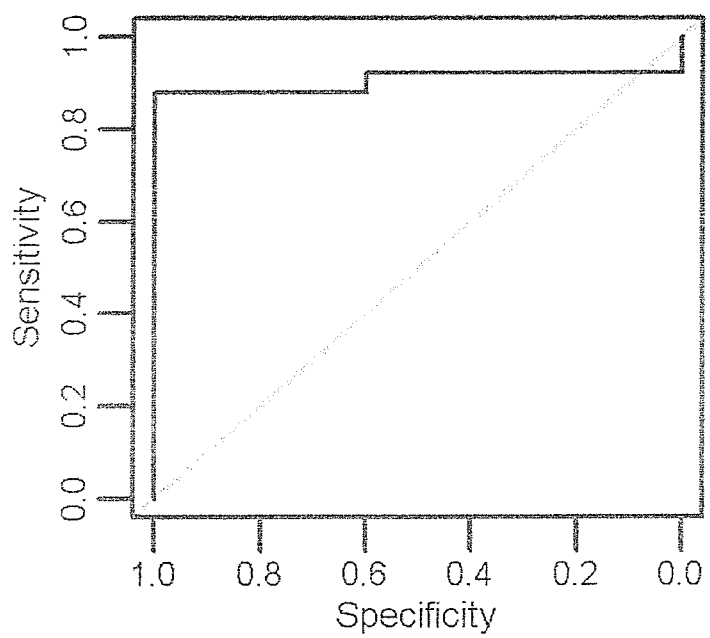
FIG. 4B shows the ROC curve of the polypeptide marker antigen Mec1_4H4.
Figure 4C:
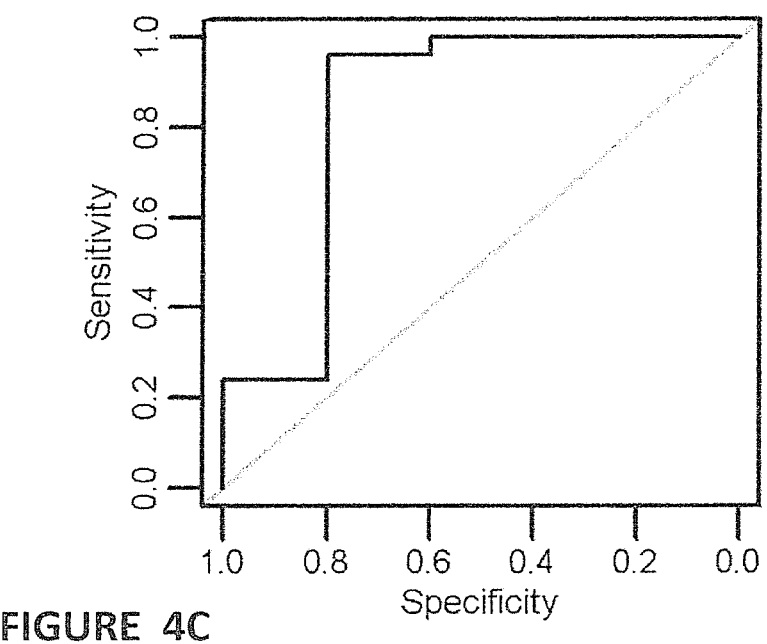
FIG. 4C shows the ROC curve of the polypeptide marker antigen Mec1_5H6.
Figure 4D:
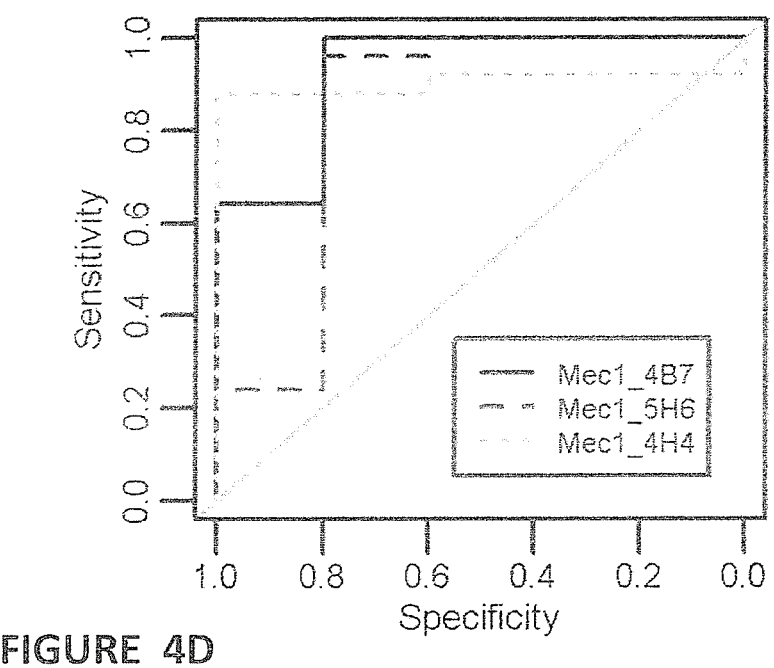
FIG. 4D shows a combination of the ROC curves of the polypeptide marker antigens Mec1_4B7, Mec1_4H4, and Mec1_5H6.

The 3 polypeptide antigens, Mec1_4B7, Mec1_4H4, and Mec1_5H6 that proved significant through either analysis were further examined. FIG. 3 shows the relationship between the 2 remaining antigens, Mec1_4B7 and Mec1_4H4 (after backwards step-wise selection on the 3 in a logistic regression model) and recurrence status of the validation samples. There is perfect non-linear discrimination between the recurrent and non-recurrent samples. The receiver operating characteristic (ROC) curves for each of the 3 polypeptide antigens are shown in FIGS. 4A-4C. The three lines are plotted on the same axis in FIG. 4D. The area under the curves (AUC) for Mec1_4B7, Mec1_4H4, and Mec1_5H6 were 0.928, 0.904 and 0.840 respectively (Table 2). The amino acid sequences of these three polypeptide antigens is given in Tables 4 and 5.

TABLE 2

The AUC values of 10 polypeptide marker antigens obtained by CART analysis

| Antigen | | AUC |
|---|---|---|
| Mec1_4B7 | (SEQ ID NO: 1)* | 0.928 |
| Mec1_4H4 | (SEQ ID NO: 2)* | 0.904 |
| Mec1_5H6 | (SEQ ID NO: 3)* | 0.840 |
| Mec1_1B4 | (SEQ ID NO: 4) | 0.792 |
| Mec1_2B3 | (SEQ ID NO: 5) | 0.792 |
| Mec1_2H1 | (SEQ ID NO: 6) | 0.776 |
| Mec1_3D5T | (SEQ ID NO: 7) | 0.832 |
| Mec1_3D7 | (SEQ ID NO: 8) | 0.872 |
| Mec1_4E8 | (SEQ ID NO: 9) | 0.744 |
| Mec1_5A3 | (SEQ ID NO: 10) | 0.896 |

Figure 4E:
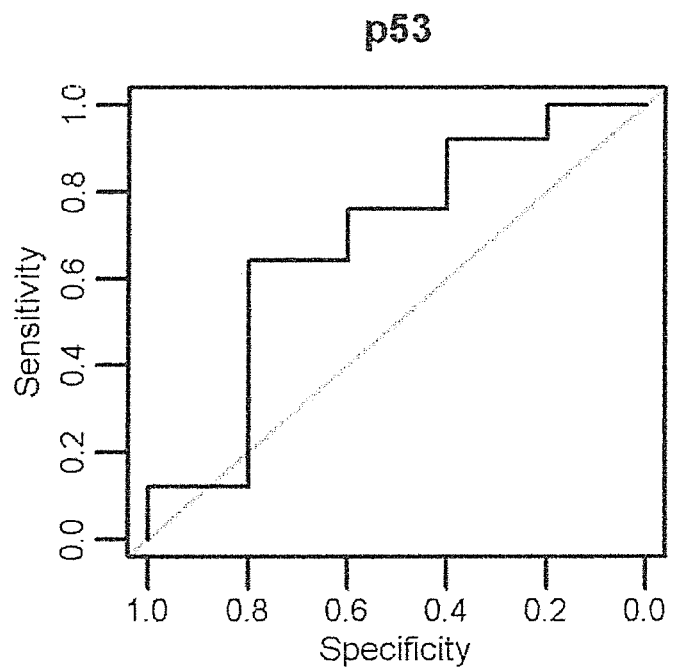
FIG. 4E shows the ROC curve of p53.
Figure 5A:
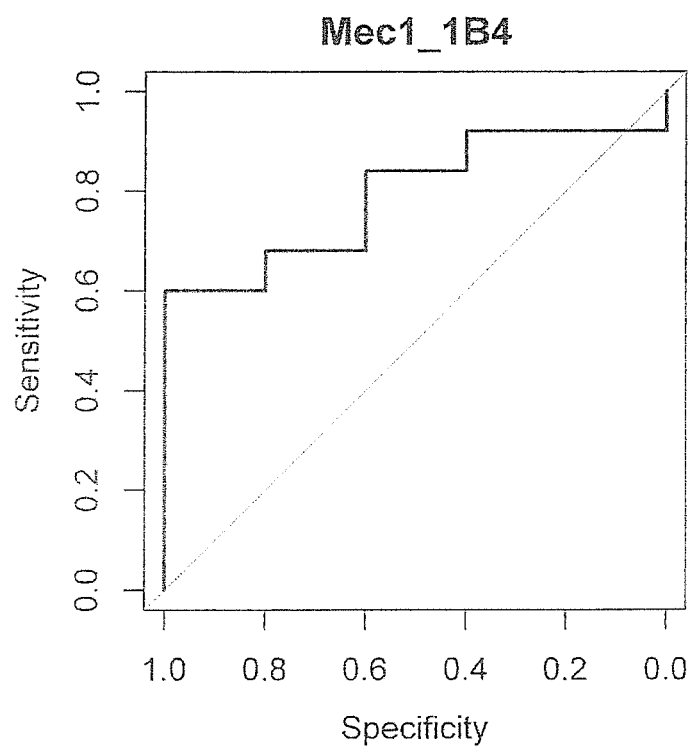
FIG. 5A shows the receiver operating characteristic (ROC) curve of the polypeptide marker antigen Mec1_1B4.
Figure 5B:
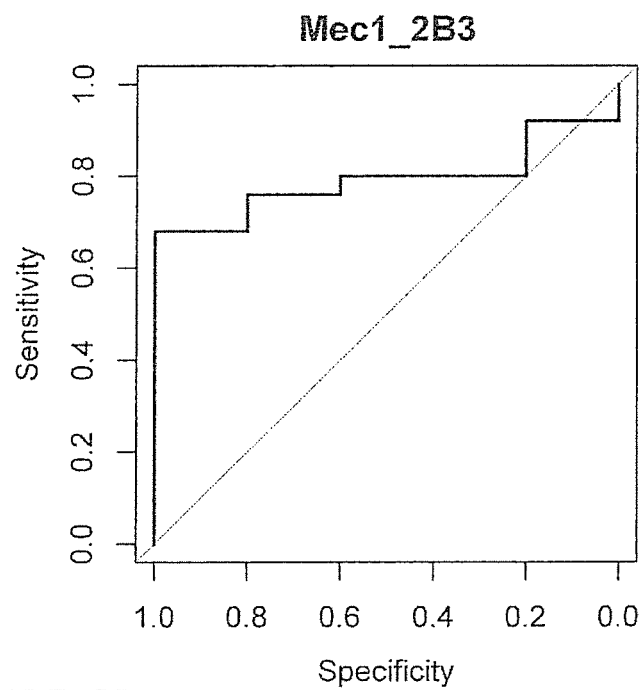
FIG. 5B shows the ROC curve of the polypeptide marker antigen Mec1_2B3.
Figure 5C:
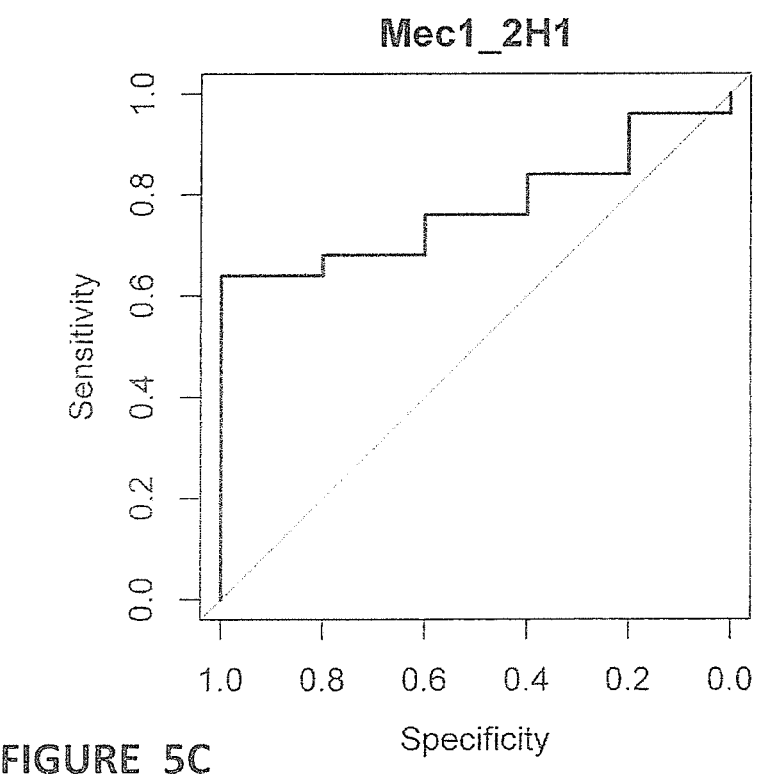
FIG. 5C shows the ROC curve of the polypeptide marker antigen Mec1_2H1.
Figure 5D:
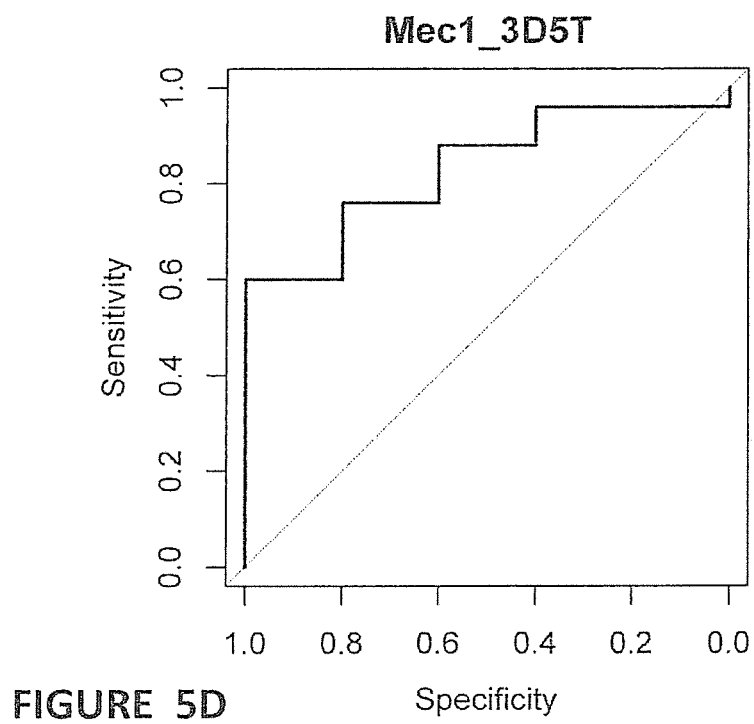
FIG. 5D shows the ROC curve of the polypeptide marker antigen Mec1_3D5T.
Figure 5E:
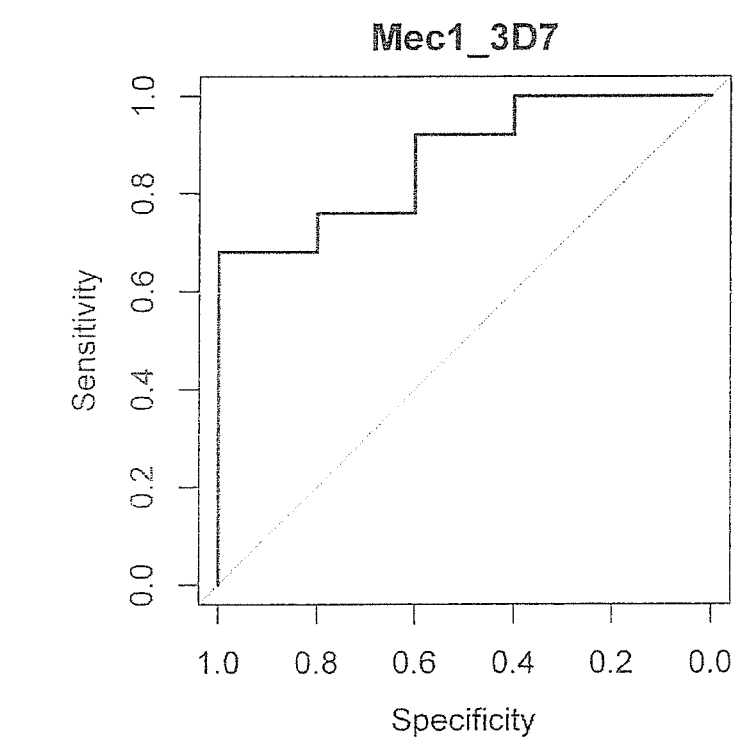
FIG. 5E shows the ROC curve of the polypeptide marker antigen Mec1_3D7.
Figure 5F:
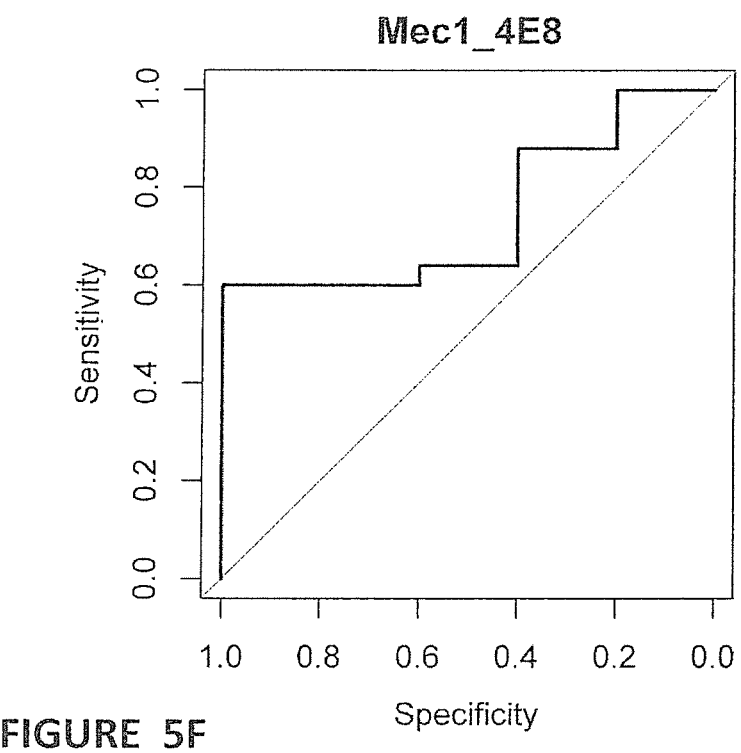
FIG. 5F shows the ROC curve of the polypeptide marker antigen Mec1_4E8.
Figure 5G:
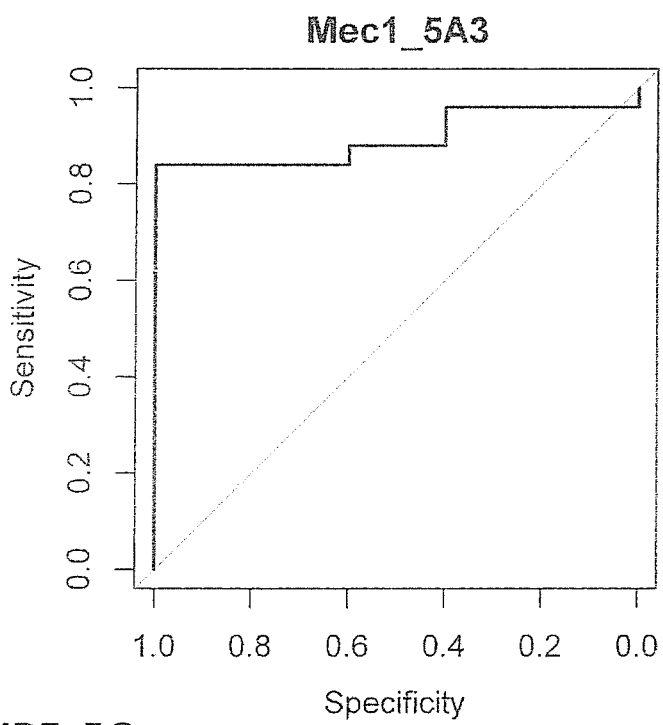
FIG. 5G shows the ROC curve of the polypeptide marker antigen Mec1_5A3.

The performance of the well-known tumor antigen p53 alone on the same sample set was poor compared to any of these 3 antigens biomarkers as indicated by its low AUC value of 0.688 (see ROC curve FIG. 4E). Because of their value in detecting autoantigen biomarkers associated with OVCA recurrence the three polypeptide antigens Mec1_4B7, Mec1_4H4, and Mec1_5H6 are included in the present invention as marker antigens.

ROC analysis indicated that seven additional polypeptide antigens are also useful predictors of OVCA recurrence; these antigens are also included in the present invention as marker antigens. These marker antigens are Mec1_1B4, Mec1_2B3, Mec1_2H1, Mec1_3D5T, Mec1_307, Mec1_4E8, and Mec1_5A3. Their amino acid sequences are given in Table 3. The ROC curves for each of these seven marker antigens is shown in FIGS. 5A to 5G. The area under contrast, the biomarker tumor antigen p53, on the same sample, whose ROC curve is shown in FIG. 4E, had an AUC value of only 0.688 (not shown). The predictive value of the seven marker antigens is further supported by their average sensitivity and accuracy values. Their average sensitivity, as calculated from the data of Table 1, is 66.3%, as opposed to a sensitivity of 8.0% for the commonly used biomarker CA125. The accuracy of the seven marker antigens, calculated from Table 2 as (TP+TN)/(TP+TN+FP+FN), is 71.9%, as opposed to 30.4% for CA125. The amino acid sequences of these seven marker antigens are given in Table 4.

In conclusion, a total of 10 polypeptide marker antigens have been proven to be useful for serological prediction of the risk of recurrence of ovarian cancer during or after primary treatment: Mec1_4B7, Mec1_4H4, Mec1_5H6, Mec1_1B4, Mec1_2B3, Mec1_2H1, Mec1_3D5T, Mec1_3D7, Mec1_4E8, and Mec1_5A3.

DISCUSSION

The management of recurrent OVCA is a major clinical challenge because relapse after front-line chemotherapy, such as platinum-based therapy, represents an aggressive disease state which currently has no clinical biomarkers, other than p53, which has its limitations that can indicate when to reinitiate treatment (30). The polypeptide marker antigens included in the present invention provide an early indication of recurrence in adenocarcinoma of the ovary that are sensitive to front-line chemotherapy, so that the second-line chemotherapy treatment can be implemented sooner than CA125 could detect disease for a better therapeutic outcome.

The results indicated that ten biomarker antigens were able to predict recurrence at a median time of 9.07 months prior to clinical recurrence of the disease in a population where 92% (23/25) recurrent OVCA patients had CA125 less than 35 U/ml at that time. The results also indicated that proteins known to be overexpressed in OVCA were not useful autoantigen recurrence biomarkers. In the same patient population CA125 alone detected recurrence with a low sensitivity of 8%, although all the non-recurrent OVCA patients were correctly categorized by CA125 as indicated by the high assay specificity (Table 1). The low sensitivity of CA125 was due to the enrollment of a particular group of recurrent OVCA patients for this study where the majority of patients had CA125 values below 35 U/ml at first post diagnosis interval before recurrence. It is noteworthy that of the 12 recurrent patients on whom complete longitudinal CA125 data was obtained, 11 had normal CA125 levels for an extended period prior to their recurrence (average interval 9 months, range 5.5-11.7 months). Clinical documentation of recurrence was not noted for a median of 9.07 months (range 2.1-18.9) after the appearance of biomarkers of the present invention. A limitation of this study is that few non-recurrent patients (OVCA patients who remained disease free after primary chemotherapy for greater than 4 years) were available for the validation study. Generally, monitoring of disease during or after front-line chemotherapy in OVCA patients with low CA125 levels is dependent on imaging studies that sometimes fails to detect the metastases that fall below the resolution limits of this technology. Therefore, the biomarker panel of the present invention is useful for predicting recurrence at an early time in ovarian cancer patient population whose CA125 values are within the normal range.

The amino acid sequences of the ten polypeptide marker peptide antigens included in the present invention are listed in Table 3. More detailed description of the marker antigens is provided in Table 4. Among these marker antigens, one of the antigens (Mec1_4B7) represents a polypeptide epitope of a known gene product, histidyl t-RNA synthetase. Histidyl-tRNA synthetase (HARS) also known as histidine-tRNA ligase, is an enzyme which in humans is encoded by the HARS gene. The protein encoded by this gene is a cytoplasmic enzyme which belongs to the class II family of aminoacyl tRNA synthetases (37). Autoantibodies to histidyl t-RNA synthetase, termed as anti-Jo-1, or to other amino acyl t-RNA synthetase occur in 25% of patients with PM and dermatomyositis (38). Iavazzo and colleagues presented a case report for a patient who developed PM after she was treated for ovarian carcinoma recurrence (39). In general, PM appears to arise in cancer patients prior to diagnosis (40, 41).

TABLE 3

Properties of marker antigens included in the present invention

| Antigen | Epitope/ Mimotope | Peptide Sequence | Description of the genes that are in-frame with T7 10B gene | Size of the peptide |
|---|---|---|---|---|
| Mec1_4B7 | Epitope | EVDVRREDLVEEIKRRTGQPLCIC (SEQ ID NO: 1) | NM_002109.3, Homo sapiens histidyl-tRNA synthetase (HARS), mRNA | 24 AA |
| Mec1_4H4 | Mimotope | PGCSTTLS (SEQ ID NO: 2) | | 8 AA |
| Mec1_5H6 | Mimotope | NSFLMTSSKPR (SEQ ID NO: 3) | | 11 AA |
| Mec1_1B4 | Mimotope | ENVLVQTN (SEQ ID NO: 4) | | 8 AA |
| Mec1_2B3 | Mimotope | ELHN (SEQ ID NO: 5) | | 10 AA |
| Mec1_2H1 | Mimotope | LGSDERRHRAP (SEQ ID NO: 6) | | 11 AA |
| Mec1_3D5T | Mimotope | VDEEDMMNQVLQRSIIDQ (SEQ ID NO: 7) | | 18 AA |
| Mec1_3D7 | Mimotope | VQAQQRSAPARAARAGHPEAGAGMEGAG (SEQ ID NO: 8) | | 28 AA |
| Mec1_4E8 | Mimotope | PKTMTQNSFG (SEQ ID NO: 9) | | 10 AA |
| Mec1_5A3 | Mimotope | YACLKD (SEQ ID NO: 10) | | 6 AA |

TABLE 4

Description of ten marker antigens of the present invention.

| Marker Antigen | Description of the genes that are in-frame with T7 10B gene | Peptide sequences of Epitope/Mimotopes, in-frame with T7 10B genes | Size of the peptide | Description of the sequences that Mimotopes mimic | Unigene # | Region of similarity of AA |
|---|---|---|---|---|---|---|
| Mec1_4B7 | NM_002109.3, Homo sapiens histidyl-tRNA synthetase (HARS), mRNA | Epitope EVDVRREDLVEEIK RRTGQPLCIC (SEQ ID NO: 1) | 24 AA | N/A | Hs.528050 | 486-509 Score = 82.5 bits (187), Expect = 2e-18 Identities = 24/24 (100%), Positives = 24/24 (100%), Gaps = 0/24 (0%) Query 1 EVDVRREDLVEEIKRRTGQPLCIC 24 EVDVRREDLVEEIKRRTGQPLCIC Sbjct 486 EVDVRREDLVEEIKRRTGQPLCIC 509 Autoantibodies to histidyl t_RNA synthetase were shown to be present in patients diagnosed with polymyositis or dermatomyositis (38). |
| Mec1_5H6 | ref\|NT_034772.6\| Homo sapiens chromosome 5 genomic contig, GRCh37.p5 | Mimotope NSFLMTSSKPR (SEQ ID NO: 3) | 11 AA | sp\|O95944.2\| NCTR2_HUMAN, Natural cytotoxicity triggering receptor 2 | Hs.194721 | 66-73 Score = 23.5 bits (48), Expect = 0.035 Identities = 7/8 (88%), Positives = 7/8 (88%), Gaps = 0/8 (0%) Query 4 LMTSSKPR 11 L TSSKPR Sbjct 66 LVTSSKPR 73 The cytolytic effect of natural killer cells in killing the neuroblastoma and glioblastoma target cells is mediated by natural cytotoxicity triggering receptor 2 (43). |
| Mec1_4H4 | NM_014671.2, Homo sapiens ubiquitin protein ligase E3C (UBE3C), mRNA | Mimotope PGCSTTLS (SEQ ID NO: 2) | 8 AA | sp\|O94966.2\| UBP19_HUMAN, Ubiquitin carboxyl-terminal hydrolase 19 | Hs.721972 | 887-894 Score = 18.9 bits (37), Expect = 0.88 Identities = 6/8 (75%), Positives = 6/8 (75%), Gaps = 0/8 (0%) Query 1 PGCSTTLS 8 PGC T LS Sbjct 887 PGCTTLLS 894 Ubiquitin carboxyl-terminal hydrolase 1 was reported as tumor suppressor and biomarker for hepatocellular carcinoma (44). |
| Mec1_1B4 | No significant similarity | Mimotope ENVLVQTN (SEQ ID NO: 4) | 8 AA | sp\|Q9C026.1\| TRIM9_HUMAN, E3 ubiquitin-protein ligase TRIM9 | Hs.733171 | 36-41 Score = 19.7 bits (39), Expect = 0.47 Identities = 5/6 (83%), Positives = 6/6 (100%), Gaps = 0/6 (0%) Query 2 NVLVQT 7 N + LVQT Sbjct 36 NILVQT 41 Trim proteins are important regulators of carcinogenesis (45). |

TABLE 4-continued

Description of ten marker antigens of the present invention.

| Marker Antigen | Description of the genes that are in-frame with T7 10B gene | Peptide sequences of Epitope/ Mimotopes, in-frame with T7 10 B genes | Size of the peptide | Description of the sequences that Mimotopes mimic | Unigene # | Region of similarity of AA | |
|---|---|---|---|---|---|---|---|
| Mec1_2B3 | NM_00119504 5, Homo sapiens Yes-associated protein 1 (YAP1), transcript variant 4, mRNA | Mimotope ELHN | 4 AA | sp|P07711.2| CATL1_HUMAN, Cathepsin L1 | Hs. 731507 | 60-63 Score = 16.8 bits (32), Expect = 0.95 Identities = 4/4 (100%), Positives = 4/4 (100%), Gaps = 0/4 (0%) Query 1 ELHN 4 ELHN Sbjct 60 ELHN 63 | Cathepsin L plays a potential role in glioblastoma invasion (5). |
| Mec1_2H1 | NR_003287.2 Homo sapiens RNA, 28S ribosomal 1 (RN28S1), ribosomal RNA | Mimotope LGSDERRHRAP (SEQ ID NO: 6) | 11 AA | sp|Q8WVS4.3| WDR60_HUMAN, WD repeat-containing protein 60 | Hs.609371 | 212-218 Score = 21.0 bits (42), Expect = 0.29 Identities = 6/7 (86%), Positives = 6/7 (86%), Gaps = 0/7 (0%) Query 5 ERRHRAP 11 ERRHR P Sbjct 212 ERRHRKP 218 | Bromo-domain and WD repeat-containing protein 3 are reported to be elevated in breast cancer (47). |
| Mec1_3D5T | NM_018683.3, Homo sapiens ring finger protein 114 (RNF114), mRNA | Epitope VDEEDMMNQVL QRSIIDQ (SEQ ID NO: 7) | 18 AA | N/A | Hs.144949 | 211-228 Score = 64.7 bits (145), Expect = 3e-15 Identities = 18/18 (100%), Positives = 18/18 (100%), Gaps = 0/18 (0%) Query 1 VDEEDMMNQVLQRSIIDQ 18 VDEEDMMNQVLQRSIIDQ Sbjct 211 VDEEDMMNQVLQRSIIDQ 228 | Ring finger protein RNF 19-A is reported as a relevant biomarker for prostate cancer detection (48). |
| Mec1_3D7 | NM_014762.3, Homo sapiens 24-dehydrocholesterol reductase (DHCR24), mRNA | Mimotope VQAAQQRSAPARA ARAGHPEAGAGM EGAG (SEQ ID NO: 8) | 28 AA | sp|Q2T9J0.3| TYSD1_HUMAN, Peroxisomal leader peptide-processing protease | Not found | 21-30 Score = 26.5 bits (55), Expect = 0.052 Identities = 8/10 (80%), Positives = 9/10 (90%), Gaps = 0/10 (0%) Query 12 AARAGHPEAG 21 A RAG + PEAG Sbjct 21 ASRAGQPEAD 30 | No relevance in cancer |
| Mec1_4E8 | NM_00111323 9.2, Homo sapiens homeodomain interacting protein kinase 2 (HIPK2), transcript variant 2, mRNA | Mimotope PKTMTQNSFG (SEQ ID NO: 9) | 10 AA | sp|Q4G0N0.2| GTA1_HUMAN, Glycoprotein alpha-galactosyl-transferase | Hs. 97469 | 86-92 Score = 21.8 bits (44), Expect = 0.12 Identities = 6/7 (86%), Positives = 6/7 (86%), Gaps = 0/7 (0%) Query 4 MTQNSFG 10 MTQ SFG Sbjct 86 MTQQSFG 92 | Galactosyl transferases are novel tumor biomarkers for gynecological cancers (49). |

TABLE 4-continued

Description of ten marker antigens of the present invention.

| Marker Antigen | Description of the genes that are in-frame with T7 10B gene | Peptide sequences of Epitope/ Mimotopes, in-frame with T7 10B genes | Size of the peptide | Description of the sequences that Mimotopes mimic | Unigene # | Region of similarity of AA |
|---|---|---|---|---|---|---|
| Mec1_5A3 | NR_003286.2, Homo sapiens 18S ribosomal RNA, (RN18S1), ribosomal RNA | Mimotope YACLKD (SEQ ID NO: 10) | 6 AA | sp\|Q14541.3\| HNF4G_HUMAN, Hepatocyte nuclear factor (HNF) 4-gamma | Hs.241529 | 237-241 Score = 20.2 bits (40), Expect = 0.17 Identities = 5/5 (100%), Positives = 5/5 (100%), Gaps = 0/5 (0%) Query 1 YACLK 5 YACLK Sbjct 237 YACLK 241 | Deregulation of HNF 4 alpha is associated with hepatocellular carcinoma progression (50). |

The polypeptide marker antigens Mec1_5H6 and Mec1_4H4 each contain an open reading frame with the T7 10B gene with a frameshift within the natural reading frame of the gene (Table 4). These polypeptides are termed as mimotopes because they mimic linear or conformational epitopes of an immunogen (21, 22).

Although autoantibodies to TAAs develop at the early onset of the disease, only a few have been evaluated as prognostic biomarkers because very little data on the evidence of tumor autoantibodies in monitoring disease or predicting recurrence in ovarian cancer patients are available. Reports from Vogl and colleagues (23) revealed 46% prevalence of circulating p53 autoantibodies in a study population comprising 83 OVCA patients. Their study also indicated that in a bivariate analysis, patients with anti-p53 autoantibodies had a 1.96-fold risk for relapse (95% confidence interval 1.02-3.78).

Polypeptide marker antigens indicating a poor response to therapy at an early time point provide a clinician with information helpful in making decisions about modifying patient treatment. Such modifications could include prolonging first-line treatment, initiating maintenance treatment, or early second-line treatment of recurrent disease. These better-informed treatment modifications should result in more durable response and greater survival among OVCA patients. There has been considerable debate on the beneficial outcome of OVCA patients from the recommencement of early chemotherapy treatment due to a rise in CA125 values during their disease monitoring phase after the completion of therapy.

Example 2: Paraneoplastic Antigens as Biomarkers for Surveillance and Prediction of Recurrence in Ovarian Cancer Materials and Methods
Patient Population Patients diagnosed and treated for late stage serous epithelial ovarian cancer at Karmanos Cancer Institute, St John Health System (Detroit, Mich.), or Oakwood Hospital (Dearborn, Mich.) were entered on to the study at the time of their diagnosis. Study participation included collection of serial blood samples starting at or near the time of surgery and continuing for every six months up to five years, concurrent with clinical lab draws. Medical records were reviewed to determine CA125 levels, disease status, chemotherapy status, disease-free interval (DFI) and time to recurrence (TTR) over a multi-year period. Serial serum samples were collected between 2003 and 2014. All participants provided written informed consent. Study procedures were approved by the Wayne State University, St. Johns Health Systems, and Oakwood Hospital Institutional Review Boards.

Specimen Collection and Processing

Samples were collected and processed using the procedure as described earlier (66). The demographics of patients in the training set were also described in earlier studies (66). For each patient in the test set 3 samples were selected; 1) the baseline blood sample (collected at time of diagnosis), 2) the blood sample collected approximately 3-15 months before the clinical recurrence, ideally with normal CA125 and no evidence of disease, and 3) the sample collected as close as possible to clinical recurrence (Table 5).

TABLE 5

Demographics of 21 ovarian cancer patients used in the test set

| StudyID | Age at Dx | BSID | DxStage Cd | Tumor Class | Tumor-Grade | DFI | OS | TTR 1 | Recur-Interval | Chemo | CA125-Recode | DxInterval | Evidenceof-DiseaseCd |
|---|---|---|---|---|---|---|---|---|---|---|---|---|---|
| P283 | 51 | 4680 | 3C | Serous | Grade 3 (high) | 11.63 | 82 | 18.27 | −18.27 | pre chemo | 2393 | 0.00 | EOD |
|  |  | 5110 |  |  | Poorly differentiated |  |  |  | −13.60 | in chemo | 22 | 4.67 | Not Specified |
|  |  | 12322 |  |  |  |  |  |  | 1.67 | recur post chemo | 95 | 19.93 | Not Specified |
| P295 | 71 | 5042 | 4 | Serous |  | 5.83 | 32 | 10.67 | −10.67 | pre chemo | 388 | 0.00 | EOD |
|  |  | 7183 |  |  |  |  |  |  | −5.77 | post chemo | 18 | 4.90 | NED |
|  |  | 12269 |  |  |  |  |  |  | 3.97 | recur in chemo | 64 | 14.63 | Not Specified |
| P336 | 60 | 12563 | 3C | Serous | Grade 3 (high) | 15.10 | 85 | 20.30 | −20.23 | pre chemo | 1185 | 0.07 | EOD |
|  |  | 12912 |  |  | Poorly differentiated |  |  |  | −10.00 | post chemo | 20 | 10.30 | NED |
|  |  | 15164 |  |  |  |  |  |  | 23.67 | recur pre chemo | 185 | 43.97 | EOD |
| P341 | 40 | 12671 | 3C | Serous | Grade 3 (high) | 0.57 | 38 | 14.60 | −14.50 | pre chemo | 1246 | 0.10 | EOD |
|  |  | 12897 |  |  | Poorly differentiated |  |  |  | −7.10 | in chemo | 37 | 7.50 | Not Specified |
|  |  | 13555 |  |  |  |  |  |  | 3.17 | in chemo | 87 | 17.77 | Not Specified |
| P300 | 69 | 7174 | 3C | Serous | Grade 3 (high) | 4.90 | 65 | 10.17 | −10.17 | pre chemo | 1226 | 0.00 | EOD |
|  |  | 11499 | 3C |  | Poorly differentiated |  |  |  | −3.73 | post chemo | 12 | 6.43 | NED |
|  |  | 12359 | 3C |  |  |  |  |  | 4.50 | recur in chemo | 246 | 14.67 | Not Specified |
| P326 | 77 | 12380 | 3C | Serous | Moderately to poorly differentiated | 10.13 | 36 | 16.27 | −16.23 | pre chemo | 1012 | 0.03 | EOD |
|  |  | 12898 | 3C |  |  |  |  |  | −4.30 | in chemo | 41 | 11.97 | Stable Disease |
|  |  | 13541 | 3C |  |  |  |  |  | 3.43 | recur in chemo | 115 | 19.70 | Tolerating treatment |

TABLE 5-continued

Demographics of 21 ovarian cancer patients used in the test set

| StudyID | Age at Dx | BSID | DxStageCd | Tumor Class | Tumor-Grade | DFI | OS | TTR1 | Recur-Interval | Chemo | CA125-Recode | DxInterval | EvidenceofDiseaseCd |
|---|---|---|---|---|---|---|---|---|---|---|---|---|---|
| P342 | 60 | 12675 | 3C | Serous | Grade 3 (high) | 3.20 | 19 | 7.67 | −7.63 | pre chemo | 182 | 0.03 | EOD |
| | | 12863 | 3C | | Poorly differentiated | | | | −3.30 | in chemo | 5 | 4.37 | NED |
| | | 12908 | 3C | | | | | | 0.90 | in chemo | 34 | 8.57 | Not Specified |
| | | 13507 | 3C | | | | | | 6.03 | in chemo | 228 | 13.70 | EOD |
| P356 | 44 | 12867 | 3C | Serous | Grade 3 (high) | 9.07 | 39 | 13.77 | −13.70 | pre chemo | 542 | 0.07 | EOD |
| | | | | | | | | 39 | 77 | | | | |
| | | 12920 | 3C | | Poorly differentiated | | | | −9.07 | in chemo | 11 | 4.70 | Tolerating treatment |
| | | 13549 | 3C | | | | | | −1.63 | post chemo | 89 | 12.13 | EOD |
| P367 | 49 | 13606 | 4 | Serous | nd | 4.33 | 19 | 10.90 | −10.90 | pre chemo | 788 | 0.00 | EOD |
| | | 146 | 4 | | | | | | −4.33 | in chemo | 29 | 6.57 | Tolerating treatment |
| | | 14893 | 4 | | | | | | 2.20 | recur in chemo | 3084 | 13.10 | EOD |
| P370 | 59 | 13615 | 3C | Serous | Grade 3 (high) | 2.63 | 32 | 8.03 | −8.03 | pre chemo | 1200 | 0.00 | EOD |
| | | 14697 | 3C | | Poorly differentiated | | | | −2.63 | in chemo | 13 | 5.40 | |
| | | 14832 | 3C | | | | | | 2.50 | recur in chemo | 300 | 10.53 | EOD |
| P178 | 35 | 887 | 3C | Serous | Grade 3 (high) | 3.50 | 34 | 9.83 | −9.80 | pre chemo | 16906 | 0.03 | EOD |
| | | 1667 | 3C | | Poorly differentiated | | | | −4.20 | in chemo | 203 | 5.63 | NED |
| | | 3817 | 3C | | | | | | 1.57 | recur in chemo | 506 | 11.40 | EOD |
| P378 | 49 | 14828 | 4A | Serous | Grade 3 (high) | 11.67 | 61 | 2827 | −28.27 | pre chemo | 1725 | 0.00 | EOD |
| | | 15180 | 4A | | Poorly differentiated | | | | −12.37 | in chemo | 9 | 15.90 | Not Specified |
| | | 15281 | 4A | | | | | | −1.87 | post chemo | 60 | 26.40 | Not Specified |
| P392 | 47 | 15175 | 3C | Serous | Grade 3 (high) | 8.5 | 28 | 13.67 | −13.67 | pre chemo | 13154 | 0.00 | EOD |
| | | 15256 | 3C | | Poorly differentiated | | | | −5.93 | post chemo | 9 | 7.73 | NED |
| | | 15292 | 3C | | | | | | 0.37 | recur in chemo | 60 | 14.03 | EOD |
| P393 | 67 | 15190 | 3C | Serous | Grade 3 (high) | 4.10 | 29 | 12.07 | −11.10 | pre chemo | 4040 | 0.97 | |
| | | 15259 | 3C | | Poorly differentiated | | | | −5.03 | in chemo | 26 | 7.03 | EOD |
| | | 15291 | 3C | | | | | | 0.23 | recur pre chemo | 3500 | 12.30 | EOD |
| P265 | 49 | 4347 | 3C | Serous | Grade 3 (high) | 4.87 | 24 | 9.50 | −9.53 | pre chemo | 2693 | −0.03 | EOD |
| | | 4694 | 3C | | Poorly differentiated | | | | −4.87 | in chemo | 54 | 4.63 | Not Specified |
| | | 5109 | 3C | | | | | | −0.43 | recur post chemo | 204 | 9.07 | Not Specified |
| P386 | 56 | 15155 | 3C | Serous | Grade 3 (high) | 16.80 | 52 | 22.73 | −22.73 | pre chemo | 584 | 0.00 | |
| | | 15178 | 3C | | Poorly differentiated | | | | −17.27 | in chemo | 16 | 5.47 | Not Specified |
| | | 15251 | 3C | | | | | | −10.50 | post chemo | 14 | 12.23 | NED |
| | | 15769 | 3C | | | | | 1.17 | | recur in chemo | 166 | 23.90 | EOD |
| P410 | 62 | 15260 | 3C | Serous | Grade 3 (high) | 8.13 | 45 | 14.77 | −14.77 | pre chemo | 3643 | 0.00 | EOD |
| | | 15776 | 3C | | Poorly differentiated | | | | −3.23 | post chemo | 24 | 11.53 | NED |
| | | 15796 | 3C | | | | | 1.20 | | recur in chemo | 568 | 15.97 | Not Specified |
| P413 | 55 | 15272 | 3C | Serous | Grade 3 (high) | 7.83 | 48 | 24.53 | −24.50 | pre chemo | 3217 | 0.03 | EOD |
| | | 15770 | 3C | | Poorly differentiated | | | | −15.53 | in chemo | 8 | 9.00 | Not Specified |
| | | 15792 | 3C | | | | | | −10.87 | in chemo | 7 | 13.67 | NED |
| P376 | 57 | 14822 | 3C | Serous | Grade 3 (high) | 17.27 | 61 | 34.33 | −34.47 | pre chemo | 1619 | −0.13 | EOD |
| | | 15264 | 3C | | Poorly differentiated | | | | −9.93 | post chemo | 7 | 24.40 | NED |
| | | 15740 | 3C | | | | | | −0.73 | post chemo | 10 | 33.60 | EOD |

TABLE 5-continued

Demographics of 21 ovarian cancer patients used in the test set

| StudyID | Age at Dx | BSID | DxStageCd | Tumor Class | Tumor-Grade | DFI | OS | TTR 1 | Recur-Interval | Chemo | CA125-Recode | DxInterval | Evidenceof-DiseaseCd |
|---|---|---|---|---|---|---|---|---|---|---|---|---|---|
| P398 | 72 | 15226 | 3C | Serous | Grade 3 (high) | 8.67 | 25 | 15.20 | −15.20 | pre chemo | 120 | 0.00 | EOD |
|  |  | 15266 | 3C |  | Poorly differentiated |  |  |  | −10.30 | in chemo | 24 | 4.90 | EOD |
|  |  | 15781 | 3C |  |  |  |  |  | 1.87 | recur in chemo | 38 | 17.07 | EOD |
| P400 | 47 | 15229 | 3C | Serous | Grade 3 (high) | 4.27 | 19 | 9.63 | −9.63 | pre chemo | 8658 | 0.00 | EOD |
|  |  | 15274 | 3C |  | Poorly differentiated |  |  |  | −4.50 | in chemo | 6 | 5.13 | Not Specified |
|  |  | 15659 | 3C |  |  |  |  |  | 0.17 | recur pre chemo | 106 | 9.80 | EOD |

The disease status of 3 sequential serum samples correlated to EOD-NED-EOD but the second sample was usually taken while still in chemo so the NED was not actually a true remission, but a response to the chemotherapy. EODs were determined by clinical/imaging data, or elevated CA125 level, or both. Future studies will include more frequent collection of interval samples to increase the pool of samples fitting the ideal profile.

Cloning of Recombinant Antigen into Bacterial Expression Vector

All the previous phage bearing tumor antigens such as 4B7 (SEQ ID NO: 1), 4H4 (SEQ ID NO: 2), 5H6 (SEQ ID NO: 3), and T7 1-2a (empty phage capsid protein used as negative control protein) as well as 2 paraneoplastic antigens such as Ro52 and CDR2 were first PCR amplified using different forward primers (containing 5' restriction site followed by His tag and T7 tag at the N terminus) and reverse primers (containing 3' stop codon followed by restriction site at the C terminus) using cDNA templates (Table 6).

TABLE 6

Primer sequences used for cloning antigen into pET-21b bacterial expression vector

| Primer | Sequence | Antigen cloned and sequenced |
|---|---|---|
| T7 Clon (for) | 5'CGCCGCCGCGGATCCGCGACGCGTCGACCATCATCATCATCATCATAT GGCTAGCATGACTGGTGGACAGCAAATG 3' (SEQ ID NO: 11) | 4B7, 5H6, T7 1-2a (cloned) |
| T7 NdeI Clon For | 5'ATAGAATCACATTAAACAGGAATTCCATATGGAATTCCATCATCATCAT CATCATGGTGTTATGGCTAGCATGACTGGTGGACAGCAAATG 3' (SEQ ID NO: 12) | 4H4 (cloned) |
| 17 reverse primer | 5'CCTCCTTTCAGCAAAAAACCCC 3' (SEQ ID NO: 13) | 4B7, 4H4, 5H6 (cloned) |
| T7Select seq primer (for) | 5' TGCTAAGGACAACGTTATCGG 3' (SEQ ID NO: 14) | 467, 4H4, 5H6, T7 1-2a (sequenced) |
| New pET 17 Prom Seq | 5' AGATCTCGATCCCGCGAAATTAATACGACTCACTATAGGG 3' (SEQ ID NO: 15) | 4B7, 4H4, 5H6, Ro52, CDR2, T7 1-2a (sequenced) |
| CDR2-NdeI-For | 5'ATCACATTAAACAGGAATTCCATATGGAATTCCATCATCATCATCATCA TGGTGTTATGGCTAGCATGACTGGTGGACAGCAAATGGGTGGGATGCT GGCGGAAAACCTGGTAGAGGAGT 3' (SEQ ID NO: 16) | CDR2 (cloned) |
| CDR2-Xho I Rev: | 5'CGCGGATCCCGCTCGAGCGGTAGAGCTAGAGGTTCAATTAAGAATGA GAGGAGAGTGATC 3' (SEQ ID NO: 17) | CDR2 (cloned) |
| CDR2-Seq | 5' AGGAATATGGGCTCGTGTTAAAGGAGAACAGTGAAC 3' (SEQ ID NO: 18) | CDR2 (sequenced) |
| Ro52-SalI For | 5'CGCCGCCGCGGATCCGCGACGCGTCGACCATCATCATCATCATCATAT GGCTTCAGCAGCACGCTTGACAATGATGTGGGAGG 3' (SEQ ID NO: 19) | Ro52 (cloned) |
| Ro52-XhoI Rev | 5'CGCGGATCCCGCTCGAGCGGCCATCAATAGTCAGTGGATCCTTGTGAT CCAATA 3' (SEQ ID NO: 20) | Ro52 (cloned) |
| Ro52-Seq | 5' TCCATGCCAAGTTGGGATTTTCCTGGACTATGAGGCTGGCAT 3' (SEQ ID NO: 21) | Ro52 (sequenced) |

For phage antigens, the cDNA templates were obtained from ovarian tumor T7 phage cDNA libraries and for paraneoplastic antigens, cDNAs were prepared from different ovarian cancer cell lines. The PCR products were column purified (Qiagen, Germantown, Md.), restriction digested, column purified again and successively ligated to pET-21b bacterial expression vector by following manufacturer's protocol (EMD Millipore Corporation, San Diego, Calif.). The ligated DNA was then transformed into BL21-DE3 strain and several colonies were picked and sequenced. Positive colonies bearing the respective genes were further employed for in vivo production of recombinant His and T7-tagged proteins in Bl21-DE3 bacterial strain. All cDNA clones were DNA sequence verified by standard techniques.

Production and Purification of Recombinant his and T7 Tagged Proteins

BL21-DE3 bacterial cells bearing clones, pET21b-4B7, pET21b-4H4, pET21b-5H6, pET21b-Ro52, pET21b-CDR2, and pET21b-T71-2a (negative control) were grown overnight in 10 ml LB with 50 µg/ml ampicillin at 37° C. About 4 ml of the overnight culture was added to 400 ml LB with 50 µg/ml ampicillin and was grown at 37° C. to OD between 0.4-0.5. After it reached the desired OD, 0.6 mM IPTG was added to induce the production of RNA polymerase that was needed for RNA and subsequent protein synthesis and the culture was grown at 37° C. for 3.5 hours. The cells were pelleted at 3,700 rpm for 20 minutes and the supernatant was discarded. The pellet was frozen at −20° C. for at least 30 minutes and then lysed with BPER lysing buffer (Thermo Fisher Scientific, Grand Island, N.Y.) centrifuged at 15,000×g and then transferred the supernatant. The pellet containing the inclusion bodies were solubilized in 8M urea because pET21b expression system (EMD Millipore Corporation, San Diego, Calif.) results in enormous expression of our desired proteins that are found in inclusion bodies that only can be solubilized with 8M urea. The crude His and T7-tagged proteins were purified first using Ni-NTA agarose beads (Thermo Fisher Scientific, Grand Island, N.Y.) following manufacturer's protocol. Ni-NTA agarose beads binds to His residues that are attached to proteins and results in relatively pure protein. The Ni-NTA purified His-tagged proteins were further purified using agarose beads bound to T7 antibody by following manufacturer's instruction (EMD Millipore Corporation, San Diego, Calif.). The second round of purification with T7 antibody bound agarose beads is necessary to remove all bacterial poly-His containing proteins from first round of purification with Ni-NTA beads. Only HARS protein was commercially purchased. All the recombinant pET21b-antigens will be referred by just their names from hereon forward.

Immunoscreening of Ovarian Cancer Patient Serum Samples Using Purified Recombinant Antigens For the purified recombinant Ro52 antigen, 0.06 µg of protein was used because very strong reactivity of Ro52 protein with some ovarian cancer patients was observed in earlier studies and this high intensity of the protein band determined by the Odyssey software was found to be beyond the saturation limit (data not shown). The optimum amount of 0.06 µg for Ro52 antigen was obtained by immunoscreening serum samples obtained from 1 ovarian cancer patient and a patient with benign disease using different microgram amounts of purified Ro52 protein. For all other antigens, 1 µg of purified recombinant proteins was used for SDS-PAGE and proteins were transferred onto nitrocellulose membrane. The membrane was blocked in 5% milk in TBST for 1 hour and incubated with ovarian cancer patient's serum at a dilution of 1:300 for 1 hour at room temperature. The membrane was washed 3 times with TBST followed by incubation with rabbit-anti human secondary antibody conjugated with an IR dye-800 (Rockland Antibodies and Assays, Limerick, Pa.) at a dilution of 1:5000 for 1 hour at room temperature. After washing the membrane 3 times with TBST, anti-6X His-Tag mouse monoclonal antibody Dylight 680 conjugated (Rockland Antibodies and Assays, Limerick, Pa.) was added at dilution of 1:10000 and incubated for 1 hour at room temperature. The membrane was scanned at 800 nm and 700 nm separately and the band intensity for each protein was quantitated, normalized to its His-tag using Odyssey software.

Determination of Threshold of Each Antigen Using the Training Set

Threshold of each antigen was calculated based on the immunoreactivity of T71-2a protein (negative control) with the all the ovarian cancer patients (5 recurrent and 5 non-recurrent) in the training set. The median (Median T71-2a) and standard deviation (STDEV) of the normalized signal intensity values representing the immunoreactivity of T71-2a protein with 5 recurrent patients (serum samples were obtained at months to 1 year before the clinical recurrence) and the 5 non-recurrent patients (serum samples were obtained at approximately 1 year from ovarian cancer diagnosis) in the training set was calculated as shown as Table 7.

TABLE 7

Determination of threshold of an antigen that discriminated recurrent ovarian cancer patients (serum was drawn close to 1 year before clinical recurrence) from non-recurrent ovarian cancer patients (serum was drawn close to 1 year after diagnosis) in the training set

| Antigen biomarker | Threshold of antigen | Sensitivity (percent reactivity of an antigen with recurrent ovarian cancer patients) | Specificity (percent non-reactivity of an antigen with non-recurrent ovarian cancer patients) |
| --- | --- | --- | --- |
| Ro52 | 0.17 | 60% (3/5) | 75% (3/4)* |
| CDR2 | 0.17 | 80% (4/5) | 80% (4/5) |
| HARS | 0.03 | 40% (2/5) | 40% (2/5) |
| 4B7 | 0.03 | 20% (1/5) | 80% (4/5) |
| 4H4 | 0.03 | ● | ● |
| 5H6 | 0.03 | 20% (1/5) | 80% (4/5) |
| T7 1-2a (negative control) ∆ | 0.03 | 20% (1/5) | 100% (5/5) |

Note:
Calculation of threshold for each antigen:
Normalized signal intensity value was calculated by dividing the background corrected signal intensity obtained with patient's serum by background corrected signal intensity obtained from His-tag antibody.
Median of normalized signal intensity value of T7 1-2a (negative control) with 5 recurrent and 5 non-recurrent ovarian cancer patients in the training set was 0.010.
Standard Deviation (STDEV) of the normalized signal intensity value of T7 1-2a (negative control) with 5 recurrent and 5 non-recurrent ovarian cancer patients in the training set was 0.0173.
Please note that the threshold values were adjusted to 2 places of decimal in excel worksheet (data not shown).
Threshold for HARS, 4B7, 4H4, 5H6: (Median T7 1-2a + 1.3*STDEV) = (0.010 + 1.3 × 0.0173) = 0.03 (after adjusted to 2 places of decimal).
Threshold for Ro52, CDR2: (Median T7 1-2a + 9*STDEV) = (0.010 + 9 × 0.0173) = 0.17 (after adjusted to 2 places of decimal).
*Did not have data for 1 non-recurrent ovarian cancer patient for Ro52 protein.
● Using the threshold 0.03, 4H4 did not get selected but it was still used for the test set because training set had small sample size and strict rules could not be applied.
∆ Although T71-2a, the negative control protein showed 20% sensitivity and 100% specificity in the training set (Table 2), it only revealed 4.8% sensitivity in the test set (Table 4). The antigens that showed sensitivity >10% in the test set were only selected for further analyses.

The threshold for each antigen was chosen in such a way to achieve higher percent specificity against 5 non-recurrent ovarian cancer patients in the training set as shown in Table 7 that also listed the sensitivity of each antigen that reacted with 5 recurrent ovarian cancer patients. For moderate to weakly reactive antigens such as HARS, 4B7, 4H4, 5H6, a threshold of 0.03 (Median T71-2a+1.3*STDEV) was used. For strongly reactive antigens, such as Ro52 and CDR2 antigens, a threshold of 0.17 (Median T71-2a+9*STDEV) was used. These thresholds were next applied to determine the sensitivity of each antigen that can predict recurrence in 21 independent ovarian cancer patients in the test set. Although T71-2a, the negative control protein showed 20% sensitivity and 100% specificity in the training set (Table 7), it only revealed 4.8% (1/21) sensitivity in the test set (Table 8). The antigens that showed sensitivity >10% in the test set were only selected for further analyses.

TABLE 8

Reactivity of antigens with 5 recurrent and 5 non-recurrent ovarian cancer patients (training set) and an independent recurrent ovarian patient population (test set, n = 21)

| Sample-BSID | Sample | Recur Interval (T2) | Reactivity of Antigen Biomarkers | | | | | | |
|---|---|---|---|---|---|---|---|---|---|
| Training Set | Training Set | | CA125 | HARS | 4B7 | 4H4 | 5H6 | Ro52 | CDR2 | T71-2a |
| 674 | P128-Cancer(R-T2 | −8.70 | 13 | 0.1 | | | | | 0.21 | |
| 1740 | P135-Cancer(R)-T2 | −16.30 | 11 | | | | | 15.15 | 1.75 | |
| 1681 | P146-Cancer(R)T2 | −8.20 | 25 | 0.09 | | | | | 0.45 | |
| 3905 | P184-Cancer(R)-T2 | −14.30 | 5 | | | | | | 0.2 | |
| 3776 | P175-Cancer(R)-T2 | −9.50 | 18 | | 0.09 | | 0.13 | 34.5 | 0.3 | 0.06 |
| 784 | P25-Cancer(NR)-T2 | | 12 | 0.1 | | | | | | |
| 832 | P164-Cancer(NR)-T2 | | 28 | | | | | | | |
| 4012 | P189-Cancer(NR)-T2 | | 6 | 0.07 | | | | 1.93 | 0.29 | |
| 4069 | P206-Cancer(NR)-T2 | | 7 | | | | | | | |
| 7428 | P281-Cancer(NR)-T2 | | 6 | 0.06 | 0.07 | | 0.04 | | | |

| Test Set | Test Set | | CA125 | HARS | 4B7 | 4H4 | 5H6 | Ro52 | CDR2 | T71-2a* | Number of Antigens reacting with each patient |
|---|---|---|---|---|---|---|---|---|---|---|---|
| 1667 | P178-Cancer(R)-T2 | −4.20 | 203 | 0.04 | 0.04 | 0.04 | | 1.65 | | | 4 |
| 4694 | P265-Cancer(R)-T2 | −4.87 | 54 | 0.09 | 0.06 | 0.04 | 0.04 | | 1.06 | | 5 |
| 7183 | P295-Cancer(R)-12 | −5.77 | 18 | 0.22 | | | | | 0.21 | | 2 |
| 5110 | P283-Cancer(R)-T2 | −13.60 | 22 | 0.05 | | | | | 1.82 | | 2 |
| 11499 | P300-Cancer(R)-T2 | −3.73 | 12 | 0.05 | | | | | 0.21 | 0.34 | 3 |
| 12898 | P326*-Cancer(R)-T2 | −4.30 | 41 | 0.04 | | | | 1.49 | 0.81 | | 3 |
| 12912 | P336-Cancer(R)-T2 | −10.00 | 20 | | | | | | | | 0 |
| 12897 | P341-Cancer(R)-T2 | −7.10 | 37 | 0.04 | | | | | 1.45 | | 2 |
| 12863 | P342-Cancer(R)-T2 | −3.30 | 5 | | | | 0.04 | | | | 1 |
| 12920 | P356*-Cancer(R)-T2 | −9.07 | 11 | | | | | | | | 0 |
| 14698 | P367*-Cancer(R)-T2 | −4.33 | 29 | 1.34 | | | | 4.93 | 0.37 | | 3 |
| 14697 | P370-Cancer(R)-T2 | −2.63 | 13 | 0.11 | | | | 10.24 | 0.32 | | 3 |
| 15178 | P386-Cancer(R)-T2 | −17.27 | 16 | | | | | | 0.25 | 0.5 | 2 |

TABLE 8-continued

Reactivity of antigens with 5 recurrent and 5 non-recurrent ovarian cancer patients (training set) and an independent recurrent ovarian patient population (test set, n = 21)

| Sample-BSID | Sample | Recur Interval (T2) | Reactivity of Antigen Biomarkers | | | | | | | |
|---|---|---|---|---|---|---|---|---|---|---|
| 15256 | P392-Cancer(R)-T2 | −5.93 | 9 | 0.06 | | | | 0.38 | | 2 |
| 15264 | P376-Cancer(R)-T2 | −9.93 | 7 | 0.04 | | | | 0.38 | 0.51 | 3 |
| 15180 | P378-Cancer(R)-T2 | −12.37 | 9 | | | | | 0.22 | | 1 |
| 15259 | P393*-Cancer(R)-T2 | −5.03 | 26 | 0.09 | | | | | 0.55 | 2 |
| 15266 | P398*-Cancer(R)-T2 | −10.30 | 24 | 0.04 | | | | 1.14 | | 2 |
| 15274 | P400-Cancer(R)-T2 | −4.50 | 6 | | | | | | 0.21 | 1 |
| 15776 | P410-Cancer(R)-T2 | −3.23 | 24 | 0.07 | 0.2 | 0.2 | 0.12 | 20.21 | 0.36 | 0.06 | 6 |
| 15770 | P413-Cancer(R)-T2 | −15.53 | 8 | 0.37 | 1.05 | 2 | | | | |

Results

Applicants' goal is to predict recurrence prior to the biochemical (CA125 level) or clinical/radiologic evidence of recurrence so that re-initiation of therapy can maximize the chances of improving overall survival in ovarian cancer patients. To this end tumor autoantibody biomarkers were utilized in ovarian cancer patients diagnosed with late stage serous adenocarcinoma. After subtractive biopanning with sera from ovarian cancer patients and healthy controls, protein microarrays were employed using phage lysates of single phage bearing cDNA clone to identify cDNA clones of antigens that specifically reacted with sera from ovarian cancer patients (68). It was found that these clones were good biomarkers for both early detection (68) and recurrence (69) of ovarian cancer. In addition, the antigen clones were frequently homologous to known paraneoplastic antigens and autoantibodies to these paraneoplastic antigens can occur in asymptomatic cancer patients and can be used for diagnostic purposes. After cloning, bacterial expression and purification of the most informative antigen biomarkers, a serological immunoscreening was performed using western blotting to evaluate the sensitivity of these recombinant proteins to predict recurrence prior to the rise in CA125 level (cutoff 35 U/ml) or radiologic indication of clinical recurrence in an independent retrospective cohort of ovarian cancer study population.

Serological Screening of Ovarian Cancer Patients Using Recombinant Protein Biomarkers To determine the threshold of immunoreactivity of each antigen, an initial immunoscreening was performed with 5 recurrent and 5 non-recurrent ovarian cancer patients (training set) using 6 biomarkers, namely HARS, 4B7, 4H4, 5H6, Ro52, CDR2, and T7 1-2a (which served as a negative control protein) as described in Materials and Methods section (see reference 5 for patients' demographics used in the training set) (66), (Table 7). The threshold for each antigen was next applied to evaluate the immunoreactivity of antigens with serum IgGs obtained from 21 ovarian cancer patients at 3 different time points, initially at the time of diagnosis (T1) when the patients had elevated CA125 levels, during the monitoring phase approximately 3-15 months before their clinical recurrence (T2) when most of the patients had their CA125 values within the normal range (<35 U/ml) and lastly at the time of recurrence (T3) (discussed in Materials and Methods). Immunoreactivity of 6 antigens was measured by western blot to evaluate the association of immunoreactivity with the recurrence status of ovarian cancer patients months before their clinical recurrence (Table 9A-9B)), Table 5 (for patients demographics used in the test set). For data analyses, the first 2 time points, T1 and T2, were focused on because the goal was to ascertain how early in time an association of immunoreactivity of antigens with recurrence can be made during the surveillance period prior to the rise in CA125 levels.

TABLE 9A

Association of immunoreactivity of Ro52, CDR2 and HARS antigens with the recurrence status of 21 ovarian cancer patients

| | | | | Ro52 | | |
|---|---|---|---|---|---|---|
| Sample ID | RecurInterval (T2) | Disease status at T2 | CA125 value at T2 | Comparison of level of Ro52 immunoreactivity at T2 and T1 BC represents immunoreactivity value below cutoff at T2 | Association of Ro52 immunoreactivity at T2 with recurrence status (Asso-R) | Western blot FIG. NO. |
| P178 | −4.20 | In chemo, NED | 203 | Immunoreactivity value at T1 was almost same as at T2 | Asso-R | FIG. 6B (a, b, lane 5) |
| P265 | −4.87 | In chemo, NED | 54 | BC | None | FIG. 6A (a, b, lane 5) |

TABLE 9A-continued

Association of immunoreactivity of Ro52, CDR2 and HARS antigens with the recurrence status of 21 ovarian cancer patients

| P295  | −5.77  | post chemo, NED          | 18 | BC                                                                  | None   |                       |
|-------|--------|--------------------------|----|---------------------------------------------------------------------|--------|-----------------------|
| P283  | −13.60 | In chemo, NED            | 22 | BC                                                                  | None   |                       |
| P300  | −3.73  | post chemo, NED          | 12 | Immunoreactivity value at T2 was 2.2 fold higher than at T1         | Asso-R |                       |
| P326* | −4.30  | In chemo, stable disease | 41 | Immunoreactivity value at T2 was 51.5 fold higher than at T1        | Asso-R | FIG. 6E (a, b, lane 5)|
| P336  | −10.00 | post chemo, NED          | 20 | BC                                                                  | None   |                       |
| P341  | −7.10  | In chemo, NED            | 37 | BC                                                                  | None   | FIG. 6H (a, b, lane 5)|
| P342  | −3.30  | In chemo, NED            | 5  | BC                                                                  | None   |                       |
| P356* | −9.07  | In chemo, tolerating treatment | 11 | BC at T2; immunoreactivity value at T1 was missing            | None   |                       |
| P367* | −4.33  | In chemo, tolerating treatment | 29 | Immunoreactivity value at T2 was 1.4 fold higher than at T1   | Asso-R | FIG. 6F (a, b, lane 5)|
| P370  | −2.63  | In chemo, NED            | 13 | Immunoreactivity value at T2 dropped by 2 fold                      | Asso-R | FIG. 6D (a, b, lane 5)|
| P386  | −17.27 | In chemo, Not specified  | 16 | Immunoreactivity value at T2 was 1.9 fold higher than at T1         | Asso-R |                       |
| P392  | −5.93  | post chemo, NED          | 9  | BC                                                                  | None   |                       |
| P376  | −9.93  | post chemo, NED          | 7  | Immunoreactivity value at T2 was 5.5 fold higher than at T1         | Asso-R |                       |
| P378  | −12.37 | In chemo, NED            | 9  | The value of IMR at T2 significantly dropped by 21.6 fold           | Asso-R |                       |
| P393* | −5.03  | In chemo, EOD            | 26 | BC                                                                  | None   | FIG. 6J (a, b, lane 5)|
| P398* | −10.30 | In chemo, EOD            | 24 | Immunoreactivity value at T1 was almost same as at T2               | Asso-R | FIG. 6I (a, b, lane 5)|
| P400  | −4.50  | In chemo, NED            | 6  | BC                                                                  | None   |                       |
| P410  | −3.23  | post chemo, NED          | 24 | Immunoreactivity value at T2 was 1.6 fold higher than at T1         | Asso-R | FIG. 6C (a, b, lane 5)|
| P413  | −15.53 | In chemo, NED            | 8  | Immunoreactivity value at T2 significantly dropped by 20.9 fold     | Asso-R | FIG. 6G (a, b, lane 5)|

| Sample ID | RecurInterval (T2) | Disease status | CA125 value at T2 | Comparison of level of CDR2 immunoreactivity at T2 and T1 BC represents immunoreactivity value below cutoff at T2 | Association of CDR2 immunoreactivity at T2 with recurrence status (Asso-R) | Western blot FIG. NO. |
|---|---|---|---|---|---|---|
| | | | | | | CDR2 |
| P178  | −4.20  | In chemo, NED            | 203 | BC                                                                | None   | FIG. 6B (a, b, lane 6) |
| P265  | −4.87  | In chemo, NED            | 54  | Immunoreactivity value at T2 was 2.4 fold higher than at T1       | Asso-R | FIG. 6A (a, b, lane 6) |
| P295  | −5.77  | post chemo, NED          | 18  | Immunoreactivity value at T1 was almost same as at T2             | Asso-R |                        |
| P283  | −13.60 | In chemo, NED            | 22  | Immunoreactivity value at T1 was almost same as at T2             | Asso-R |                        |
| P300  | −3.73  | post chemo, NED          | 12  | Immunoreactivity value at T1 was almost same as at T2             | Asso-R |                        |
| P326* | −4.30  | In chemo, stable disease | 41  | Immunoreactivity value at T2 dropped by 1.5 fold                  | Asso-R | FIG. 6E (a, b, lane 6) |
| P336  | −10.00 | post chemo, NED          | 20  | BC                                                                | None   |                        |
| P341  | −7.10  | In chemo, NED            | 37  | Immunoreactivity value at T2 was 1.7 fold higher than at T1       | Asso-R | FIG. 6H (a, b, lane 6) |
| P342  | −3.30  | In chemo, NED            | 5   | BC                                                                | None   |                        |
| P356* | −9.07  | In chemo, tolerating treatment | 11 | BC                                                           | None   |                        |
| P367* | −4.33  | In chemo, tolerating treatment | 29 | Immunoreactivity value at T1 was almost same as at T2        | Asso-R | FIG. 6F (a, b, lane 6) |
| P370  | −2.63  | In chemo, NED            | 13  | Immunoreactivity value at T2 dropped by 1.6 fold                  | Asso-R | FIG. 6D (a, b, lane 6) |
| P386  | −17.27 | In chemo, Not specified  | 16  | Immunoreactivity value at T2 was 1.4 fold higher than at T1       | Asso-R |                        |

TABLE 9A-continued

Association of immunoreactivity of Ro52, CDR2 and HARS antigens with the recurrence status of 21 ovarian cancer patients

| | | | | | | |
|---|---|---|---|---|---|---|
| P392 | −5.93 | post chemo, NED | 9 | Immunoreactivity value at T2 dropped by 2 fold | Asso-R | |
| P376 | −9.93 | post chemo, NED | 7 | Immunoreactivity value at T1 was almost same as at T2 | Asso-R | |
| P378 | −12.37 | In chemo, NED | 9 | BC | None | |
| P393* | −5.03 | In chemo, EOD | 26 | Immunoreactivity value at T2 dropped by 1.4 fold | Asso-R | FIG. 6J (a, b, lane 6) |
| P398* | −10.30 | In chemo, EOD | 24 | BC | None | FIG. 6I (a, b, lane 6) |
| P400 | −4.50 | In chemo, NED | 6 | Immunoreactivity value at T1 was almost same as at T2 | Asso-R | |
| P410 | −3.23 | post chemo, NED | 24 | Immunoreactivity value at T1 was almost same as at T2 | Asso-R | FIG. 6C (a, b, lane 6) |
| P413 | −15.53 | In chemo, NED | 8 | Immunoreactivity value at T1 was almost same as at T2 | Asso-R | FIG. 6G (a, b, lane 6) |

| | | | | HARS | | |
|---|---|---|---|---|---|---|
| Sample ID | RecurInterval (T2) | Disease status at T2 | CA125 value at T2 | Comparison of level of HARS immunoreactivity at T2 and T1 BC represents immunoreactivity value below cutoff at T2 | Association of HARS immunoreactivity at T2 with recurrence status (Asso-R) | Western blot FIG. NO. |
| P178 | −4.20 | In chemo, NED | 203 | Immunoreactivity value at T1 was almost same as at T2 | Asso-R | FIG. 6B (a, b, lane 1) |
| P265 | −4.87 | In chemo, NED | 54 | Immunoreactivity value at T2 was 2.2 fold higher than at T1 | Asso-R | FIG. 6A (a, b, lane 1) |
| P295 | −5.77 | post chemo, NED | 18 | Immunoreactivity value at T1 was almost same as at T2 | Asso-R | |
| P283 | −13.60 | In chemo, NED | 22 | Immunoreactivity value at T1 was almost same as at T2 | Asso-R | |
| P300 | −3.73 | post chemo, NED | 12 | Immunoreactivity value at T1 was almost same as at T2 | Asso-R | |
| P326* | −4.30 | In chemo, stable disease | 41 | Immunoreactivity value at T1 was almost same as at T2 | Asso-R | FIG. 6E (a, b, lane 1) |
| P336 | −10.00 | post chemo, NED | 20 | BC | None | |
| P341 | −7.10 | In chemo, NED | 37 | Immunoreactivity value at T2 dropped by 1.4 fold at T2 | Asso-R | FIG. 6H (a, b, lane 1) |
| P342 | −3.30 | In chemo, NED | 5 | BC | None | |
| P356* | −9.07 | In chemo, tolerating treatment | 11 | BC | None | |
| P367* | −4.33 | In chemo, tolerating treatment | 29 | Immunoreactivity value at T2 was 2 fold higher than at T1 | Asso-R | FIG. 6F (a, b, lane 1) |
| P370 | −2.63 | In chemo, NED | 13 | Immunoreactivity value at T1 was almost same as at T2 | Asso-R | FIG. 6D (a, b, lane 1) |
| P386 | −17.27 | In chemo, Not specified | 16 | BC | None | |
| P392 | −5.93 | post chemo, NED | 9 | Immunoreactivity value at T2 dropped by 2.5 fold | Asso-R | |
| P376 | −9.93 | post chemo, NED | 7 | Immunoreactivity value at T2 dropped by 1.5 fold | Asso-R | |
| P378 | −12.37 | In chemo, NED | 9 | BC | None | |
| P393* | −5.03 | In chemo, EOD | 26 | Immunoreactivity value at T1 was almost same as at T2 | Asso-R | FIG. 6J (a, b, lane 1) |
| P398* | −10.30 | In chemo, EOD | 24 | Immunoreactivity value at T1 was almost same as at T2 | Asso-R | FIG. 6I (a, b, lane 1) |
| P400 | −4.50 | In chemo, NED | 6 | BC | None | |
| P410 | −3.23 | post chemo, NED | 24 | Immunoreactivity value at T2 was 1.6 fold higher than at T1 | Asso-R | FIG. 6C (a, b, lane 1) |
| P413 | −15.53 | In chemo, NED | 8 | BC | None | FIG. 6G (a, b, lane 1) |

Note:
Ovarian cancer patients with asterisk had evidence of disease months before the clinical recurrence;
NED: No evidence of disease;
EOD: Evidence of disease.
T1 represents time at ovarian cancer diagnosis;
T2 represents time in months before the clinical recurrence.

TABLE 9B

Association of immunoreactivity of 4B7, 4H4, and 5H6 antigens with the recurrence status of 21 ovarian cancer patients

| | | | | 4B7 | | |
|---|---|---|---|---|---|---|
| Sample | RecurInterval | Disease status | CA125 | Comparison of level of 4B7 immunoreactivity at T2 and T1 | Association of 4B7 | Western blot |
| ID | (T2) | at T2 | value at T2 | BC represents immunoreactivity value below cutoff at T2 | immunoreactivity at T2 with recurrence status (Asso-R) | FIG. NO. |
| P178 | −4.20 | In chemo, NED | 203 | Immunoreactivity value at T2 was 2.2 fold higher than at T1 | Asso-R | FIG. 6B (a, b, lane 2) |
| P265 | −4.87 | In chemo, NED | 54 | Immunoreactivity value at T2 was 2 fold higher than at T1 | Asso-R | FIG. 6A (a, b, lane 2) |
| P295 | −5.77 | post chemo, NED | 18 | BC | None | |
| P283 | −13.60 | In chemo, NED | 22 | BC | None | |
| P300 | −3.73 | post chemo, NED | 12 | BC | None | |
| P326* | −4.30 | In chemo, stable disease | 41 | BC | None | FIG. 6E (a, b, lane 2) |
| P336 | −10.00 | post chemo, NED | 20 | BC | None | |
| P341 | −7.10 | In chemo, NED | 37 | BC | None | FIG. 6H (a, b, lane 2) |
| P342 | −3.30 | In chemo, NED | 5 | BC | None | |
| P356* | −9.07 | In chemo, tolerating treatment | 11 | BC | None | |
| P367* | −4.33 | In chemo, tolerating treatment | 29 | BC | None | FIG. 6F (a, b, lane 2) |
| P370 | −2.63 | In chemo, NED | 13 | BC | None | FIG. 6D (a, b, lane 2) |
| P386 | −17.27 | In chemo, Not specified | 16 | BC | None | |
| P392 | −5.93 | post chemo, NED | 9 | BC | None | |
| P376 | −9.93 | post chemo, NED | 7 | BC | None | |
| P378 | −12.37 | In chemo, NED | 9 | BC | None | |
| P393* | −5.03 | In chemo, EOD | 26 | BC | None | FIG. 6J (a, b, lane 2) |
| P398* | −10.30 | In chemo, EOD | 24 | BC | None | FIG. 6I (a, b, lane 2) |
| P400 | −4.50 | In chemo, NED | 6 | BC | None | |
| P410 | −3.23 | post chemo, NED | 24 | Immunoreactivity value at T2 was 1.4 fold higher than at T1 | Asso-R | FIG. 6C (a, b, lane 2) |
| P413 | −15.53 | In chemo, NED | 8 | BC | None | FIG. 6G (a, b, lane 2) |

| | | | | 4H4 | | |
|---|---|---|---|---|---|---|
| Sample | RecurInterval | Disease status | CA125 | Comparison of level of 4H4 immunoreactivity at T2 and T1 | Association of 4H4 | Western blot |
| ID | (T2) | at T2 | value at T2 | BC represents immunoreactivity value below cutoff at T2 | immunoreactivity at T2 with recurrence status (Asso-R) | FIG. NO. |
| P178 | −4.20 | In chemo, NED | 203 | Immunoreactivity value at T2 was 5.6 fold higher than at T1 | Asso-R | FIG. 6B (a, b, lane 3) |
| P265 | −4.87 | In chemo, NED | 54 | Immunoreactivity value at T2 was 1.7 fold higher than at T1 | Asso-R | FIG. 6A (a, b, lane 3) |
| P295 | −5.77 | post chemo, NED | 18 | BC | None | |
| P283 | −13.60 | In chemo, NED | 22 | BC | None | |
| P300 | −3.73 | post chemo, NED | 12 | BC | None | |
| P326* | −4.30 | In chemo, stable disease | 41 | BC | None | FIG. 6E (a, b, lane 3) |
| P336 | −10.00 | post chemo, NED | 20 | BC | None | |
| P341 | −7.10 | In chemo, NED | 37 | BC | None | FIG. 6H (a, b, lane 3) |
| P342 | −3.30 | In chemo, NED | 5 | BC | None | |
| P356* | −9.07 | In chemo, tolerating treatment | 11 | BC | None | |
| P367* | −4.33 | In chemo, tolerating treatment | 29 | BC | None | FIG. 6F (a, b, lane 3) |
| P370 | −2.63 | In chemo, NED | 13 | BC | None | FIG. 6D (a, b, lane 3) |

TABLE 9B-continued

Association of immunoreactivity of 4B7, 4H4, and 5H6 antigens with the recurrence status of 21 ovarian cancer patients

| | | | | | | |
|---|---|---|---|---|---|---|
| P386 | −17.27 | In chemo, Not specified | 16 | BC | None | |
| P392 | −5.93 | post chemo, NED | 9 | BC | None | |
| P376 | −9.93 | post chemo, NED | 7 | BC | None | |
| P378 | −12.37 | In chemo, NED | 9 | BC | None | |
| P393* | −5.03 | In chemo, EOD | 26 | BC | None | FIG. 6J (a, b, lane 3) |
| P398* | −10.30 | In chemo, EOD | 24 | BC | None | FIG. 6I (a, b, lane 3) |
| P400 | −4.50 | In chemo, NED | 6 | BC | None | |
| P410 | −3.23 | post chemo, NED | 24 | Immunoreactivity value at T1 was almost same as at T2 | Asso-R | FIG. 6C (a, b, lane 3) |
| P413 | −15.53 | In chemo, NED | 8 | BC | None | FIG. 6G (a, b, lane 3) |

| | | | | 5H6 | | |
|---|---|---|---|---|---|---|
| Sample ID | RecurInterval (T2) | Disease status at T2 | CA125 value at T2 | Comparison of level of 5H6 immunoreactivity at T2 and T1  BC represents immunoreactivity value below cutoff at T2 | Association of 5H6 immunoreactivity at T2 with recurrence status (Asso-R) | Western blot FIG. NO. |
| P178 | −4.20 | In chemo, NED | 203 | BC | None | FIG. 6B (a, b, lane 4) |
| P265 | −4.87 | In chemo, NED | 54 | Immunoreactivity value at T2 was 1.5 fold higher than at T1 | Asso-R | FIG. 6A (a, b, lane 4) |
| P295 | −5.77 | post chemo, NED | 18 | BC | None | |
| P283 | −13.60 | In chemo, NED | 22 | BC | None | |
| P300 | −3.73 | post chemo, NED | 12 | BC | None | |
| P326* | −4.30 | In chemo, stable disease | 41 | BC | None | FIG. 6E (a, b, lane 4) |
| P336 | −10.00 | post chemo, NED | 20 | BC | None | |
| P341 | −7.10 | In chemo, NED | 37 | BC | None | FIG. 6H (a, b, lane 4) |
| P342 | −3.30 | In chemo, NED | 5 | Immunoreactivity value at T1 was almost same as at T2 | Asso-R | |
| P356* | −9.07 | In chemo, tolerating treatment | 11 | BC | None | |
| P367* | −4.33 | In chemo, tolerating treatment | 29 | BC | None | FIG. 6F (a, b, lane 4) |
| P370 | −2.63 | In chemo, NED | 13 | BC | None | FIG. 6D (a, b, lane 4) |
| P386 | −17.27 | In chemo, Not specified | 16 | BC | None | |
| P392 | −5.93 | post chemo, NED | 9 | BC | None | |
| P376 | −9.93 | post chemo, NED | 7 | BC | None | |
| P378 | −12.37 | In chemo, NED | 9 | BC | None | |
| P393* | −5.03 | In chemo, EOD | 26 | BC | None | FIG. 6J (a, b, lane 4) |
| P398* | −10.30 | In chemo, EOD | 24 | BC | None | FIG. 6I (a, b, lane 4) |
| P400 | −4.50 | In chemo, NED | 6 | BC | None | |
| P410 | −3.23 | post chemo, NED | 24 | Immunoreactivity value at T1 was almost same as at T2 | Asso-R | FIG. 6C (a, b, lane 4) |
| P413 | −15.53 | In chemo, NED | 8 | BC | None | FIG. 6G (a, b, lane 4) |

Note:
Ovarian cancer patients with asterisk had evidence of disease months before the clinical recurrence;
NED: No evidence of disease;
EOD: Evidence of disease.
T1 represents time at ovarian cancer diagnosis;
T2 represents time in months before the clinical recurrence.

Association of Immunoreactivity of Antigens with Recurrence Status of Ovarian Cancer Patients Having Stable Disease During Monitoring Phase It was observed that immunoreactivity of Ro52, CDR2 and HARS antigens was most strongly associated with the recurrence status of 3/5, 3/5 and 4/5 ovarian cancer patients respectively (patients with asterisk shown in Table 9A) who had stable disease or under treatment at time T2 when their CA125 values were below or very close to the standard cutoff (35 U/ml). In contrast, the immunoreactivity values of 4B7, 4H4 and 5H6 were below cutoff for those patients.

Figure 6K:
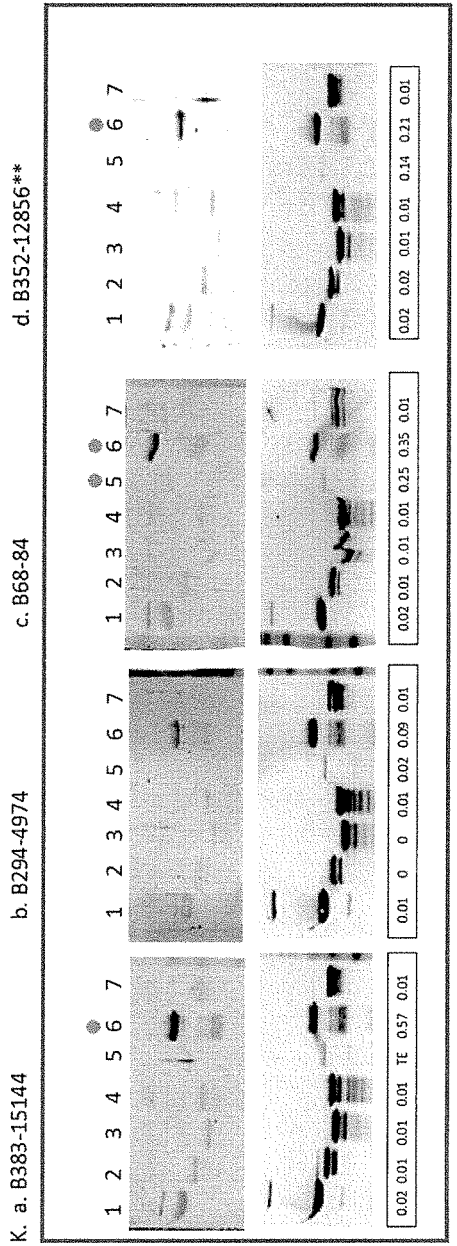
Figure 6L:
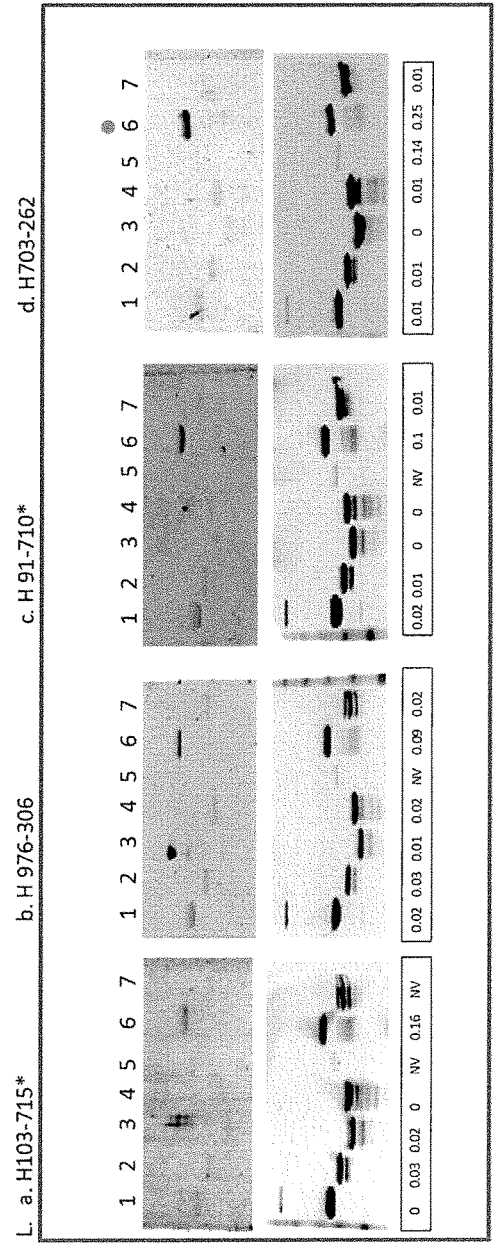

FIGS. 6A-6L show the reactivity of antigens with serum samples obtained from ovarian cancer patients at 3 different time points and women with other benign diseases and healthy women. For patients with double asterisks (**) in FIGS. 6A-6J, the western blot images were scanned at 6.5 for 800 nm wavelength for better visual purposes but the normalized signal intensity for each antigen listed in those images were obtained from the image scanned at intensity 7.5 for 800 nm wavelength. "M" means missing value for FIGS. 6A-6J. In each Figure, a, b and c represent images of immunoreactivity of antigens with the serum samples obtained from one ovarian cancer patient at different time points (T1: the baseline blood sample collected at time of diagnosis; T2: the blood sample collected approximately 3-15 months before the clinical recurrence, ideally with normal CA125 and no evidence of disease; T3: the sample collected as close as possible to clinical recurrence). In FIGS. 6K-6L, some samples have (*) beside their names and for those samples images were scanned at intensity 6.5 and quantified data were also obtained from the same images scanned at intensity 6.5 because of technical problems. "TE" means technical error and "NV" means negative value for FIGS. 6K-6L. FIGS. 6A-6J represent immunoreactivity of antigens with ovarian cancer patients, and FIGS. 6K-6L represent immunoreactivity of antigens with benign and healthy women. The dot on the antigen that is shown on the western blot image at time T2 shows that the normalized signal intensity for that particular antigen is above its cutoff. Underneath each western blot images in a panel, the normalized signal intensity value of each protein band is shown.

The reactivity of Ro52 antigen with ovarian cancer patient P326 was increased by 51.5 fold (fold change is calculated by dividing the normalized signal intensity of the antigen reactivity with the patient's serum IgG by the normalized signal intensity of the reactivity of His-tag at the N terminus of the antigen with anti-His-tag antibody) in contrast to immunoreactivity values of CDR2 or HARS that dropped by 1.5 fold or remained the same at 4.3 months when her CA125 value was only 41 U/ml before the clinical recurrence compared to the sero-reactivity at the time of diagnosis ((FIG. 6E, a, b, lanes 5, 6, and 1), Table 9A). For patient P367, the immunoreactivity of Ro52 and HARS was increased by 1.4 and 2 fold during the monitoring phases at 4.3 months (CA125 29 U/ml) before the clinical recurrence compared to their immunoreactivity at diagnosis ((FIG. 6F, a, b, lanes 5 and 1), Table 9A). The immunoreactivity of CDR2 antigen with P367 at times T1 and T2 remained almost the same, but the immunoreactivity value was 2.2 fold above the cutoff at T2. Although the patient P398 showed no increase in the serum reactivity with Ro52 protein at 10.3 months (CA125 level 24 U/ml) before the clinical recurrence over the time at diagnosis, the immunoreactivity of Ro52 was significantly higher, 6.7 fold above the cutoff at T2 ((FIG. 6I, a, b, lane 5), (Table 9A)). However, the immunoreactivity of HARS and CDR2 antigens with the patient P398 showed weaker to reactivity below cutoff (FIG. 6I, a, b, lanes 1 and 6), (Table 9A). The high reactivity of Ro52 with the patient P398 could be associated with the presence of residual tumor tissues after her first sub-optimal debulking, indicating that a high anti-Ro52 titer is needed for the equilibrium state when tumor cells remain in a dormant state before they develop into a highly progressive phenotype (87). Although the reactivity of HARS with the patient P393 remained almost the same at T1 and T2, the immunoreactivity of HARS was about 3 fold above its cutoff at T2 in contrast to Ro52 immunoreactivity that was below its cutoff at T2. The immunoreactivity of CDR2 antigen with the same patient P393 dropped by 1.4 fold at T2 (FIG. 6J, a, b, lanes 1, 5 and 6), (Table 9A). CDR2 expression is upregulated in ovarian tumors (71), so there is a possibility of sequestration by antigen blocking of newly synthesized Yo antibodies by circulating CDR2 protein. This can occur by the process of shedding, secretion of tumor antigens or antigens released due to apoptotic cell death as revealed by the proteomic analyses of 3 ovarian cancer cell lines by Faca et al. (72). These shed antigens can enter into circulation and can bind to their respective antibodies.

Association of Immunoreactivity of Antigens with Recurrence Status of Ovarian Cancer Patients Having No Evidence of Disease During Monitoring Phase The immunoreactivity of Ro52, CDR2, HARS, 4B7, 4H4, and 5H6 antigens showed association of recurrence with 8/16, 12/16, 10/16, 3/16, 3/16 and 3/16 ovarian cancer patients respectively who had no evidence of disease (NED), except one patient whose disease was not specified, at a median lead time of 5.85 months before the clinical recurrence at time T2 when most of the patients had CA125 levels below the standard cutoff (35 U/ml), with the exception of only one patient P178 who had a high CA125 value 203 U/ml at time T2 (Table 9(A-B)). For Ro52, HARS, 4B7 antigens, reactivity increased by 1.6, 1.6 and 1.4 fold with the patient P410, however, the immunoreactivity values of CDR2, 4H4 and 5H6 remained the same at T1 and T2 (individual immunoreactivity values of CDR2, 4H4 and 5H6 were 2, 6.6 and 4 fold higher than their cutoffs at time T2) during the monitoring phases at 3.23 months (CA125 24 U/ml) before the clinical recurrence compared to their time at diagnosis (FIG. 6C, a, b, lanes 5, 1, 2, 6, 3, and 4). The immunoreactivity of CDR2 and Ro52 antigens with the patient P370 dropped by 1.6 and 2 fold at recurrence interval of 2.63 months (CA125 13 U/ml). However, immunoreactivity of HARS remained the same at T1 and T2 (individual immunoreactivity was 3.6 fold higher that its cutoff at T2) ((FIG. 6D, a, b, lanes 6, 5 and 1), Table 9A). The drop in immunoreactivity of CDR2 and Ro52 (individual signal intensity values for both the antigens at time T2 were still 1.9 and 60 fold above cutoff) for P370 who had very short DFI 2.63 months could be related to the aggressive tumor growth that overpowered immune surveillance. Studies have indicated that tumor cells secrete immunosuppressive factors like IL-10, PEG2, TGFβ that suppress humoral immune effector cells (87). Tumor cells inhibit the expression of major histocompatibility complex I and upregulate the expression of inhibitory ligands such as PD-L1 resulting in inhibition of T cell signaling pathways (80). The patient P413 showed a decline in reactivity with HARS (immunoreactivity at T2 was below cutoff) and Ro52 revealed a 20.9 fold decrease in immunoreactivity (Ro52 immunoreactivity at T2 was 2.2 fold above the cutoff) at 15.5 months (CA125 8 U/ml) compared to the reactivity values at times when the patients were diagnosed (FIG. 6G, a, b, lanes 1 and 5). Although immunoreactivity of CDR2 with P413 remained same at T1 and T2, the immunoreactivity was 6.2 fold higher than its cutoff at T2 ((FIG. 6G, lanes 1, 5, and 6), Table 9A). Patient P413 responded well to first-line chemotherapy as indicated by her CA125 value 8 U/ml after undergoing optimal debulking that resulted in little to no microscopic residual tumor tissues during monitoring phase which can result in very low expression of Ro52 with concurrent reduction in the anti-Ro52 antibody titer. Titers of paraneoplastic antibodies have been shown to drop and even disappear with remission of the disease and concurrent reappearance of the antibodies takes place when the disease recurs (81). Both patients P265 and P341 showed an increase in CDR2 immunoreactivity by 2.4 and 1.7 fold and HARS immunoreactivity was increased by 2.2 and decreased by 1.4 fold at recurrence intervals of 4.87 months (CA125 level 54 U/ml) and 7.1 months (CA125 37 U/ml) before the radiologic evidence of recurrence compared to the values at their diagnosis times. In contrast, the immunoreactivity of Ro52 remained below cutoff for both the patients at time T2 ((FIG. 6A, 6H, a, b, lanes 6, 1 and 5), Table 9A). The patient P265 reacted with 4B7, 4H4 and 5H6 antigens with a fold increase in reactivity of 2, 1.7 and 1.5 at 4.87 months (CA125 level 54 U/ml) before the clinical recurrence compared to the time at diagnosis ((FIG. 6A, a, b, lanes 2, 3 and 4), Table 9B). The patient P178 reacted with 4B7 and 4H4 antigens and the fold increase in reactivity was 2.2 and 5.6 at 4.2 months before the clinical confirmation of recurrence compared to diagnosis time, however, the immunoreactivity of CDR2 and 5H6 at time T2 remained below the cutoff (FIG. 6B, a, b lanes 2, 3, 6 and 4). The immunoreactivity of Ro52 and HARS with the patient P178 remained same at T1 and T2, but only the immunoreactivity of Ro52 was 9.7 fold higher than the cutoff at time T2 (FIG. 6B, a, b, lanes 5, and 1).

Serological Screening of Antigens Using Healthy Women and Women with Benign Gynecological Diseases The 6 recombinant biomarkers were also tested for their immunoreactivity with the serum IgGs obtained from few healthy women and women with benign gynecological disease (they all had ovarian cysts/Benign Cystic Ovarian Neoplasms) (FIGS. 6K-6L). As the analyses of immunoreactivity of antigens with all the benign and healthy women is generally performed to achieve a higher specificity for the early diagnosis of ovarian cancer and not for predicting recurrence in a cohort of patients who are under surveillance during monitoring phase, only few western blot images of sero-reactivity of 6 antigens with benign and healthy women were shown for the present study. Only CDR2 antigen exhibited strong reactivity with a patient with benign disease, B383 (3.4 fold above cutoff) and with other benign and healthy women, the reactivity was in the range of 1.2 to 2 fold above the CDR2 cutoff. The frequency of CDR2 antigen reactivity with healthy and benign samples was higher more often than the rest of the 5 antigens.

The above results indicated that out of 6 recombinant antigens employed to assess their sero-reactivity with serum IgGs obtained from 21 ovarian cancer patients, 3 antigens, Ro52, CDR2 and HARS showed high frequency and strong reactivity, and the remaining 3 antigens, 4B7, 4H4 and 5H6 showed low frequency and moderate reactivity during the monitoring phase when most of the patients had CA125 levels above the standard cutoff (35 U/ml).

Determination of Sensitivity of Antigens Based on their Serological Immunoreactivity with Ovarian Cancer Patients for Prediction of Recurrence Before the Clinical Relapse The serologic reactivity of all the 6 recombinant antigens with serum IgGs obtained from 5 recurrent and 5 non-recurrent ovarian cancer patients (training set), and 21 recurrent ovarian cancer patients (test set) at time T2 before the clinical recurrence is shown in Table 8. The sensitivity of 6 antigens (single or in combination) to predict recurrence before the clinical recurrence in 21 ovarian cancer patients (test set) was determined.

Determination of Sensitivity Using One Antigen at a Time

Analyses of western blot immunoassays revealed that individually, Ro52, CDR2, HARS, 4B7, 4H4, and 5H6 antigens resulted in sensitivities of 52.4% (11/21), 71.4% (15/21), 66.7% (14/21), 14.3% (3/21), 14.3% (3/21) and 14.3% (3/21) respectively ((Tables 8-10)).

TABLE 10

Sensitivity of 6 antigens (in combinations of 1, 2 or 3 antigen panels) to predict recurrence prior to clinical recurrence in 21 ovarian cancer patients

| Antigen (Single or in combination of 2 or 3 antigen panels) | Sensitivity of antigen panels to predict recurrence in 21 ovarian cancer patients |
| --- | --- |
| Ro52 | 52.4% (11/21) |
| CDR2 | 71.4% (15/21) |
| HARS | 66.7% (14/21) |
| 4B7 | 14.3% (3/21) |
| 4H4 | 14.3% (3/21) |
| 5H6 | 14.3% (3/21) |
| Ro52 + CDR2 | 86% (18/21) |
| CDR2 + HARS | 81% (17/21) |
| Ro52 + HARS | 81% (17/21) |
| Ro52 + 5H6 | 62% (13/21) |
| CDR2 + 4B7 or CDR2 + 4H4 or CDR2 + 5H6 | 76% (16/21) |
| HARS + 5H6 | 71.4% (15/21) |
| Ro52 + CDR2 + 5H6 * | 90.5% (19/21) |
| HARS + CDR2 + 5H6 or Ro52 + CDR2 + HARS | 86% (18/21) |
| CDR2 + 4B7 + 5H6 or CDR2 + 4H4 + 5H6 | 80.9% (17/21) |
| Ro52 + 4B7 + 5H6 or Ro52 + 4H4 + 5H6 | 61.9% (13/21) |

Note:
* Combination of 3 antigens that resulted in highest sensitivity.

Determination of Sensitivity Using a Combination of any 2 Antigens at a Time

High sensitivities were observed for a combination of any 2 antigens, for example, 86% (18/21) for Ro52 and CDR2 antigens, 81% (17/21) for CDR2 and HARS antigens, 81% (17/21) for Ro52 and HARS respectively. Among the other combinations of antigens in a panel of 2 that resulted in moderate sensitivities were 62% (13/21) for 5H6 and Ro52 antigens, 76% (16/21) for each of the combinations of 4B7 and CDR2, 4H4 and CDR2, and 5H6 and CDR2 antigens, and 71.4% (15/21) for 5H6 and HARS antigens, respectively (Table 10).

Determination of Sensitivity Using a Combination of any 3 Antigens at a Time

Figure 7A:
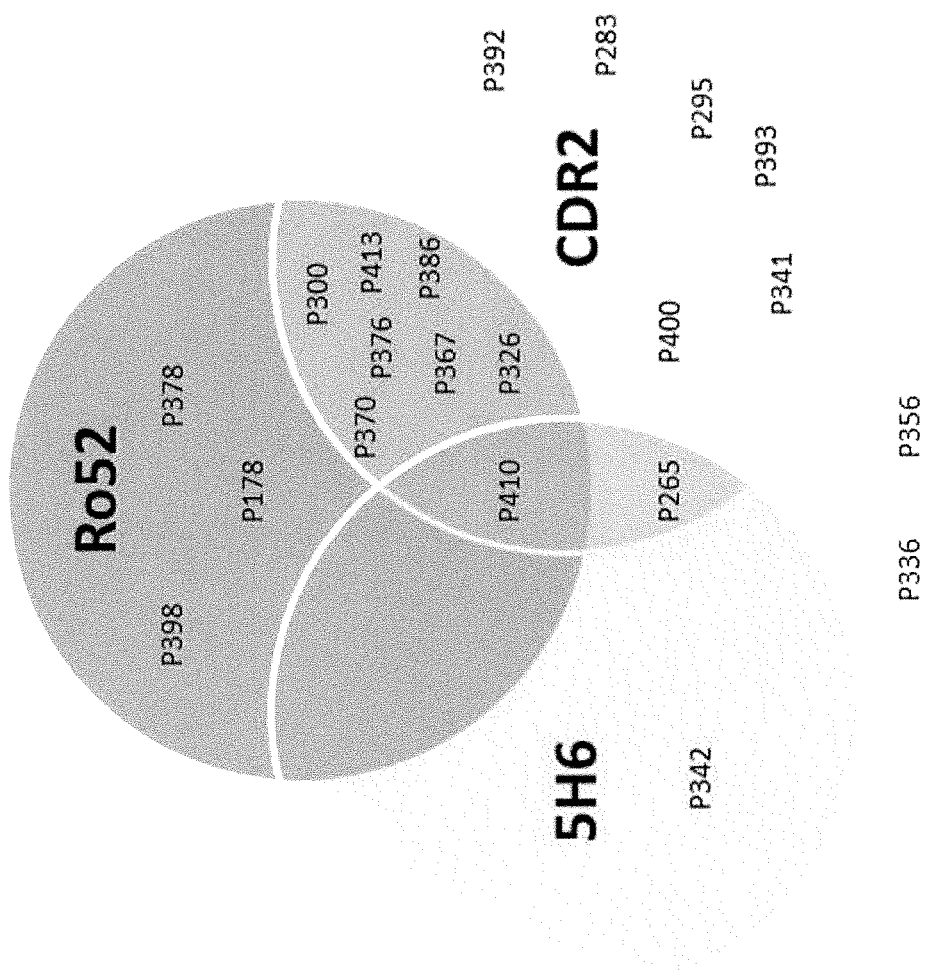
FIG. 7A is a Venn diagram of the combination of antigens Ro52, CDR2 and 5H6.
Figure 7B:
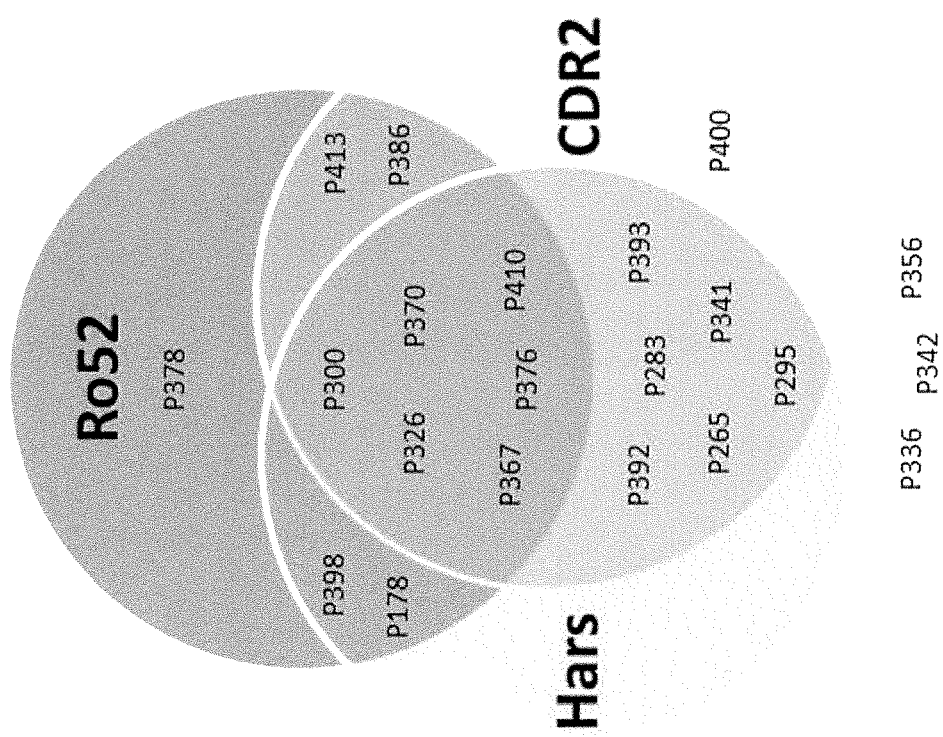
FIG. 7B is a Venn diagram of the combination of antigens Ro52, HARS, and CDR2 used for determining sensitivity for predicting ovarian cancer recurrence.

High sensitivities were observed for a combination of any 3 antigens, for example, 90.5% (19/21) for Ro52, CDR2 and 5H6 antigens (FIG. 7A), 86% (18/21) for HARS, CDR2 and 5H6 (Table 10), 86% (18/21) for Ro52, CDR2 and HARS (FIG. 7B), 80.9% (17/21) for CDR2, 4B7 and 5H6 or CDR2, 4H4 and 5H6 respectively (Table 10). Among the other panel of 3 antigens, moderate sensitivities were observed for 61.9% (13/21) for the combinations, Ro52, 4B7 and 5H6, or Ro52, 4H4 and 5H6 (Table 10).

The results indicate that a panel of 3 antigens, Ro52, CDR2 and 5H6 resulted in 90.5% sensitivity in predicting recurrence in 21 ovarian cancer patients at a median lead time of 5.03 months before the clinical relapse when CA125 levels were within the normal range (<35 U/ml). Although addition of HARS into that panel did not improve the sensitivity, it will be considered in the biomarker panel because first, it showed high frequency and strong reactivity with the ovarian cancer patients serum samples, second, it belongs to paraneoplastic antigen family and one of the previous antigen 4B7 showed peptide homology with HARS, and third, tumor microenvironment shows different levels of immunological suppression that is associated with varying levels of antibody response for different paraneoplastic antigens that in many cases complement each other. Out of 2 patients, P336, and P356, who appeared not to recur by these criteria, patient P336 had the third longest DFI of 15.1 months, there is a possibility of low antigen expression due to very low tumor burden that can result in low titers of antibodies within undetectable range.

DISCUSSION

Studies have shown that early onset of some paraneoplastic neurological symptoms is generally associated with the occurrence of onconeural antibodies that can serve as a diagnostic tool for a suspicion of ovarian cancer in asymptomatic high-risk patients carrying BRCA1/2 mutations (67, 90). Very few studies have shown the utility of these onconeural antibodies for disease monitoring in cancer patients. One study reported that antibodies to paraneoplastic antigen Mat showed a high sensitivity, specificity and accuracy (AUC between 0.734 and 0.816) to predict early recurrence in 124 patients who had small intestine neuroendocrine tumors (SI-NETs) (70).

In the present study, the immunoreactivity of 6 recombinant antigens was assessed with serum IgGs obtained from 21 ovarian cancer patients to predict recurrence at various times prior to clinical/radiologic evidence when the level of CA125 was below the normal range (35 U/ml). Three paraneoplastic antigens, Ro52 (SEQ ID NO: 25), CDR2 (SEQ ID NO: 27), and HARS (SEQ ID NO: 23) showed strong immunoreactivity association and the other 3 antigens, 4B7 (SEQ ID NO: 1), 4H4 (SEQ ID NO: 2), and 5H6 (SEQ ID NO: 3) exhibited moderate immunoreactivity association with the recurrence status of the 21 ovarian cancer patients, majority of which showed no elevation of CA125 (standard cutoff 35 U/ml) (Table (9A-9B)). Out of those 3 recombinant antigens, only 4B7 showed amino acid homology with the known paraneoplastic antigens, Histidyl t-RNA synthetase or HARS. Despite the homology to the C-terminal region with HARS protein, a similar frequency of reactivity was not observed between the recombinant 4B7 peptide and the full length HARS protein. A similar discordance was observed in most patients diagnosed with idiopathic myositis using epitope mapping of HARS protein which showed that 3 epitopes located at the N terminal region were mostly the reactive peptide segments (79). As dermatomyositis is often associated with the occurrence of ovarian cancer, several processes that cause epitope spreading resulting in broadening of anti-HARS specificity can also occur during the course of development of ovarian cancer (79). Although 4B7, 4H4 and 5H6 antigens encoded short peptides, exhibited low frequency and weak to moderate serological reactivity toward the ovarian cancer patients, these antigens still hold potential as biomarkers to monitor disease better than CA125 because of their high specificities against the 5 non-recurrent patients in the training set (Table 7). Those previous 3 biomarkers, 4B7, 4H4, and 5H6 were T7 phage encoded peptides and in the previous study their immunoreactivity was assessed by robotically printing the individual phage lysates on nitrocellulose membranes that were immunoscreened against patients' sera. Therefore, the immunoreactivities of these antigens assessed by the current study could not be compared with that of the previous ovarian cancer recurrence study because in the current study purified recombinant proteins in western blot immunoassay were used in contrast to the previous study in which T7 phage lysates of the individual phage clones were employed for immunoscreening on protein microarrays.

The paraneoplastic antigen Ro52 is an E3 ubiquitin ligase and elevated levels of circulating anti-Ro52 antibodies have been shown to cause autoimmunity in patients with Sjögren's syndrome and systemic lupus erythematosus (SLE) (64). Mechanistically Ro52 causes inflammation by the process of ubiquitination of interferon regulatory factors (64). The paraneoplastic antigen CDR2 has been shown to be expressed in Purkinje cells, testis and ovarian cancer (88). There is an association of onconeural anti-Yo antibodies (targets CDR2 antigen) with ovarian cancer patients who developed paraneoplastic cerebellar degeneration before cancer diagnosis (82). CDR2 is a cell cycle regulated protein that is highly expressed during mitosis in tumor cells. CDR2 interacts with c-Myc protein that can enhance gene transcription (84). The occurrence of anti-Jo-1 antibodies targeting HARS antigen has been associated with myositis, a paraneoplastic neurological disorder that causes inflammation and weakness in muscles. Twenty-five percent of patients who are diagnosed with polymyositis or dermatomyositis harbor anti-Jo-1 antibodies (77). Reports indicated that concurrent appearance of Jo-1 and Ro52 antibodies in patients diagnosed with antisynthetase syndrome (ASS) was associated with elevated risk of breast, ovarian, and esophagus cancers (78). This study employed serial ovarian cancer serum samples that were not used in the discovery of these biomarkers. However, in the present study, the training set population that was used to set the threshold of each antigen to achieve high specificity was comprised of only 5 recurrent and 5 non-recurrent ovarian cancer patients. The reasons for using a smaller size of patient population in the training set for the determination of threshold of each antigen were first, in the present study, it was desired to reevaluate the strength of immunoreactivity of the previous biomarkers, 4B7, 4H4, 5H6 (66) on the western blot platform to predict ovarian cancer recurrence prior to its clinical recurrence in patients who showed no elevation in CA125 level above its clinical threshold (35 U/ml) which led to using the same training set as before; second, for the previous study, it was possible to accrue few non-recurrent ovarian cancer patients (because the disease often recurs) who met patients' accrual criteria and those non-recurrent ovarian cancer patients were split into training and test sets which made the size of the training set smaller than expected (66); third, in the earlier immunoassay based studies, the same patient population of 5 recurrent and 5 non-recurrent ovarian cancer patients (current training set) as well as serum samples obtained from patients with paraneoplastic syndrome were immunoscreened with known paraneoplastic antigens to determine the immunoreactivity of those paraneoplastic antigens using paraneoplastic myositis line blots (EuroImmun, Morris Plains, N.J.) and Paraneoplastic Antigen line blots (Ravo Diagnostika, Freiburg, Germany). Similar immunoreactivity of HARS, Ro52 and CDR2 antigens with both recurrent and non-recurrent ovarian cancer patients in the training set was observed both on western blot (current study) and paraneoplastic antigen line blots (previous study) (data not shown). The immunoscreening analyses provided insights into usefulness of using true paraneoplastic protein antigens for early diagnosis and recurrence of ovarian cancer (data not shown). Therefore, the present study was enhanced by using the same ovarian cancer patient population in the training set to choose the threshold of each antigen that was applied to an independent test set patient population for the evaluation of their potential as biomarkers for prediction of ovarian cancer recurrence with a longer lead time than CA125. In addition, the test set study population did not have non-recurrent ovarian cancer patients. As the present study was a prospective-retrospective pilot study based on finding the utility of 6 biomarkers for prediction of ovarian cancer recurrence in patients prior to clinical recurrence, an independent patient population was needed in the test set who had CA125 levels below its threshold (35 U/ml) during the monitoring phase before clinical recurrence. The present study only focused on determining the sensitivity of the immunoassay used for prediction of ovarian cancer recurrence.

The DNA and protein sequences for the three paraneoplastic antigen markers are as follows:

His-HARS DNA sequence (SEQ ID NO: 22):
ATGGGCAGCAGCCATCATCATCATCATCATAGCAGCGGCCTGGTGCCGCG

CGGCAGCCATATGGGCAGCATGGCGGAACGCGCGGCGCTGGAAGAACTGG

TGAAACTGCAGGGCGAACGCGTGCGCGGCCTGAAACAGCAGAAAGCGAGC

GCGGAACTGATTGAAGAAGAAGTGGCGAAACTGCTGAAACTGAAAGCGCA

GCTGGGCCCGGATGAAAGCAAACAGAAATTTGTGCTGAAAACCCCGAAAG

GCACCCGCGATTATAGCCCGCGCCAGATGGCGGTGCGCGAAAAAGTGTTT

GATGTGATTATTCGCTGCTTTAAACGCCATGGCGCGGAAGTGATTGATAC

CCCGGTGTTTGAACTGAAAGAAACCCTGATGGGCAAATATGGCGAAGATA

GCAAACTGATTTATGATCTGAAAGATCAGGGCGGCGAACTGCTGAGCCTG

CGCTATGATCTGACCGTGCCGTTTGCGCGCTATCTGGCGATGAACAAACT

GACCAACATTAAACGCTATCATATTGCGAAAGTGTATCGCCGCGATAACC

CGGCGATGACCCGCGGCCGCTATCGCGAATTTTATCAGTGCGATTTTGAT

ATTGCGGGCAACTTTGATCCGATGATTCCGGATGCGGAATGCCTGAAAAT

TATGTGCGAAATTCTGAGCAGCCTGCAGATTGGCGATTTTCTGGTGAAAG

TGAACGATCGCCGCATTCTGGATGGCATGTTTGCGATTTGCGGCGTGAGC

GATAGCAAATTTCGCACCATTTGCAGCAGCGTGGATAAACTGGATAAAGT

GAGCTGGGAAGAAGTGAAAAACGAAATGGTGGGCGAAAAAGGCCTGGCGC

CGGAAGTGGCGGATCGCATTGGCGATTATGTGCAGCAGCATGGCGGCGTG

AGCCTGGTGGAACAGCTGCTGCAGGATCCGAAACTGAGCCAGAACAAACA

GGCGCTGGAAGGCCTGGGCGATCTGAAACTGCTGTTTGAATATCTGACCC

TGTTTGGCATTGATGATAAAATTAGCTTTGATCTGAGCCTGGCGCGCGGC

CTGGATTATTATACCGGCGTGATTTATGAAGCGGTGCTGCTGCAGACCCC

GGCGCAGGCGGGCGAAGAACCGCTGGGCGTGGGCAGCGTGGCGGCGGGCG

GCCGCTATGATGGCCTGGTGGGCATGTTTGATCCGAAAGGCCGCAAAGTG

CCGTGCGTGGGCCTGAGCATTGGCGTGGAACGCATTTTTAGCATTGTGGA

ACAGCGCCTGGAAGCGCTGGAAGAAAAAATTCGCACCACCGAAACCCAGG

TGCTGGTGGCGAGCGCGCAGAAAAAACTGCTGGAAGAACGCCTGAAACTG

GTGAGCGAACTGTGGGATGCGGGCATTAAAGCGGAACTGCTGTATAAAAA

AAACCCGAAACTGCTGAACCAGCTGCAGTATTGCGAAGAAGCGGGCATTC

CGCTGGTGGCGATTATTGGCGAACAGGAACTGAAAGATGGCGTGATTAAA

CTGCGCAGCGTGACCAGCCGCGAAGAAGTGGATGTGCGCCGCGAAGATCT

GGTGGAAGAAATTAAACGCCGCACCGGCCAGCCGCTGTGCATTTGC

His-HARS protein sequence (SEQ ID NO: 23):
MGSSHHHHHHSSGLVPRGSHMGSMAERAALEELVKLQGERVRGLKQQKAS

AELIEEEVAKLLKLKAQLGPDESKQKFVLKTPKGTRDYSPRQMAVREKVF

DVIIRCFKRHGAEVIDTPVFELKETLMGKYGEDSKLIYDLKDQGGELLSL

RYDLTVPFARYLAMNKLTNIKRYHIAKVYRRDNPAMTRGRYREFYQCDFD

IAGNFDPMIPDAECLKIMCEILSSLQIGDFLVKVNDRRILDGMFAICGVS

DSKFRTICSSVDKLDKVSWEEVKNEMVGEKGLAPEVADRIGDYVQQHGGV

SLVEQLLQDPKLSQNKQALEGLGDLKLLFEYLTLFGIDDKISFDLSLARG

LDYYTGVIYEAVLLQTPAQAGEEPLGVGSVAAGGRYDGLVGMFDPKGRKV

PCVGLSIGVERIFSIVEQRLEALEEKIRTTETQVLVASAQKKLLEERLKL

VSELWDAGIKAELLYKKNPKLLNQLQYCEEAGIPLVAIIGEQELKDGVIK

LRSVTSREEVDVRREDLVEEIKRRTGQPLCIC

His-T7-Ro52 DNA sequence (SEQ ID NO: 24):
ATGGCTAGCATGACTGGTGGACAGCAAATGGGTCGGGATCCGAATTCGAG

CTCCGTCGACCATCATCATCATCATCATATGGCTTCAGCAGCACGCTTGA

CAATGATGTGGGAGGAGGTCACATGCCCTATCTGCCTGGACCCCTTCGTG

GAGCCTGTGGGCATCGAGTGTGGCCACAGCTTCTGCCAGGAATGCATCTC

TCAGGTTGGGAAAGGTGGGGCAGCGTCTGTCCTGTGTGCCGGCAGCGCT

TTCTGCTCAAGAATCTCCGGCCCAATCGACAGCTAGCCAACATGGTGAAC

AACCTTAAAGAAATCAGCCAGGAGGCCAGAGAGGGCACACAGGGGGAACG

GTGTGCAGTGCATGGAGAGAGACTTCACCTGTTCTGTGAGAAAGATGGGA

AGGCCCTTTGCTGGGTATGTGCCCAGTCTCGGAAGCACCGTGACCACGCC

ATGGTCCCTCTTGAGGAGGCTGCACAGGAGTACCAGGAGAAGCTCCATGT

GGCATTAGGGGAACTGAGAAGAAAGCAGGAGTTGGCTGAGAAGTTGGAAG

TGGAAATTGCAATAAAGAGAGCAGACTGGAAGAAAACAGTGGAAACACAG

AAATCTAGGATTCACGCAGAGTTTGTGCAGCAAAAAAACTTCCTGGTTGA

AGAAGAACAGAGGCAGCTGCAGGAGCTGGAGAAGGATGAGAGGGAGCAGC

TGAGAATCCTGGGGGAGAAAGAGGCCAAGCTGGCCCAGCAGAGCCAGGCC

CTACAGGAGCTCATCTCAGAGCTAGATCGAAGGTGCCACAGCTCAGCACT

GGAACTGCTGCAGGAGGTGATAATTGTCCTGGAAAGGAGTGAGTCCTGGA

ACCTGAAGGACCTGGATATTACCTCTCCAGAACTCAGGAGTGTGTGCCAT

GTGCCAGGGCTGAAGAAGATGCTGAGGACATGTGCAGTCCACATCACTCT

GGATCCAGACACAGCCAATCCGTGGCTGATACTTTCAGAAGATCGGAGAC

AAGTGAGGCTTGGAGACACCCAGCAGAGCATACCTGGAAATGAAGAGAGA

TTTGATAGTTATCCTATGGTCCTGGGTGCCCAGCACTTTCACTCTGGAAA

ACATTACTGGGAGGTAGATGTGACAGGAAAGGAGGCCTGGGACCTGGGTG

```
TCTGCAGAGACTCTGTGCGCAGGAAGGGGCACTTTTTGCTTAGTTCCAAG

AGTGGCTTCTGGACATTTGGTTGTGGAACAAACAAAAATATGAGGCTGGC

ACCTACCCCAGACTCCCCTCCACCTTCAGGTGCCTCCATGCCAAGTTGG

GATTTTCCTGGACTATGAGGCTGGCATGGNCTCCTTCTACAACATCACTG

ACCATGGCTCCCTCATCTACTCCTTCTCTGAATGTGCCTTCACAGGACCT

CTGCGGCCCTTCTTCAGTCCTGGTTTCAATGATGGAGGAAAAAACACAGC

CCCTCTAACCCTCTGTCCACTGAATATTGGATCACAAGGATCCACTGACT

ATTG

His-T7-Ro52 protein sequence (SEQ ID NO: 25):
MASMTGGQQMGRDPNSSSVDHHHHHHMASAARLTMMWEEVTCPICLDPFV

EPVGIECGHSFCQECISQVGKGGGSVCPVCRQRFLLKNLRPNROLANMVN

NLKEISQEAREGTQGERCAVHGERLHLFCEKDGKALCWVCAQSRKHRDHA

MVPLEEAAQEYQEKLHVALGELRRKQELAEKLEVEIAIKRADWKKTVETQ

KSRIHAEFVQQKNFLVEEEQRQLQELEKDEREQLRILGEKEAKLAQQSQA

LQELISELDRRCHSSALELLQEVIIVLERSESWNLKDLDITSPELRSVCH

VPGLKKMLRTCAVHITLDPDTANPWLILSEDRRQVRLGDTQQSIPGNEER

FDSYPMVLGAQHFHSGKHYWEVDVTGKEAWDLGVCRDSVRRKGHFLLSSK

SGFWTIWLWNKQKYEAGTYPQTPLHLQVPPCQVGIFLDYEAGMXSFYNIT

DHGSLIYSFSECAFTGPLRPFFSPGFNDGGKNTAPLTLCPLNIGSQGSTD

Y

His-T7-CDR2 DNA sequence (SEQ ID NO: 26):
ATGGAATTCCATCATCATCATCATCATGGTGTTATGGCTAGCATGACTGG

TGGACAGCAAATGGGTATGCTGGCGGAAAACCTGGTAGAGGAGTTTGAGA

TGAAGGAGGACGAGCCGTGGTACGACCACCAGGACCTCCAGCAAGATCTT

CAACTTGCTGCTGAGCTTGGGAAGACATTACTGGATCGGAACACAGAGTT

GGAGGACTCTGTTCAGCAGATGTATACAACCAATCAGGAGCAGTTACAGG

AAATTGAGTATCTGACGAAGCAAGTGGAACTTCTACGGCAGATGAACGAA

CAACATGCAAAGGTTTATGAACAATTAGACGTCACAGCAAGGGAACTGGA

AGAAACAAATCAAAAGCTAGTTGCTGACAGCAAGGCCTCACAGCAAAAGA

TTCTGAGCCTGACTGAAACGATTGAATGCCTGCAAACCAACATTGATCAC

CTCCAGAGCCAAGTGGAGGAGCTGAAGTCATCTGGCCAAGGGGGAAGGAG

CCCGGGAAAGTGTGACCAGGAGAAACCGGCACCCAGCTTTGCATGTCTGA

AGGAGCTGTATGACCTCCGCCAACACTTCGTGTATGATCATGTGTTCGCT

GAGAAGATCACTTCCTTGCAAGGTCAGCCAAGCCCTGATGAAGAGGAAAA

TGAGCACTTGAAAAAAACAGTGACAATGTTGCAGGCCCAGCTGAGCCTGG

AGCGGCAGAAGCGGGTGACTATGGAGGAGGAATATGGGCTCGTGTTAAAG

GAGAACAGTGAACTGGAGCAGCAGCTGGGGGCCACAGGTGCCTACCGAGC

ACGGGCGCTGGAACTAGAGGCCGAGGTGGCAGAGATGCGACAGATGTTG

CAGTCAGAGCATCCATTTGTGAATGGAGTTGAGAAGCTGGTGCCAGACTC

TCTGTATGTTCCTTTCAAAGAGCCCAGCCAGAGCCTGCTGGAAGAGATGT

TCCTGACTGTGCCGGAATCACATAGAAAGCCTCTCAAGCGCAGCAGCAGT

GAGACGATCCTCAGCAGCTTGGCAGGGAGTGACATCGTGAAGGGCCACGA

GGAGACCTGCATCAGGAGGGCCAAGGCTGTGAAACAGAGGGGCATCTCCC

TTCTGCACGAAGTGGACACGCAGTACAGCGCCCTGAAGGTGAAGTATGAA

GAGTTGCTGAAGAAGTGCCAAGAGGAACAGGACTCCCTGTCACACAAGGC

TGTGCAGACCTCCAGGGCTGCAGCCAAGGACCTGACTGGAGTGAACGCCC

AGTCTGAGCCTGTTGCCAGCGGCTGGGAACTGGCCTCTGTCAACCCAGAG

CCCGTGAGTTCCCCTACAACACCTCCAGAATACAAAGCGTTGTTTAAGGA

GATCTTTAGTTGCATCAAGAAAACTAAGCAGGAAATAGATGAACAGAGAA

CAAAATACCGATCACTCTCCTCTCATTCT

His-T7-CDR2 protein sequence (SEQ ID NO: 27):
MEFHHHHHHGVMASMTGGQQMGMLAENLVEEFEMKEDEPWYDHQDLQQDL

QLAAELGKTLLDRNTELEDSVQQMYTTNQEQLQEIEYLTKQVELLRQMNE

QHAKVYEQLDVTARELEETNQKLVADSKASQQKILSLTETIECLQTNIDH

LQSQVEELKSSGQGGRSPGKCDQEKPAPSFACLKELYDLRQHFVYDHVFA

EKITSLQGQPSPDEEENEHLKKTVTMLQAQLSLERQKRVTMEEEYGLVLK

ENSELEQQLGATGAYRARALELEAEVAEMRQMLQSEHPFVNGVEKLVPDS

LYVPFKEPSQSLLEEMFLTVPESHRKPLKRSSSETILSSLAGSDIVKGHE

ETCIRRAKAVKQRGISLLHEVDTQYSALKVKYEELLKKCQEEQDSLSHKA

VQTSRAAAKDLTGVNAQSEPVASGWELASVNPEPVSSPTTPPEYKALFKE

IFSCIKKTKQEIDEQRTKYRSLSSHS
```

CONCLUSION

In conclusion, a combination of four antigens, Ro52, CDR2, HARS and 5H6 in a panel, showed a sensitivity of 90.5% in a western blot-based immunoassay for early prediction of recurrence in 21 ovarian cancer patients during the surveillance period when most of these patients had normal levels of CA125 level (cutoff 35 U/ml). The median lead time of prediction of recurrence was 5.03 months which was better than CA125. Paraneoplastic autoantibodies occur in asymptomatic cancer patients and can be used for early detection of cancer. Early prediction of recurrence before the cancer progresses to more aggressive phenotype can provide patients some time to be treated with conventional chemotherapy regimen to prevent recurrence of ovarian cancer.

While illustrative embodiments of the invention have been disclosed herein, it is understood that other embodiments and modifications may be apparent to those of ordinary skill in the art.

REFERENCES

1. Schink J C (1999) Current initial therapy of stage III and IV ovarian cancer: challenges for managed care. *Semin Oncol* 26: 2-7.
2. Mutch D G (2002) Surgical management of ovarian cancer. *Semin Oncol* 29: 3-8.
3. Schwartz P E (2002) Current diagnosis and treatment modalities for ovarian cancer. *Cancer Treat Res* 107: 99-118.
4. Chua T C, Liauw W, Robertson G, Morris D L (2010) Second-line treatment of first relapse recurrent ovarian cancer. *Aust N Z J Obstet Gynaecol* 50: 465-71.

5. Mann W J, Patsner B, Cohen H, Loesch M (1988) Preoperative serum CA125 levels in patients with surgical stage I invasive ovarian adenocarcinoma. *J Natl Cancer Inst* 80: 208-9.
6. Redman C W, Blackledge G R, Kelly K, Powell J, Buxton E J, Luesley D M (1990) Early serum CA125 response and outcome in epithelial ovarian cancer. *Eur J Cancer* 26: 593-6.
7. van der Burg M E, Lammes F B, Verweij J (1990) The role of CA 125 in the early diagnosis of progressive disease in ovarian cancer. *Ann Oncol* 1: 301-2.
8. Krivak T C, Tian C, Rose G S, Armstrong D K, Maxwell G L (2009) A Gynecologic Oncology Group Study of serum CA125 levels in patients with stage III optimally debulked ovarian cancer treated with intraperitoneal compared to intravenous chemotherapy: an analysis of patients enrolled in GOG 172. *Gynecol Oncol* 115:81-5.
9. Wilder J L, Pavlik E, Straughn J M et al. (2003) Clinical implications of a rising serum CA125 within the normal range in patients with epithelial ovarian cancer: a preliminary investigation. *Gynecol Oncol* 89: 233-5.
10. Anastasi E, Marchei G G, Viggiani V, Gennarini G, Frati L, Reale M G (2010) HE4: a new potential early biomarker for the recurrence of ovarian cancer. *Tumour Biol* 31: 113-9.
11. Schorge J O, Drake R D, Lee H et al. (2004) Osteopontin as an adjunct to CA125 in detecting recurrent ovarian cancer. *Clin Cancer Res* 10: 3474-8.
12. Tassi R A, Calza S, Ravaggi A et al. (2009) Mammaglobin B is an independent prognostic marker in epithelial ovarian cancer and its expression is associated with reduced risk of disease recurrence. *BMC Cancer* 9: 253.
13. Havrilesky U, Whitehead C M, Rubatt J M et al. (2008) Evaluation of biomarker panels for early stage ovarian cancer detection and monitoring for disease recurrence. *Gynecol Oncol* 110: 374-82.
14. Wysham W Z, Mhawech-Fauceglia P, Li H, Hays L, Syriac S, et al. (2012) BRCAness Profile of Sporadic Ovarian Cancer Predicts Disease Recurrence. *PLoS ONE* 7(1): e30042.
15. Li Y, Karjalainen A, Koskinen H et al. (2005) p53 autoantibodies predict subsequent development of cancer. *Int J Cancer* 114: 157-60.
16. Draghici S, Chatterjee M, Tainsky M A (2005) Epitomics: serum screening for the early detection of cancer on microarrays using complex panels of tumor antigens. *Expert Rev Mol Diagn* 5: 735-43.
17. Chatterjee M, Mohapatra S, Ionan A et al. (2006) Diagnostic markers of ovarian cancer by high-throughput antigen cloning and detection on arrays. *Cancer Res* 66: 1181-90.
18. Vogl F D, Stickeler E, Weyermann M et al. (1999) p53 autoantibodies in patients with primary ovarian cancer are associated with higher age, advanced stage and a higher proportion of p53-positive tumor cells. *Oncology* 57: 324-9.
19. Heubner M, Errico D, Kasimir-Bauer S, Herlyn D, Kimmig R, Wimberger P (2011) EpCAM-autoantibody levels in the course of disease of ovarian cancer patients. *Med Oncol* 28: 626-30.
20. Geysen H M, Rodda S J, Mason T J (1986) A priori delineation of a peptide which mimics a discontinuous antigenic determinant. *Mol Immunol* 23: 709-15.
21. Van Regenmortel M H V. Molecular dissection of protein antigens and the prediction of epitopes. In: Van Regenmortel M H V, Muller S (eds) Synthetic Peptides as Antigens. Amsterdam, Elsevier, 1999: pp. 1-78.
22. Meloen R H, Puijk W C, Slootstra J W (2000) Mimotopes: realization of an unlikely concept. *J Mol Recognit* 13: 352-9.
23. Hoess R, Brinkmann U, Handel T, Pastan I (1993) Identification of a peptide which binds to the carbohydrate-specific monoclonal antibody B3. *Gene* 128: 43-9.
24. Oldenburg K R, Loganathan D, Goldstein I J, Schultz P G, Gallop M A (1992) Peptide ligands for a sugar-binding protein isolated from a random peptide library. *Proc Natl Acad Sci USA* 89: 5393-7.
25. Tumenjargal S, Gellrich S, Linnemann T et al. (2003) Anti-tumor immune responses and tumor regression induced with mimotopes of a tumor-associated T cell epitope. *Eur J Immunol* 33: 3175-85.
26. Kieber-Emmons T, Luo P, Qiu J et al. (1999) Vaccination with carbohydrate peptide mimotopes promotes anti-tumor responses. *Nat Biotechnol* 17: 660-5.
27. Etzioni R, Urban N, Ramsey S et al. (2003) The case for early detection. *Nat Rev Cancer* 3: 243-52.
28. Makawita S, Diamandis E P (2010) The bottleneck in the cancer biomarker pipeline and protein quantification through mass spectrometry-based approaches: current strategies for candidate verification. *Clin Chem* 56: 212-22.
29. Mishra, A., Verma, M. Cancer Biomarkers: Are We Ready for the Prime Time? *Cancers* 2010, 2, 190-208.
30. Rustin al, Nelstrop A E, Tuxen M K, Lambert H E (1996) Defining progression of ovarian carcinoma during follow-up according to CA 125: a North Thames Ovary Group Study. *Ann Oncol* 7: 361-4.
31. Rustin G J, van der Burg M E, Griffin C L et al. (2010) Early versus delayed treatment of relapsed ovarian cancer (MRC OV05/EORTC 55955): a randomized trial. *Lancet* 376: 1155-63.
32. Diefenbach C S, Gnjatic S, Sabbatini P et al. (2008) Safety and immunogenicity study of NY-ESO-1b peptide and montanide ISA-51 vaccination of patients with epithelial ovarian cancer in high-risk first remission. *Clin Cancer Res* 14: 2740-8.
33. Gadducci A, Ferdeghini M, Buttitta F et al. (1999) Assessment of the prognostic relevance of serum anti-p53 antibodies in epithelial ovarian cancer. *Gynecol Oncol* 72: 76-81.
34. Kim 5, Cho H, Nam E J et al. (2010) Autoantibodies against stress-induced phosphoprotein-1 as a novel biomarker candidate for ovarian cancer. *Genes Chromosomes Cancer* 49: 585-95.
35. Naora H, Yang Y Q, Montz F J, Seidman J D, Kurman R J, Roden R B (2001) A serologically identified tumor antigen encoded by a homeobox gene promotes growth of ovarian epithelial cells. *Proc Natl Acad Sci USA* 98: 4060-5.
36. Odunsi K, Jungbluth A A, Stockert E et al. (2003) NY-ESO-1 and LAGE-1 cancertestis antigens are potential targets for immunotherapy in epithelial ovarian cancer. *Cancer Res* 63: 6076-83.
37. Wasmuth J J, Carlock L R. Chromosomal localization of human gene for histidyl-tRNA synthetase: clustering of genes encoding aminoacyl-tRNA synthetases on human chromosome 5. *Somat Cell Mol Genet* 1986; 12:513-517.
38. Howard O M, Dong H F, Yang D, Raben N, Nagaraju K, Rosen A, et al. Histidyl-tRNA synthetase and asparaginyl-tRNA synthetase, autoantigens in myositis, activate chemokine receptors on T lymphocytes and immature dendritic cells. *J Exp Med* 2002; 196:781-791.
39. Iavazzo C, Vorgias G, Papadakis M, Manikis P, Mavromatis I, Akrivos T. Polymyositis in a patient with recurring ovarian cancer and history of unrelated breast cancer. Arch Gynecol Obstet 2007; 276:81-84.
40. Ghosh A, Malak T M, Pool A J. Polymyositis and ovarian carcinoma: a case report. Arch Gynecol Obstet 2007; 275:195-197.
41. Sigurgeirsson B, Lindelof B, Edhag O, Allander E. Risk of cancer in patients with dermatomyositis or polymyositis. A population-based study. N Engl J Med 1992; 326:363-367.
42. Morris R T, Monk B J. Ovarian cancer: relevant therapy, not timing, is paramount. *Lancet* 2010; 376:1120-1122.
43. Sivori S, Parolini S, Marcenaro E, Castriconi R, Pende D, Millo R, et al. Involvement of natural cytotoxicity receptors in human natural killer cell-mediated lysis of neuroblastoma and glioblastoma cell lines. *J Neuroimmunol* 2000; 107:220-225.
44. Yu J, Tao Q Cheung K F, Jin H, Poon F F, Wang X, et al. Epigenetic identification of ubiquitin carboxyl-terminal hydrolase L1 as a functional tumor suppressor and biomarker for hepatocellular carcinoma and other digestive tumors. *Hepatology* 2008; 48:508-518.
45. Hatakeyama S, TRIM proteins and cancer. *Nat Rev Cancer* 2011; 11: 792-804.
46. Vitorino R, Alves R, Barros A, Caseiro A, Ferreira R, Lobo M C, Bastos A, Duarte J, Carvalho D, Santos L L, Amado F L. Finding new posttranslational modifications in salivary proline-rich proteins. *Proteomics* 2010; 10:3732-3742.
47. Suh E J, Kabir M H, Kang U B, Lee J W, Yu J, Noh D Y, Lee C. Comparative profiling of plasma proteome from breast cancer patients reveals thrombospondin-1 and BRWD3 as serological biomarkers. *Exp Mol Med* 2012; 44: 36-44.
48. Bai V U, Hwang O, Divine G W, Barrack E R, Menon M, Reddy G P, Hwang C. Averaged differential expression for the discovery of biomarkers in the blood of patients with prostate cancer, *PLoS One* 2012; 7:e34875.
49. Seko A, Kataoka F, Aoki D, Sakamoto M, Nakamura T, Hatae M, Yonezawa S, Yamashita K. Beta1,3-galactosyltransferases-4/5 are novel tumor markers for gynecological cancers, *Tumour Biol* 2009; 30: 43-50.
50. Lazarevich N L, Shavochkina D A, Fleishman D I, Kustova I F, Morozova O V, Chuchuev E S, Patyutko Y I. Deregulation of hepatocyte nuclear factor 4 (HNF4) as a marker of epithelial tumors progression. *Exp Oncol* 2010; 32:167-171.
51. J. Sambrook, E. F. Fritsch, and T. Maniatis, 1989, Molecular Cloning, A Laboratory Manual, 2d edition, Cold Spring Harbor, N.Y.
52. Current protocols in molecular biology, "Chapter 16: Protein Expression". F. M. Ausbel, et al. eds John Wiley & Sons, New York, 1994-2000.
53. Varma M M, Nolte D D, Inerowicz H D, Regnier F E. Spinning-disk self-referencing interferometry of antigen-antibody recognition. Optics Lett. 29: 950-952 (2004).
54. Khandadash R, Partouche S, Weiss A, et al. A Fully Synthetic "Phage-Like" System II: Synthesis and Live Cell Screening of Combinatorial Libraries of Peptides on Sub-Cellular Sized Microspheres. Open Optics J. 5 (Suppl 1-M3): 17-27 (2011).
55. Prestiagiacomo T, R. L. Humbel R L, Larida B, Binder S R. Multiplexed analysis of thirteen autoantibodies using the Bioplex 2200 fully automated immunoassay analyzer, in From Animal Models to Human Genetics: Research on the Induction of Pathenogencity of Autoantibodies, K. Conrad et al., eds. (Pabst Science Publishers, Lengerich, 2004), pp. 463-466.
56. Castel G, Chtéoui M, Heyd B, Tordo N. Phage Display of Combinatorial Peptide Libraries: Application to Antiviral Research. Molecules 16: 3499-3518 (2011).
57. Zhang H, et al. Peptide Epitopes Recognized by a Human Anti-Cryptococcal Glucuronoxylomannan Antibody. Immun. 65: 1158-1164 (1997).
58. Buchwald U K, et al. A Peptide Mimotope of Type 8 Pneumococcal Capsular Polysaccharide Induces a Protective Immune Response in Mice. Infect. Immun 75: 325-333 (2005)
59. Ganglberger E, et al. Allergen mimotopes for 3-dimensional epitope search and induction of antibodies inhibiting human IgE. FASEB J. 14: 2177-2184 (2000).
60. Fung-Kee-Fung M, Oliver T, Elit L, Oza A, Hirte H W, Bryson P. Optimal chemotherapy treatment for women with recurrent ovarian cancer. *Curr Oncol* 14:195-208 (2007).
61. Harlow E and Lane D. Antibodies: A Laboratory Manual. Cold Spring Harbor Laboratory, Cold Spring Harbor, 1988.
62. M. L. Albert, J. C. Darnell, A. Bender, L. M. Francisco, N. Bhardwaj, R. B. Darnell, Tumor-specific killer cells in paraneoplastic cerebellar degeneration, *Nat Med* 4 (1998), 1321-1324.
63. J. C. Antoine, L. Absi, J. Honnorat, J. M. Boulesteix, B. T. de, C. Vial, M. Butler, C. P. De, D. Michel, Antiamphiphysin antibodies are associated with various paraneoplastic neurological syndromes and tumors, *Arch Neurol* 56 (1999), 172-177.
64. L. A. Aqrawi, M. Kvarnstrom, K. A. Brokstad, R. Jonsson, K. Skarstein, M. Wahren-Herlenius, Ductal epithelial expression of Ro52 correlates with inflammation in salivary glands of patients with primary Sjogren's syndrome, *Clin Exp Immunol* 177 (2014), 244-252.
65. D. B. Atack, J. A. Nisker, H. H. Allen, E. R. Tustanoff, L. Levin, CA 125 surveillance and second-look laparotomy in ovarian carcinoma, *Am J Obstet Gynecol* 154 (1986), 287-289.
66. M. Chatterjee, G. Dyson, N. K. Levin, J. P. Shah, R. Morris, A. Munkarah, M. A. Tainsky, Tumor autoantibodies as biomarkers for predicting ovarian cancer recurrence, *Cancer Biomark* 11 (2012), 59-73.
67. M. Chatterjee, L. C. Hurley, M. A. Tainsky, Paraneoplastic antigens as biomarkers for early diagnosis of ovarian cancer, *Gynecol Oncol Rep* 21 (2017), 37-44.
68. M. Chatterjee, S. Mohapatra, A. Ionan, G. Bawa, R. Ali-Fehmi, X. Wang, J. Nowak, B. Ye, F. A. Nahhas, K. Lu, S. S. Witkin, D. Fishman, A. Munkarah, R. Morris, N. K. Levin, N. N. Shirley, G. Tromp, J. Abrams, S. Draghici, M. A. Tainsky, Diagnostic markers of ovarian cancer by high-throughput antigen cloning and detection on arrays, *Cancer Res* 66 (2006), 1181-1190.
69. M. Chatterjee, M. A. Tainsky, Autoantibodies as biomarkers for ovarian cancer, *Cancer Biomark* 8 (2010), 187-201.
70. T. Cui, M. Hurtig, G. Elgue, S. C. Li, G. Veronesi, A. Essaghir, J. B. Demoulin, G. Pelosi, M. Alimohammadi, K. Oberg, V. Giandomenico, Paraneoplastic antigen Mat autoantibodies as specific blood biomarkers for detection of early recurrence of small intestine neuroendocrine tumors, *PLoS One* 5 (2010), e16010.
71. J. C. Darnell, M. L. Albert, R. B. Darnell, Cdr2, a target antigen of naturally occurring human tumor immunity, is widely expressed in gynecological tumors, *Cancer Res* 60 (2000), 2136-2139.
72. V. M. Faca, A. P. Ventura, M. P. Fitzgibbon, S. R. Pereira-Faca, S. J. Pitteri, A. E. Green, R. C. Ireton, Q.

Zhang, H. Wang, K. C. O'Briant, C. W. Drescher, M. Schummer, M. W. McIntosh, B. S. Knudsen, S. M. Hanash, Proteomic analysis of ovarian cancer cells reveals dynamic processes of protein secretion and shedding of extra-cellular domains, *PLoS One* 3 (2008), e2425.
73. F. Ghaemmaghami, Z. M. Karimi, B. Hamedi, High levels of CA125 (over 1,000 IU/ml) in patients with gynecologic disease and no malignant conditions: three cases and literature review, *Arch Gynecol Obstet* 276 (2007), 559-561.
74. V. Guarneri, E. Barbieri, M. V. Dieci, F. Piacentini, P. Conte, Timing for starting second-line therapy in recurrent ovarian cancer, *Expert Rev Anticancer Ther* 11 (2011), 49-55.
75. N. Guo, Z. Peng, Does serum CA125 have clinical value for follow-up monitoring of postoperative patients with epithelial ovarian cancer? Results of a 12-year study, *J Ovarian Res* 10 (2017), 14.
76. R. Hoftberger, L. Sabater, F. Velasco, R. Ciordia, J. Dalmau, F. Graus, Carbonic anhydrase-related protein VIII antibodies and paraneoplastic cerebellar degeneration, *Neuropathol Appl Neurobiol* 40 (2014), 650-653.
77. O. M. Howard, H. F. Dong, D. Yang, N. Raben, K. Nagaraju, A. Rosen, L. Casciola-Rosen, M. Hartlein, M. Kron, D. Yang, K. Yiadom, S. Dwivedi, P. H. Plotz, J. J. Oppenheim, Histidyl-tRNA synthetase and asparaginyl-tRNA synthetase, autoantigens in myositis, activate chemokine receptors on T lymphocytes and immature dendritic cells, *J Exp Med* 196 (2002), 781-791.
78. I. Marie, P. Y. Hatron, S. Dominique, P. Cherin, L. Mouthon, J. F. Menard, H. Levesque, F. Jouen, Short-term and long-term outcome of anti-Jo1-positive patients with anti-Ro52 antibody, *Semin Arthritis Rheum* 41 (2012), 890-899.
79. A. Martin, M. J. Shulman, F. W. Tsui, Epitope studies indicate that histidyl-tRNA synthetase is a stimulating antigen in idiopathic myositis, *FASEB J* 9 (1995), 1226-1233.
80. I. Mellman, G. Coukos, G. Dranoff, Cancer immunotherapy comes of age, *Nature* 480 (2011), 480-489.
81. F. W. Miller, S. A. Twitty, T. Biswas, P. H. Plotz, Origin and regulation of a disease-specific autoantibody response. Antigenic epitopes, spectrotype stability, and isotype restriction of anti-Jo-1 autoantibodies, *J Clin Invest* 85 (1990), 468-475.
82. S. E. Monstad, A. Storstein, A. Dorum, A. Knudsen, P. E. Lonning, H. B. Salvesen, J. H. Aarseth, C. A. Vedeler, Yo antibodies in ovarian and breast cancer patients detected by a sensitive immunoprecipitation technique, *Clin Exp Immunol* 144 (2006), 53-58.
83. R. T. Morris, B. J. Monk, Ovarian cancer: relevant therapy, not timing, is paramount, *Lancet* 376 (2010), 1120-1122.
84. K. J. O'Donovan, J. Diedler, G. C. Couture, J. J. Fak, R. B. Darnell, The onconeural antigen cdr2 is a novel APC/C target that acts in mitosis to regulate c-myc target genes in mammalian tumor cells, *PLoS One* 5 (2010), e10045.
85. L. C. Pelosof, D. E. Gerber, Paraneoplastic syndromes: an approach to diagnosis and treatment, *Mayo Clin Proc* 85 (2010), 838-854.
86. G. J. Rustin, M. E. van der Burg, C. L. Griffin, D. Guthrie, A. Lamont, G. C. Jayson, G. Kristensen, C. Mediola, C. Coens, W. Qian, M. K. Parmar, A. M. Swart, Early versus delayed treatment of relapsed ovarian cancer (MRC OV05/EORTC 55955): a randomised trial, *Lancet* 376 (2010), 1155-1163.
87. R. D. Schreiber, L. J. Old, M. J. Smyth, Cancer immunoediting: integrating immunity's roles in cancer suppression and promotion, *Science* 331 (2011), 1565-1570.
88. C. Totland, N. K. Aarskog, T. W. Eichler, M. Haugen, J. K. Nostbakken, S. E. Monstad, H. B. Salvesen, S. Mork, B. I. Haukanes, C. A. Vedeler, CDR2 antigen and Yo antibodies, *Cancer Immunol Immunother* 60 (2011), 283-289.
89. Z. J. Yang, B. B. Zhao, L. Li, The significance of the change pattern of serum CA125 level for judging prognosis and diagnosing recurrences of epithelial ovarian cancer, *J Ovarian Res* 9 (2016), 57.
90. Q. Zhu, S. X. Han, C. Y. Zhou, M. J. Cai, L. P. Dai, J. Y. Zhang, Autoimmune response to PARP and BRCA1/BRCA2 in cancer, *Oncotarget* 6 (2015), 11575-11584.

What is claimed is:

1. A panel of polypeptide marker antigens for detecting the presence of autoantibody biomarkers associated with a risk of ovarian cancer recurrence from a patient sample, said panel of polypeptide marker antigens including paraneoplastic marker antigens of SEQ ID NO: 23, SEQ ID NO: 25, and SEQ ID NO: 27, each of said polypeptide marker antigens specifically binding at least one of said autoantibody biomarkers in said patient sample, each of said polypeptide marker antigens being further defined as an isolated phage display antigen clone including His and T7 tags.

2. The panel of claim 1, further including at least one marker antigen selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and combinations thereof.

* * * * *

SEQUENCE LISTING

<160> NUMBER OF SEQ ID NOS: 27

<210> SEQ ID NO 1
<211> LENGTH: 24
<212> TYPE: PRT
<213> ORGANISM: Homo sapiens

<400> SEQUENCE: 1

Glu Val Asp Val Arg Arg Glu Asp Leu Val Glu Glu Ile Lys Arg Arg
1               5                   10                  15

Thr Gly Gln Pro Leu Cys Ile Cys
            20

<210> SEQ ID NO 2
<211> LENGTH: 8
<212> TYPE: PRT
<213> ORGANISM: Homo sapiens

<400> SEQUENCE: 2

Pro Gly Cys Ser Thr Thr Leu Ser
1               5

<210> SEQ ID NO 3
<211> LENGTH: 11
<212> TYPE: PRT
<213> ORGANISM: Homo sapiens

<400> SEQUENCE: 3

Asn Ser Phe Leu Met Thr Ser Ser Lys Pro Arg
1               5                   10

<210> SEQ ID NO 4
<211> LENGTH: 8
<212> TYPE: PRT
<213> ORGANISM: Homo sapiens

<400> SEQUENCE: 4

Glu Asn Val Leu Val Gln Thr Asn
1               5

<210> SEQ ID NO 5
<211> LENGTH: 4
<212> TYPE: PRT
<213> ORGANISM: Homo sapiens

<400> SEQUENCE: 5

Glu Leu His Asn
1

<210> SEQ ID NO 6
<211> LENGTH: 11
<212> TYPE: PRT
<213> ORGANISM: Homo sapiens

<400> SEQUENCE: 6

Leu Gly Ser Asp Glu Arg Arg His Arg Ala Pro
1               5                   10

<210> SEQ ID NO 7
<211> LENGTH: 18
<212> TYPE: PRT
<213> ORGANISM: Homo sapiens

<400> SEQUENCE: 7

Val Asp Glu Glu Asp Met Met Asn Gln Val Leu Gln Arg Ser Ile Ile
1               5                   10                  15

Asp Gln

<210> SEQ ID NO 8
<211> LENGTH: 28
<212> TYPE: PRT
<213> ORGANISM: Homo sapiens

<400> SEQUENCE: 8

Val Gln Ala Gln Gln Arg Ser Ala Pro Ala Arg Ala Ala Arg Ala Gly
1               5                   10                  15

His Pro Glu Ala Gly Ala Gly Met Glu Gly Ala Gly
                20                  25

<210> SEQ ID NO 9
<211> LENGTH: 10
<212> TYPE: PRT
<213> ORGANISM: Homo sapiens

<400> SEQUENCE: 9

```
-continued

Pro Lys Thr Met Thr Gln Asn Ser Phe Gly
1               5                   10

<210> SEQ ID NO 10
<211> LENGTH: 6
<212> TYPE: PRT
<213> ORGANISM: Homo sapiens

<400> SEQUENCE: 10

Tyr Ala Cys Leu Lys Asp
1               5

<210> SEQ ID NO 11
<211> LENGTH: 76
<212> TYPE: DNA
<213> ORGANISM: Artificial Sequence
<220> FEATURE:
<223> OTHER INFORMATION: Primer

<400> SEQUENCE: 11
cgccgccgcg gatccgcgac gcgtcgacca tcatcatcat catcatatgg ctagcatgac    60
tggtggacag caaatg                                                    76

<210> SEQ ID NO 12
<211> LENGTH: 91
<212> TYPE: DNA
<213> ORGANISM: Artificial Sequence
<220> FEATURE:
<223> OTHER INFORMATION: Primer

<400> SEQUENCE: 12
atagaatcac attaaacagg aattccatat ggaattccat catcatcatc atcatggtgt    60
tatggctagc atgactggtg gacagcaaat g                                   91

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
cctcctttca gcaaaaaacc cc                                             22

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
tgctaaggac aacgttatcg g                                              21

<210> SEQ ID NO 15
<211> LENGTH: 40
<212> TYPE: DNA
<213> ORGANISM: Artificial Sequence
<220> FEATURE:
<223> OTHER INFORMATION: Primer

<400> SEQUENCE: 15
agatctcgat cccgcgaaat taatacgact cactataggg                          40
```

```
<210> SEQ ID NO 16
<211> LENGTH: 120
<212> TYPE: DNA
<213> ORGANISM: Artificial Sequence
<220> FEATURE:
<223> OTHER INFORMATION: Primer

<400> SEQUENCE: 16
atcacattaa acaggaattc catatggaat tccatcatca tcatcatcat ggtgttatgg      60
ctagcatgac tggtggacag caaatgggtg ggatgctggc ggaaaacctg gtagaggagt    120

<210> SEQ ID NO 17
<211> LENGTH: 60
<212> TYPE: DNA
<213> ORGANISM: Artificial Sequence
<220> FEATURE:
<223> OTHER INFORMATION: Primer

<400> SEQUENCE: 17
cgcggatccc gctcgagcgg tagagctaga ggttcaatta agaatgagag gagagtgatc     60

<210> SEQ ID NO 18
<211> LENGTH: 36
<212> TYPE: DNA
<213> ORGANISM: Artificial Sequence
<220> FEATURE:
<223> OTHER INFORMATION: Primer

<400> SEQUENCE: 18
aggaatatgg gctcgtgtta aaggagaaca gtgaac                               36

<210> SEQ ID NO 19
<211> LENGTH: 83
<212> TYPE: DNA
<213> ORGANISM: Artificial Sequence
<220> FEATURE:
<223> OTHER INFORMATION: Primer

<400> SEQUENCE: 19
cgccgccgcg gatccgcgac gcgtcgacca tcatcatcat catcatatgg cttcagcagc     60
acgcttgaca atgatgtggg agg                                             83

<210> SEQ ID NO 20
<211> LENGTH: 54
<212> TYPE: DNA
<213> ORGANISM: Artificial Sequence
<220> FEATURE:
<223> OTHER INFORMATION: Primer

<400> SEQUENCE: 20
cgcggatccc gctcgagcgg ccatcaatag tcagtggatc cttgtgatcc aata           54

<210> SEQ ID NO 21
<211> LENGTH: 42
<212> TYPE: DNA
<213> ORGANISM: Artificial Sequence
<220> FEATURE:
<223> OTHER INFORMATION: Primer

<400> SEQUENCE: 21
tccatgccaa gttgggattt tcctggacta tgaggctggc at                        42

<210> SEQ ID NO 22
<211> LENGTH: 1596
<212> TYPE: DNA
```

<213> ORGANISM: Homo sapiens

<400> SEQUENCE: 22

```
atgggcagca gccatcatca tcatcatcat agcagcggcc tggtgccgcg cggcagccat       60
atgggcagca tggcggaacg cgcggcgctg aagaactgg tgaaactgca gggcgaacgc       120
gtgcgcggcc tgaaacagca gaaagcgagc gcggaactga ttgaagaaga gtggcgaaa       180
ctgctgaaac tgaaagcgca gctgggcccg atgaaagcaa acagaaatt tgtgctgaaa       240
accccgaaag gcacccgcga ttatagcccg cgccagatgg cggtgcgcga aaaagtgttt      300
gatgtgatta ttcgctgctt taaacgccat ggcgcggaag tgattgatac cccggtgttt      360
gaactgaaag aaaccctgat gggcaaatat ggcgaagata gcaaactgat ttatgatctg      420
aaagatcagg gcggcgaact gctgagcctg cgctatgatc tgaccgtgcc gtttgcgcgc      480
tatctggcga tgaacaaact gaccaacatt aaacgctatc atattgcgaa agtgtatcgc      540
cgcgataacc cggcgatgac ccgcggccgc tatcgcgaat tttatcagtg cgattttgat      600
attgcgggca actttgatcc gatgattccg gatgcggaat gcctgaaaat tatgtgcgaa      660
attctgagca gcctgcagat tggcgatttt ctggtgaaag tgaacgatcg ccgcattctg      720
gatggcatgt ttgcgatttg cggcgtgagc gatagcaaat ttcgcaccat ttgcagcagc      780
gtggataaac tggataaagt gagctgggaa gaagtgaaaa acgaaatggt gggcgaaaaa      840
ggcctggcgc cggaagtggc ggatcgcatt ggcgattatg tgcagcagca tggcggcgtg      900
agcctggtgg aacagctgct gcaggatccg aaactgagcc agaacaaaca ggcgctggaa      960
ggcctgggca tctgaaaact gctgtttgaa tatctgaccc tgtttggcat tgatgataaa     1020
attagctttg atctgagcct ggcgcgcggc ctggattatt taccggcgt gatttatgaa     1080
gcggtgctgc tgcagacccc ggcgcaggcg ggcgaagaac cgctgggcgt gggcagcgtg     1140
gcggcgggcg gccgctatga tggcctggtg ggcatgtttg atccgaaagg ccgcaaagtg     1200
ccgtgcgtgg gcctgagcat tggcgtggaa cgcatttta gcattgtgga acagcgcctg     1260
gaagcgctgg aagaaaaat tcgcaccacc gaaacccagg tgctggtggc gagcgcgcag     1320
aaaaaactgc tggaagaacg cctgaaactg gtgagcgaac tgtgggatgc gggcattaaa     1380
gcggaactgc tgtataaaaa aaacccgaaa ctgctgaacc agctgcagta ttgcgaagaa     1440
gcgggcattc cgctggtggc gattattggc gaacaggaac tgaaagatgg cgtgattaaa     1500
ctgcgcagcg tgaccagccg cgaagaagtg gatgtgcgcc gcgaagatct ggtggaagaa     1560
attaaacgcc gcaccggcca gccgctgtgc atttgc                              1596
```

<210> SEQ ID NO 23
<211> LENGTH: 532
<212> TYPE: PRT
<213> ORGANISM: Homo sapiens

<400> SEQUENCE: 23

```
Met Gly Ser Ser His His His His His Ser Ser Gly Leu Val Pro
1               5                   10                  15

Arg Gly Ser His Met Gly Ser Met Ala Glu Arg Ala Ala Leu Glu Glu
            20                  25                  30

Leu Val Lys Leu Gln Gly Glu Arg Val Arg Gly Leu Lys Gln Gln Lys
        35                  40                  45

Ala Ser Ala Glu Leu Ile Glu Glu Val Ala Lys Leu Leu Lys Leu
    50                  55                  60

Lys Ala Gln Leu Gly Pro Asp Glu Ser Lys Gln Lys Phe Val Leu Lys
```

```
            65                  70                  75                  80
Thr Pro Lys Gly Thr Arg Asp Tyr Ser Pro Arg Gln Met Ala Val Arg
                    85                  90                  95

Glu Lys Val Phe Asp Val Ile Ile Arg Cys Phe Lys Arg His Gly Ala
                100                 105                 110

Glu Val Ile Asp Thr Pro Val Phe Glu Leu Lys Glu Thr Leu Met Gly
                115                 120                 125

Lys Tyr Gly Glu Asp Ser Lys Leu Ile Tyr Asp Leu Lys Asp Gln Gly
            130                 135                 140

Gly Glu Leu Leu Ser Leu Arg Tyr Asp Leu Thr Val Pro Phe Ala Arg
145                 150                 155                 160

Tyr Leu Ala Met Asn Lys Leu Thr Asn Ile Lys Arg Tyr His Ile Ala
                165                 170                 175

Lys Val Tyr Arg Arg Asp Asn Pro Ala Met Thr Arg Gly Arg Tyr Arg
                180                 185                 190

Glu Phe Tyr Gln Cys Asp Phe Asp Ile Ala Gly Asn Phe Asp Pro Met
            195                 200                 205

Ile Pro Asp Ala Glu Cys Leu Lys Ile Met Cys Glu Ile Leu Ser Ser
210                 215                 220

Leu Gln Ile Gly Asp Phe Leu Val Lys Val Asn Asp Arg Arg Ile Leu
225                 230                 235                 240

Asp Gly Met Phe Ala Ile Cys Gly Val Ser Asp Ser Lys Phe Arg Thr
                245                 250                 255

Ile Cys Ser Ser Val Asp Lys Leu Asp Lys Val Ser Trp Glu Glu Val
                260                 265                 270

Lys Asn Glu Met Val Gly Glu Lys Gly Leu Ala Pro Glu Val Ala Asp
            275                 280                 285

Arg Ile Gly Asp Tyr Val Gln Gln His Gly Gly Val Ser Leu Val Glu
            290                 295                 300

Gln Leu Leu Gln Asp Pro Lys Leu Ser Gln Asn Lys Gln Ala Leu Glu
305                 310                 315                 320

Gly Leu Gly Asp Leu Lys Leu Phe Glu Tyr Leu Thr Leu Phe Gly
                325                 330                 335

Ile Asp Asp Lys Ile Ser Phe Asp Leu Ser Leu Ala Arg Gly Leu Asp
                340                 345                 350

Tyr Tyr Thr Gly Val Ile Tyr Glu Ala Val Leu Leu Gln Thr Pro Ala
            355                 360                 365

Gln Ala Gly Glu Glu Pro Leu Gly Val Gly Ser Val Ala Ala Gly Gly
            370                 375                 380

Arg Tyr Asp Gly Leu Val Gly Met Phe Asp Pro Lys Gly Arg Lys Val
385                 390                 395                 400

Pro Cys Val Gly Leu Ser Ile Gly Val Glu Arg Ile Phe Ser Ile Val
                405                 410                 415

Glu Gln Arg Leu Glu Ala Leu Glu Glu Lys Ile Arg Thr Thr Glu Thr
            420                 425                 430

Gln Val Leu Val Ala Ser Ala Gln Lys Lys Leu Leu Glu Glu Arg Leu
            435                 440                 445

Lys Leu Val Ser Glu Leu Trp Asp Ala Gly Ile Lys Ala Glu Leu Leu
            450                 455                 460

Tyr Lys Lys Asn Pro Lys Leu Leu Asn Gln Leu Gln Tyr Cys Glu Glu
465                 470                 475                 480

Ala Gly Ile Pro Leu Val Ala Ile Ile Gly Glu Gln Glu Leu Lys Asp
                485                 490                 495
```

```
Gly Val Ile Lys Leu Arg Ser Val Thr Ser Arg Glu Glu Val Asp Val
            500                 505                 510

Arg Arg Glu Asp Leu Val Glu Glu Ile Lys Arg Arg Thr Gly Gln Pro
        515                 520                 525

Leu Cys Ile Cys
    530

<210> SEQ ID NO 24
<211> LENGTH: 1505
<212> TYPE: DNA
<213> ORGANISM: Homo sapiens
<220> FEATURE:
<221> NAME/KEY: misc_feature
<222> LOCATION: (1331)..(1331)
<223> OTHER INFORMATION: n is a, c, g, or t

<400> SEQUENCE: 24
```

| | | | | | |
|---|---|---|---|---|---|
| atggctagca | tgactggtgg | acagcaaatg | ggtcgggatc | cgaattcgag | ctccgtcgac | 60 |
| catcatcatc | atcatcatat | ggcttcagca | gcacgcttga | caatgatgtg | ggaggaggtc | 120 |
| acatgcccta | tctgcctgga | ccccttcgtg | gagcctgtgg | gcatcgagtg | tggccacagc | 180 |
| ttctgccagg | aatgcatctc | tcaggttggg | aaaggtgggg | gcagcgtctg | tcctgtgtgc | 240 |
| cggcagcgct | ttctgctcaa | gaatctccgg | cccaatcgac | agctagccaa | catggtgaac | 300 |
| aaccttaaag | aaatcagcca | ggaggccaga | gagggcacac | aggggggaacg | tgtgcagtg | 360 |
| catggagaga | gacttcacct | gttctgtgag | aaagatggga | aggccctttg | ctgggtatgt | 420 |
| gcccagtctc | ggaagcaccg | tgaccacgcc | atggtccctc | ttgaggaggc | tgcacaggag | 480 |
| taccaggaga | agctccatgt | ggcattaggg | gaactgagaa | gaaagcagga | gttggctgag | 540 |
| aagttggaag | tggaaattgc | aataaagaga | gcagactgga | agaaaacagt | ggaaacacag | 600 |
| aaatctagga | ttcacgcaga | gtttgtgcag | caaaaaaact | tcctggttga | agaagaacag | 660 |
| aggcagctgc | aggagctgga | gaaggatgag | agggagcagc | tgagaatcct | ggggagaaa | 720 |
| gaggccaagc | tggcccagca | gagccaggcc | ctacaggagc | tcatctcaga | gctagatcga | 780 |
| aggtgccaca | gctcagcact | ggaactgctg | caggaggtga | taattgtcct | ggaaaggagt | 840 |
| gagtcctgga | acctgaagga | cctggatatt | acctctccag | aactcaggag | tgtgtgccat | 900 |
| gtgccagggc | tgaagaagat | gctgaggaca | tgtgcagtcc | acatcactct | ggatccagac | 960 |
| acagccaatc | cgtggctgat | actttcagaa | gatcggagac | aagtgaggct | tggagacacc | 1020 |
| cagcagagca | tacctggaaa | tgaagagaga | tttgatagtt | atcctatggt | cctgggtgcc | 1080 |
| cagcactttc | actctggaaa | acattactgg | gaggtagatg | tgacaggaaa | ggaggcctgg | 1140 |
| gacctgggtg | tctgcagaga | ctctgtgcgc | aggaaggggc | acttttttgct | tagttccaag | 1200 |
| agtggcttct | ggacaatttg | gttgtggaac | aaacaaaaat | atgaggctgg | cacctacccc | 1260 |
| cagactcccc | tccaccttca | ggtgcctcca | tgccaagttg | gattttcct | ggactatgag | 1320 |
| gctggcatgg | nctccttcta | caacatcact | gaccatggct | ccctcatcta | ctccttctct | 1380 |
| gaatgtgcct | tcacaggacc | tctgcggccc | ttcttcagtc | ctggtttcaa | tgatggagga | 1440 |
| aaaaacacag | cccctctaac | cctctgtcca | ctgaatattg | gatcacaagg | atccactgac | 1500 |
| tattg | | | | | | 1505 |

```
<210> SEQ ID NO 25
<211> LENGTH: 501
<212> TYPE: PRT
<213> ORGANISM: Homo sapiens
```

<220> FEATURE:
<221> NAME/KEY: misc_feature
<222> LOCATION: (444)..(444)
<223> OTHER INFORMATION: Xaa can be any naturally occurring amino acid

<400> SEQUENCE: 25

```
Met Ala Ser Met Thr Gly Gly Gln Gln Met Gly Arg Asp Pro Asn Ser
1               5                   10                  15

Ser Ser Val Asp His His His His His His Met Ala Ser Ala Ala Arg
            20                  25                  30

Leu Thr Met Met Trp Glu Glu Val Thr Cys Pro Ile Cys Leu Asp Pro
        35                  40                  45

Phe Val Glu Pro Val Gly Ile Glu Cys Gly His Ser Phe Cys Gln Glu
50                  55                  60

Cys Ile Ser Gln Val Gly Lys Gly Gly Ser Val Cys Pro Val Cys
65                  70                  75                  80

Arg Gln Arg Phe Leu Leu Lys Asn Leu Arg Pro Asn Arg Gln Leu Ala
                85                  90                  95

Asn Met Val Asn Asn Leu Lys Glu Ile Ser Gln Glu Ala Arg Glu Gly
            100                 105                 110

Thr Gln Gly Glu Arg Cys Ala Val His Gly Glu Arg Leu His Leu Phe
        115                 120                 125

Cys Glu Lys Asp Gly Lys Ala Leu Cys Trp Val Cys Ala Gln Ser Arg
130                 135                 140

Lys His Arg Asp His Ala Met Val Pro Leu Glu Glu Ala Ala Gln Glu
145                 150                 155                 160

Tyr Gln Glu Lys Leu His Val Ala Leu Gly Glu Leu Arg Arg Lys Gln
                165                 170                 175

Glu Leu Ala Glu Lys Leu Glu Val Glu Ile Ala Ile Lys Arg Ala Asp
            180                 185                 190

Trp Lys Lys Thr Val Glu Thr Gln Lys Ser Arg Ile His Ala Glu Phe
        195                 200                 205

Val Gln Gln Lys Asn Phe Leu Val Glu Glu Glu Gln Arg Gln Leu Gln
210                 215                 220

Glu Leu Glu Lys Asp Glu Arg Glu Gln Leu Arg Ile Leu Gly Glu Lys
225                 230                 235                 240

Glu Ala Lys Leu Ala Gln Gln Ser Gln Ala Leu Gln Glu Leu Ile Ser
                245                 250                 255

Glu Leu Asp Arg Arg Cys His Ser Ser Ala Leu Glu Leu Leu Gln Glu
            260                 265                 270

Val Ile Ile Val Leu Glu Arg Ser Glu Ser Trp Asn Leu Lys Asp Leu
        275                 280                 285

Asp Ile Thr Ser Pro Glu Leu Arg Ser Val Cys His Val Pro Gly Leu
290                 295                 300

Lys Lys Met Leu Arg Thr Cys Ala Val His Ile Thr Leu Asp Pro Asp
305                 310                 315                 320

Thr Ala Asn Pro Trp Leu Ile Leu Ser Glu Asp Arg Arg Gln Val Arg
                325                 330                 335

Leu Gly Asp Thr Gln Gln Ser Ile Pro Gly Asn Glu Glu Arg Phe Asp
            340                 345                 350

Ser Tyr Pro Met Val Leu Gly Ala Gln His Phe His Ser Gly Lys His
        355                 360                 365

Tyr Trp Glu Val Asp Val Thr Gly Lys Glu Ala Trp Asp Leu Gly Val
370                 375                 380
```

```
Cys Arg Asp Ser Val Arg Arg Lys Gly His Phe Leu Leu Ser Ser Lys
385                 390                 395                 400

Ser Gly Phe Trp Thr Ile Trp Leu Trp Asn Lys Gln Lys Tyr Glu Ala
                405                 410                 415

Gly Thr Tyr Pro Gln Thr Pro Leu His Leu Gln Val Pro Pro Cys Gln
            420                 425                 430

Val Gly Ile Phe Leu Asp Tyr Glu Ala Gly Met Xaa Ser Phe Tyr Asn
        435                 440                 445

Ile Thr Asp His Gly Ser Leu Ile Tyr Ser Phe Ser Glu Cys Ala Phe
    450                 455                 460

Thr Gly Pro Leu Arg Pro Phe Phe Ser Pro Gly Phe Asn Asp Gly Gly
465                 470                 475                 480

Lys Asn Thr Ala Pro Leu Thr Leu Cys Pro Leu Asn Ile Gly Ser Gln
                485                 490                 495

Gly Ser Thr Asp Tyr
            500
```

<210> SEQ ID NO 26
<211> LENGTH: 1428
<212> TYPE: DNA
<213> ORGANISM: Homo sapiens

<400> SEQUENCE: 26

```
atggaattcc atcatcatca tcatcatggt gttatggcta gcatgactgg tggacagcaa      60
atgggtatgc tggcggaaaa cctggtagag gagtttgaga tgaaggagga cgagccgtgg     120
tacgaccacc aggacctcca gcaagatctt caacttgctg ctgagcttgg aagacatta     180
ctggatcgga acacagagtt ggaggactct gttcagcaga tgtatacaac caatcaggag     240
cagttacagg aaattgagta tctgacgaag caagtggaac ttctacggca gatgaacgaa     300
caacatgcaa aggtttatga caattagac gtcacagcaa gggaactgga agaaacaaat     360
caaaagctag ttgctgacag caaggcctca gcaaaagga ttctgagcct gactgaaacg     420
attgaatgcc tgcaaaccaa cattgatcac ctccagagcc aagtggagga gctgaagtca     480
tctggccaag gggaaggag cccgggaaag tgtgaccagg agaaaccggc acccagcttt     540
gcatgtctga aggagctgta tgacctccgc caacacttcg tgtatgatca tgtgttcgct     600
gagaagatca cttccttgca aggtcagcca agccctgatg aagaggaaaa tgagcacttg     660
aaaaaaacag tgacaatgtt gcaggcccag ctgagcctgg agcggcagaa gcgggtgact     720
atggaggagg aatatggct cgtgttaaag gagaacagtg aactggagca gcagctgggg     780
gccacaggtg cctaccgagc acgggcgctg aactagagg ccgaggtggc agagatgcga     840
cagatgttgc agtcagagca tccatttgtg aatggagttg agaagctggt gccagactct     900
ctgtatgttc ctttcaaaga gcccagccag agcctgctgg aagagatgtt cctgactgtg     960
ccggaatcac atagaaagcc ctcaagcgc agcagcagtg agacgatcct cagcagcttg    1020
gcagggagtg acatcgtgaa gggccacgag gagacctgca tcaggagggc caaggctgtg    1080
aaacagaggg gcatctccct tctgcacgaa gtggacacgc agtacagcgc cctgaaggtg    1140
aagtatgaag agttgctgaa gaagtgccaa gaggaacagg actccctgtc acacaaggct    1200
gtgcagacct ccagggctgc agccaaggac ctgactggag tgaacgccca gtctgagcct    1260
gttgccagcg gctgggaact ggcctctgtc aacccagagc ccgtgagttc ccctacaaca    1320
cctccagaat acaaagcgtt gtttaaggag atctttagtt gcatcaagaa actaagcag    1380
gaaatagatg aacagagaac aaaataccga tcactctcct ctcattct              1428
```

<210> SEQ ID NO 27
<211> LENGTH: 476
<212> TYPE: PRT
<213> ORGANISM: Homo sapiens

<400> SEQUENCE: 27

| Met | Glu | Phe | His | His | His | His | His | Gly | Val | Met | Ala | Ser | Met | Thr |
|---|---|---|---|---|---|---|---|---|---|---|---|---|---|---|
| 1 | | | | 5 | | | | | 10 | | | | | 15 |

Gly Gly Gln Gln Met Gly Met Leu Ala Glu Asn Leu Val Glu Glu Phe
            20                  25                  30

Glu Met Lys Glu Asp Glu Pro Trp Tyr Asp His Gln Asp Leu Gln Gln
        35                  40                  45

Asp Leu Gln Leu Ala Ala Glu Leu Gly Lys Thr Leu Leu Asp Arg Asn
    50                  55                  60

Thr Glu Leu Glu Asp Ser Val Gln Gln Met Tyr Thr Thr Asn Gln Glu
65                  70                  75                  80

Gln Leu Gln Glu Ile Glu Tyr Leu Thr Lys Gln Val Glu Leu Leu Arg
                85                  90                  95

Gln Met Asn Glu Gln His Ala Lys Val Tyr Glu Gln Leu Asp Val Thr
            100                 105                 110

Ala Arg Glu Leu Glu Glu Thr Asn Gln Lys Leu Val Ala Asp Ser Lys
        115                 120                 125

Ala Ser Gln Gln Lys Ile Leu Ser Leu Thr Glu Thr Ile Glu Cys Leu
    130                 135                 140

Gln Thr Asn Ile Asp His Leu Gln Ser Gln Val Glu Glu Leu Lys Ser
145                 150                 155                 160

Ser Gly Gln Gly Gly Arg Ser Pro Gly Lys Cys Asp Gln Glu Lys Pro
                165                 170                 175

Ala Pro Ser Phe Ala Cys Leu Lys Glu Leu Tyr Asp Leu Arg Gln His
            180                 185                 190

Phe Val Tyr Asp His Val Phe Ala Glu Lys Ile Thr Ser Leu Gln Gly
        195                 200                 205

Gln Pro Ser Pro Asp Glu Glu Asn Glu His Leu Lys Lys Thr Val
    210                 215                 220

Thr Met Leu Gln Ala Gln Leu Ser Leu Glu Arg Gln Lys Arg Val Thr
225                 230                 235                 240

Met Glu Glu Glu Tyr Gly Leu Val Leu Lys Glu Asn Ser Glu Leu Glu
                245                 250                 255

Gln Gln Leu Gly Ala Thr Gly Ala Tyr Arg Ala Arg Ala Leu Glu Leu
            260                 265                 270

Glu Ala Glu Val Ala Glu Met Arg Gln Met Leu Gln Ser Glu His Pro
        275                 280                 285

Phe Val Asn Gly Val Glu Lys Leu Val Pro Asp Ser Leu Tyr Val Pro
    290                 295                 300

Phe Lys Glu Pro Ser Gln Ser Leu Leu Glu Glu Met Phe Leu Thr Val
305                 310                 315                 320

Pro Glu Ser His Arg Lys Pro Leu Lys Arg Ser Ser Glu Thr Ile
                325                 330                 335

Leu Ser Ser Leu Ala Gly Ser Asp Ile Val Lys Gly His Glu Glu Thr
            340                 345                 350

Cys Ile Arg Arg Ala Lys Ala Val Lys Gln Arg Gly Ile Ser Leu Leu
        355                 360                 365

His Glu Val Asp Thr Gln Tyr Ser Ala Leu Lys Val Lys Tyr Glu Glu

-continued

```
              370                 375                 380
Leu Leu Lys Lys Cys Gln Glu Gln Asp Ser Leu Ser His Lys Ala
385                 390                 395                 400

Val Gln Thr Ser Arg Ala Ala Ala Lys Asp Leu Thr Gly Val Asn Ala
                405                 410                 415

Gln Ser Glu Pro Val Ala Ser Gly Trp Glu Leu Ala Ser Val Asn Pro
                420                 425                 430

Glu Pro Val Ser Ser Pro Thr Thr Pro Pro Glu Tyr Lys Ala Leu Phe
            435                 440                 445

Lys Glu Ile Phe Ser Cys Ile Lys Lys Thr Lys Gln Glu Ile Asp Glu
    450                 455                 460

Gln Arg Thr Lys Tyr Arg Ser Leu Ser Ser His Ser
465                 470                 475
```